(12) United States Patent
Fuerst et al.

(10) Patent No.: US 9,289,217 B2
(45) Date of Patent: *Mar. 22, 2016

(54) METHOD AND SYSTEM FOR CIRCUMCISION

(71) Applicant: Circ MedTech Ltd., Tortola (VG)

(72) Inventors: Oren Fuerst, Ramat Hasharon (IL); Ido Kilemnick, Herzelia (IL); Shaul Shohat, Kfar Haoranim (IL)

(73) Assignee: CIRC MEDTECH LTD., Road Town, Tortola (VG)

( * ) Notice: Subject to any disclaimer, the term of this patent is extended or adjusted under 35 U.S.C. 154(b) by 0 days.

This patent is subject to a terminal disclaimer.

(21) Appl. No.: 14/615,926

(22) Filed: Feb. 6, 2015

(65) Prior Publication Data

US 2015/0209051 A1    Jul. 30, 2015

Related U.S. Application Data

(63) Continuation of application No. 13/383,964, filed as application No. PCT/IL2010/000568 on Jul. 15, 2010, now Pat. No. 8,974,471.

(60) Provisional application No. 61/348,129, filed on May 25, 2010, provisional application No. 61/300,525, filed on Feb. 2, 2010, provisional application No. 61/244,157, filed on Sep. 21, 2009, provisional application No. 61/225,947, filed on Jul. 16, 2009.

(51) Int. Cl.
*A61B 17/42* (2006.01)
*A61B 17/132* (2006.01)
(Continued)

(52) U.S. Cl.
CPC ........... *A61B 17/1322* (2013.01); *A61B 17/326* (2013.01); *A61H 19/32* (2013.01); *A61H 23/02* (2013.01); *A61H 39/002* (2013.01); *A61B 2017/0073* (2013.01); *A61B 2017/00867* (2013.01); *A61B 2019/442* (2013.01); *A61B 2019/448* (2013.01); *A61B 2019/461* (2013.01); *A61M 35/00* (2013.01)

(58) Field of Classification Search
CPC ............. A61B 17/1322; A61B 17/326; A61B 2017/0073; A61B 2019/461; A61B 2017/00867; A61B 2019/448; A61B 2019/442; A61H 19/32; A61H 23/02; A61H 39/002; A61M 35/00
USPC .......................... 606/118, 167, 171, 135, 174
See application file for complete search history.

(56) References Cited

U.S. PATENT DOCUMENTS 2,353,647 A * 7/1944 Carmichael ................... 606/118
2,538,136 A * 1/1951 Twachtman ..................... 602/1
(Continued)

FOREIGN PATENT DOCUMENTS

GB          381881 A     10/1982
WO     2005056723 A1     6/2005

*Primary Examiner* — Amy R Weisberg
(74) *Attorney, Agent, or Firm* — Greenberg Traurig, LLP

(57) ABSTRACT

A system for effecting ischemic necrosis in a foreskin of a penis includes an inner ring having an inner surface comprising an inner diameter and an outer surface comprising an outer diameter and at least one circumferential groove; and an outer ring configured to substantially fit around the circumferential groove of the inner ring, wherein the inner ring is configured to fit to a portion of a glans of the penis that lies between an inner surface of the foreskin and the glans of the penis and the at least one outer ring is configured to fit an outer surface of the foreskin, the inner ring and the outer ring thereby compressing the foreskin in the circumferential groove with a compression force, and wherein the compression force is sufficient to effect ischemic necrosis in the foreskin.

6 Claims, 38 Drawing Sheets

(51) Int. Cl.
- *A61B 17/326* (2006.01)
- *A61H 23/02* (2006.01)
- *A61H 39/00* (2006.01)
- *A61H 19/00* (2006.01)
- *A61B 17/00* (2006.01)
- *A61B 19/00* (2006.01)
- *A61M 35/00* (2006.01)

(56) References Cited

U.S. PATENT DOCUMENTS

| | | | | |
|---|---|---|---|---|
| 2,544,037 | A * | 3/1951 | Moseley | 606/118 |
| 2,561,176 | A * | 7/1951 | Buckingham | 606/118 |
| 2,601,470 | A * | 6/1952 | Turner | 606/118 |
| 3,111,124 | A * | 11/1963 | Rodbard | 606/118 |
| 3,612,057 | A * | 10/1971 | Freedman | 606/118 |
| 3,625,218 | A * | 12/1971 | Valinoti, Jr. | 606/45 |
| 3,893,455 | A * | 7/1975 | McNally | 600/41 |
| 4,170,990 | A * | 10/1979 | Baumgart et al. | 606/78 |
| 4,491,136 | A * | 1/1985 | LeVeen | 606/118 |
| 5,269,788 | A * | 12/1993 | Nelson, III | 606/118 |
| 5,860,988 | A * | 1/1999 | Rawlings | 606/118 |
| 6,991,600 | B1 * | 1/2006 | Wang | 600/38 |
| D670,807 | S * | 11/2012 | Fuerst | D24/143 |
| 2005/0221363 | A1 | 10/2005 | Spain et al. | |
| 2009/0084029 | A1 | 4/2009 | Bergman | |
| 2011/0098718 | A1 * | 4/2011 | Shang | 606/118 |
| 2012/0109145 | A1 * | 5/2012 | Gumkowski | 606/118 |
| 2012/0203242 | A1 * | 8/2012 | Fuerst et al. | 606/118 |
| 2012/0277759 | A1 * | 11/2012 | Shang | 606/118 |
| 2012/0303040 | A1 * | 11/2012 | Johnson et al. | 606/118 |
| 2012/0303041 | A1 * | 11/2012 | Marczyk et al. | 606/118 |
| 2013/0144304 | A1 * | 6/2013 | Shang et al. | 606/118 |
| 2013/0325026 | A1 * | 12/2013 | Fuerst et al. | 606/118 |
| 2015/0209051 | A1 * | 7/2015 | Fuerst et al. | 606/118 |

* cited by examiner

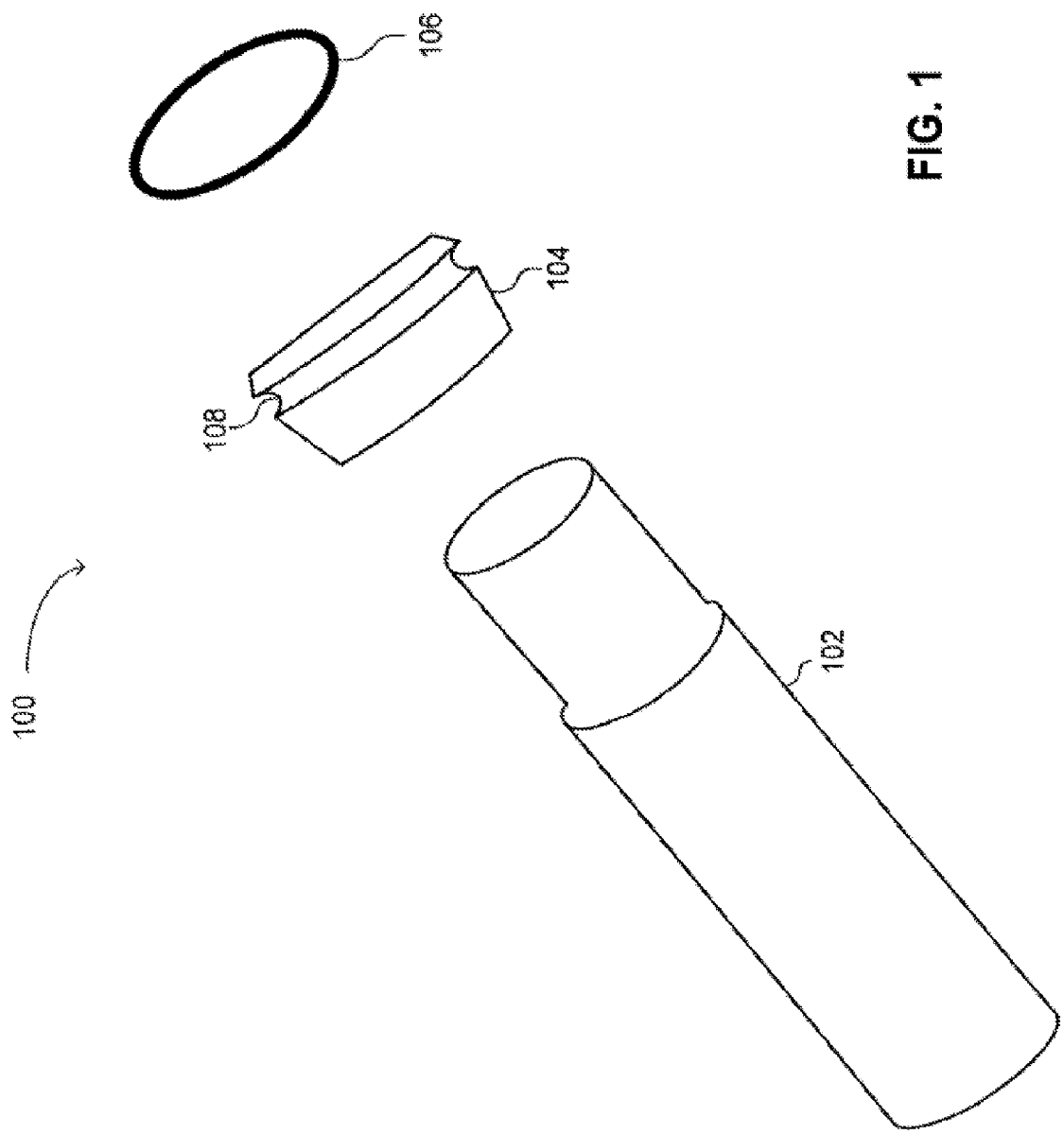

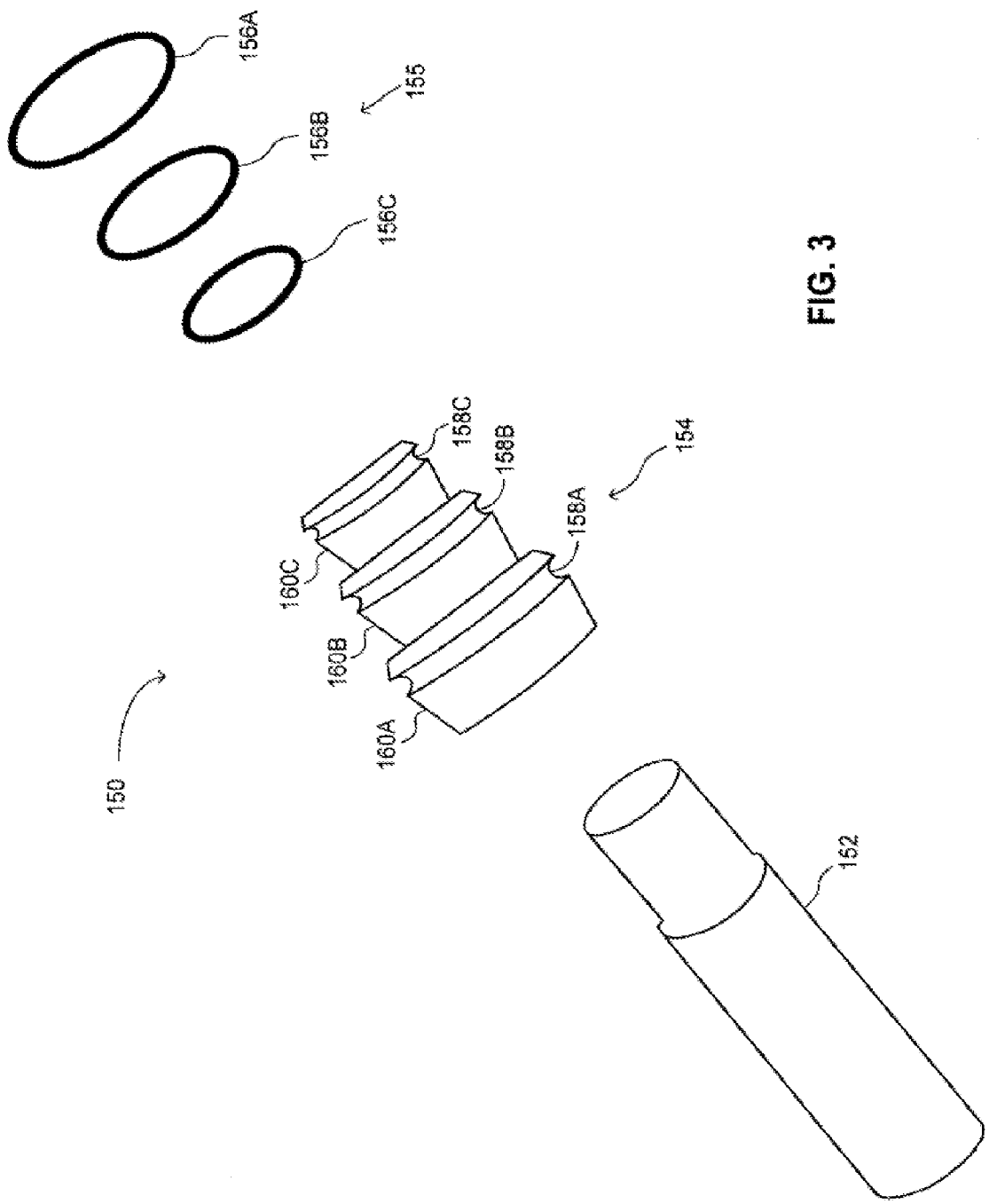

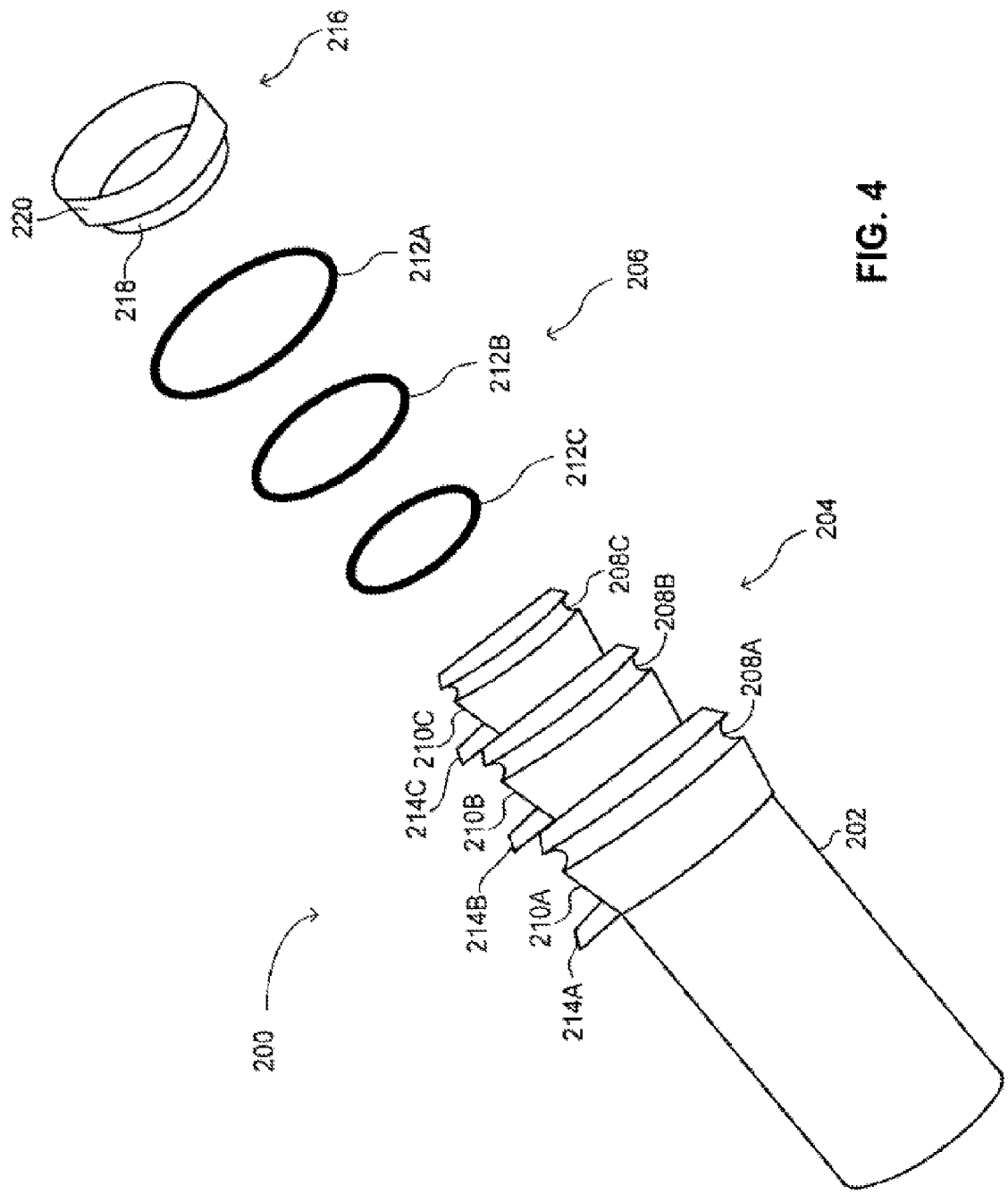

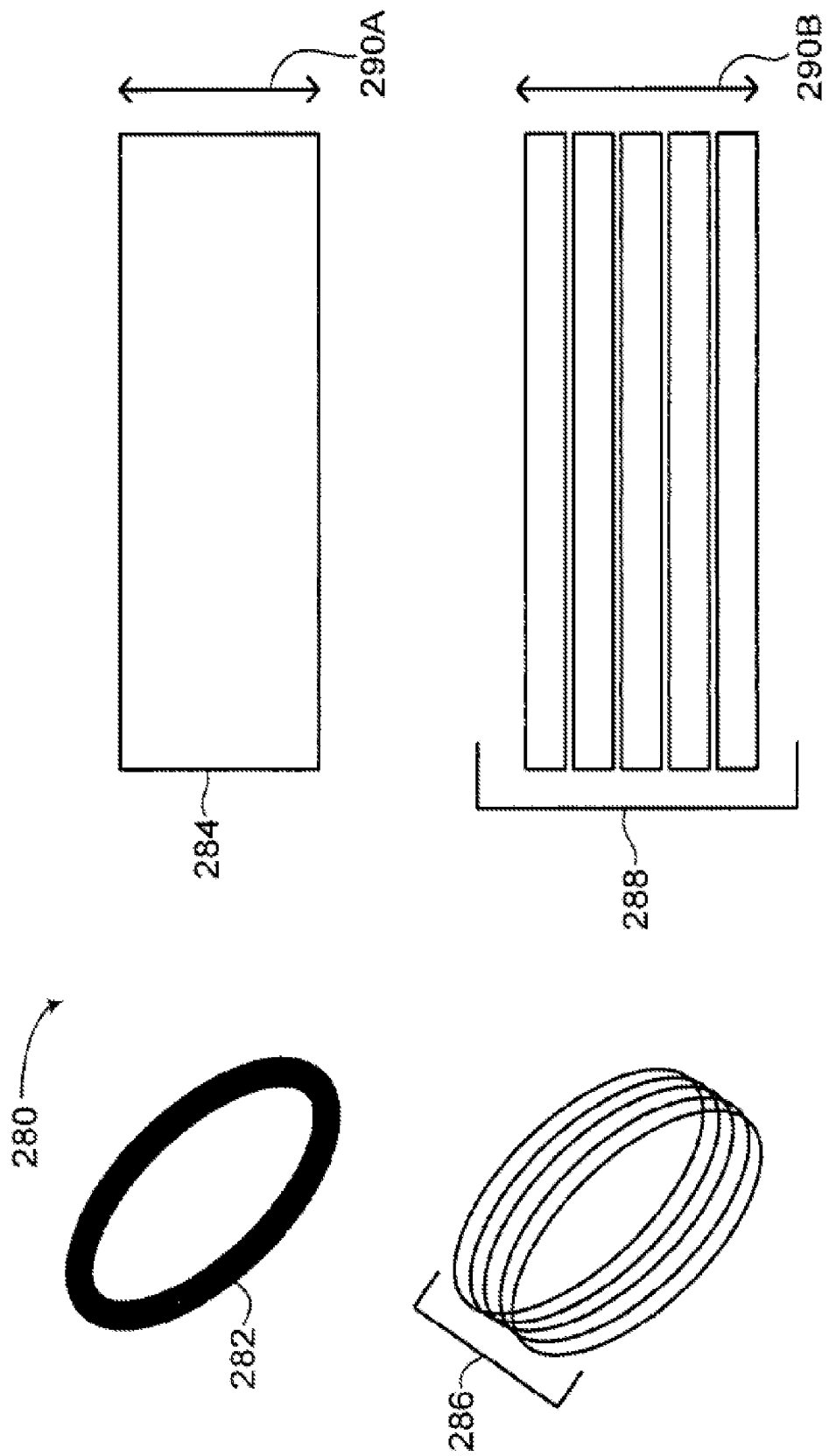

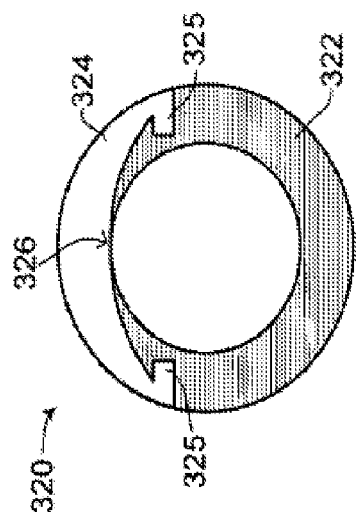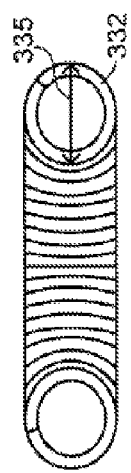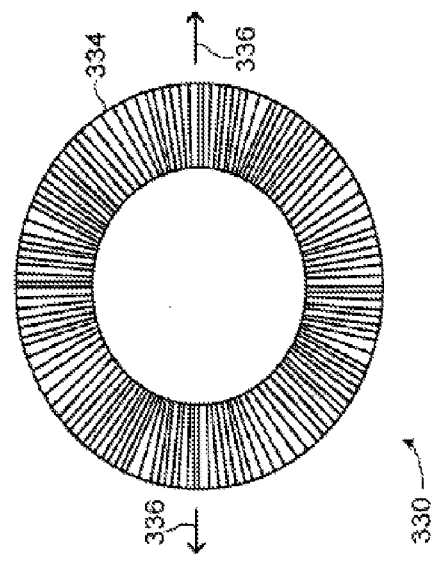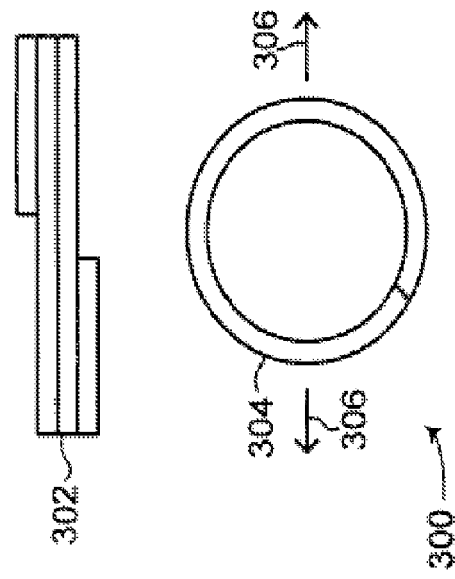

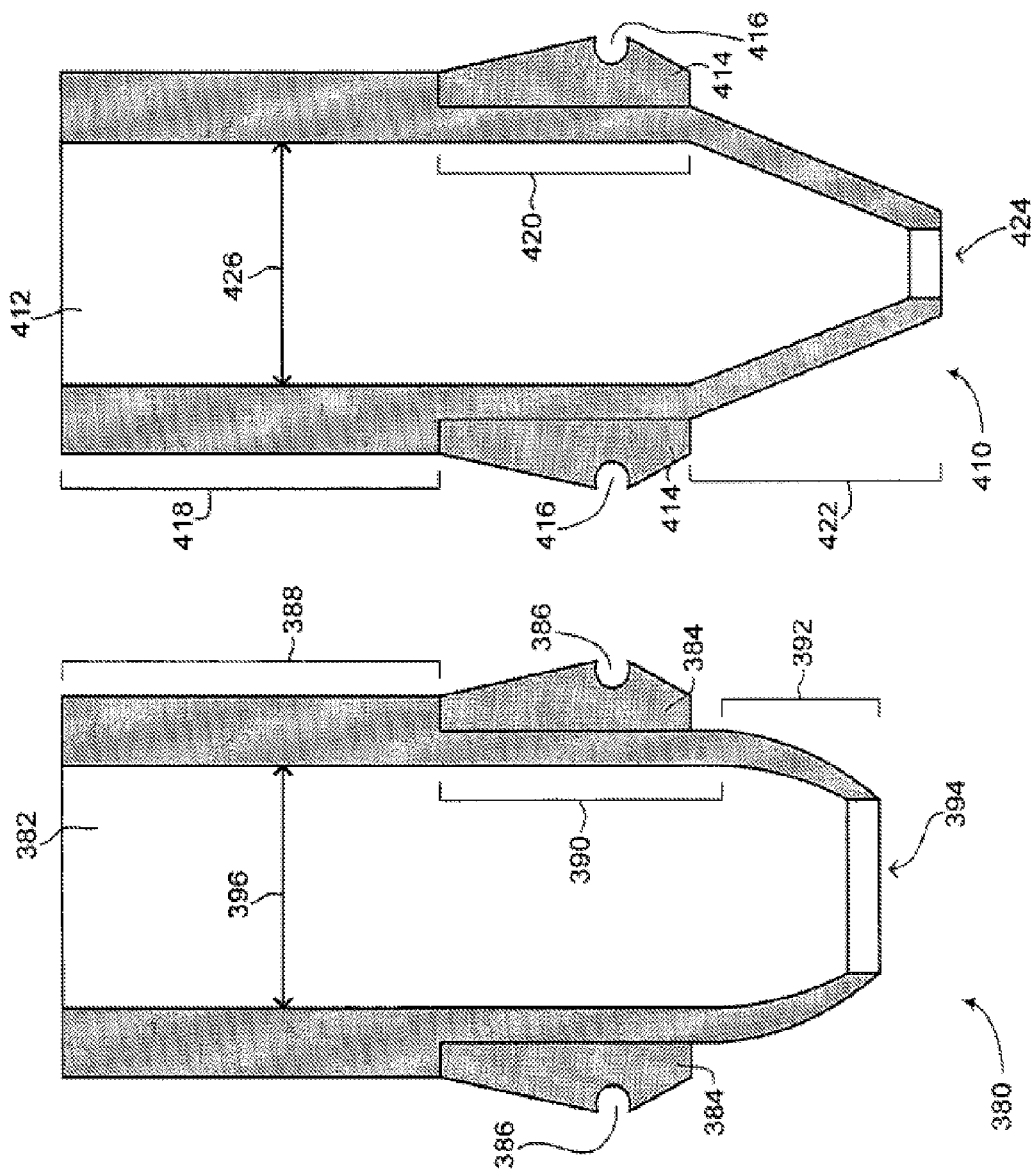

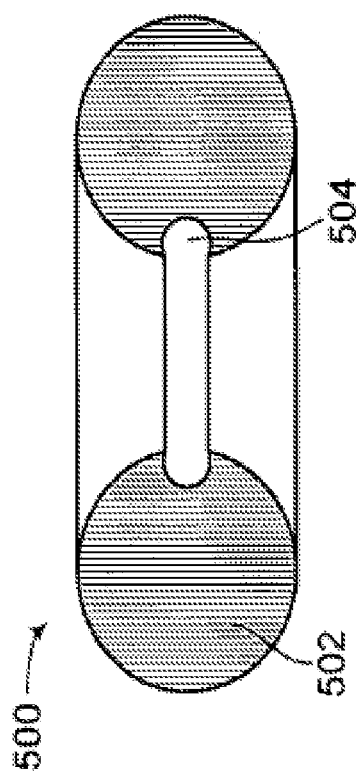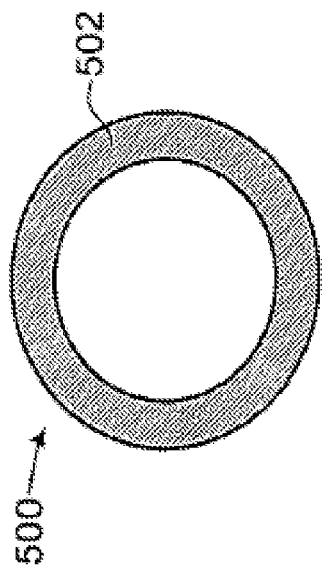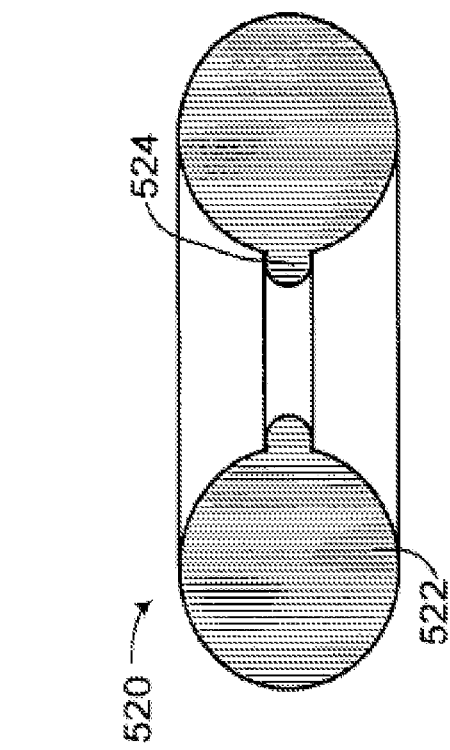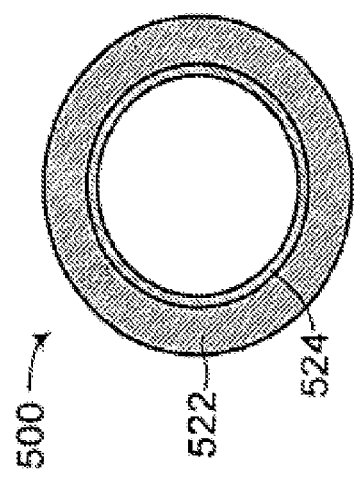
FIG. 10A
FIG. 10B
FIG. 10C
FIG. 10D

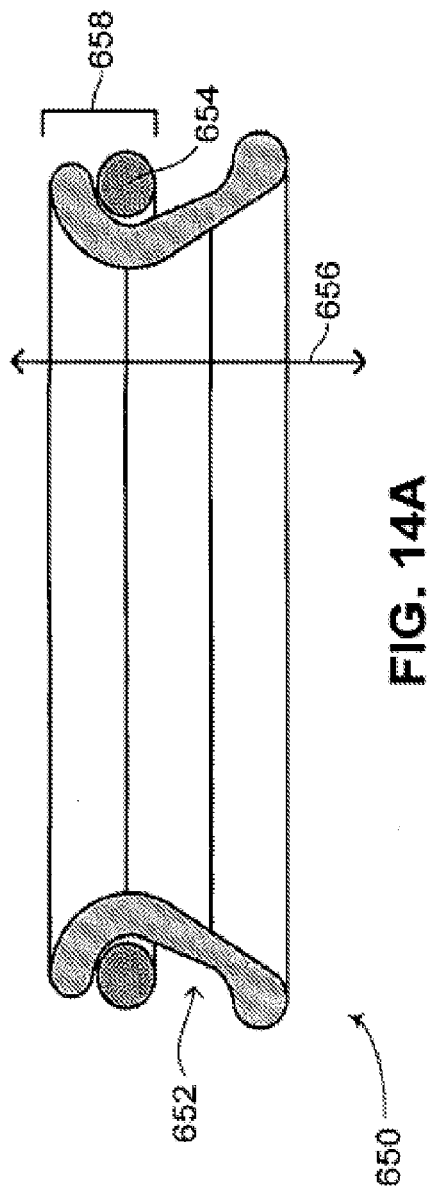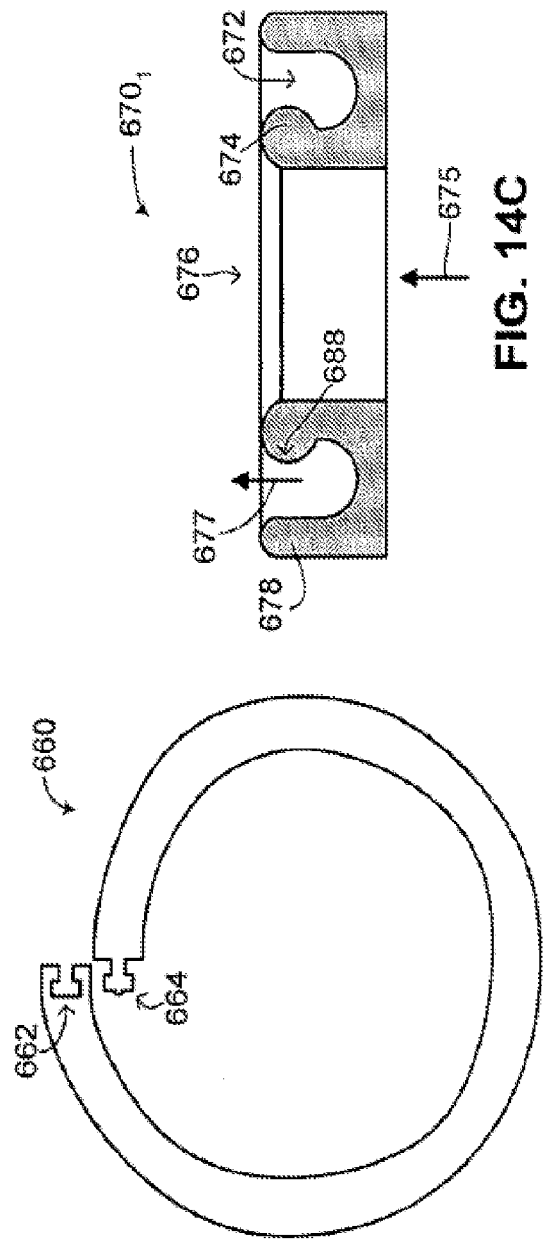

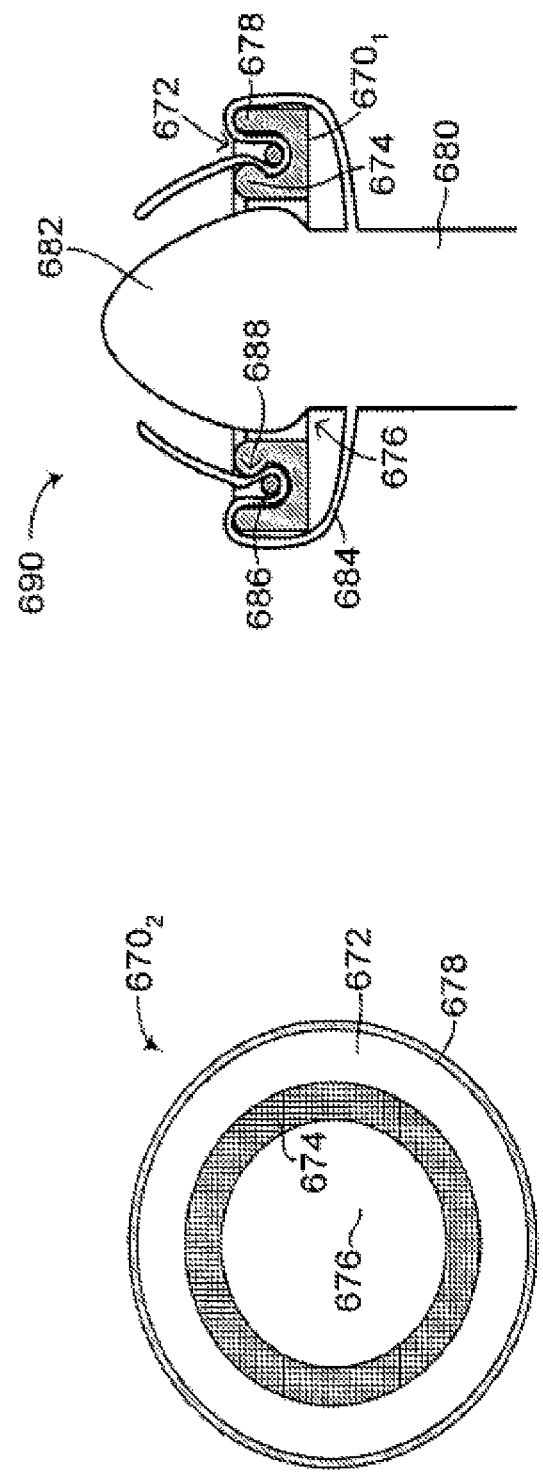

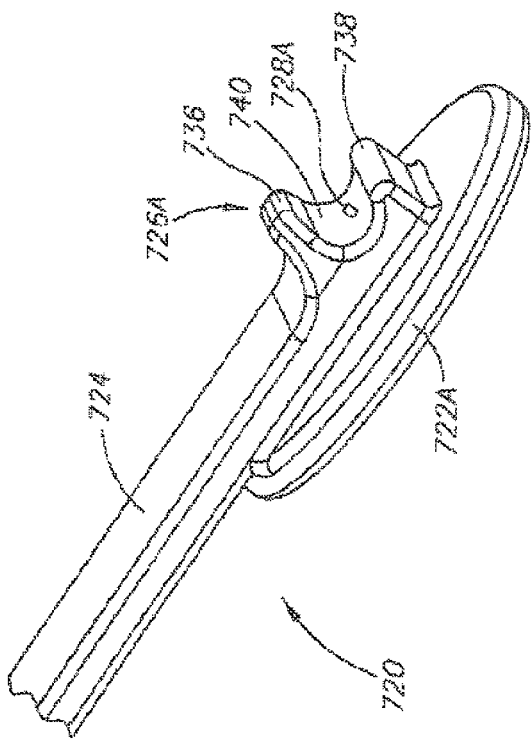
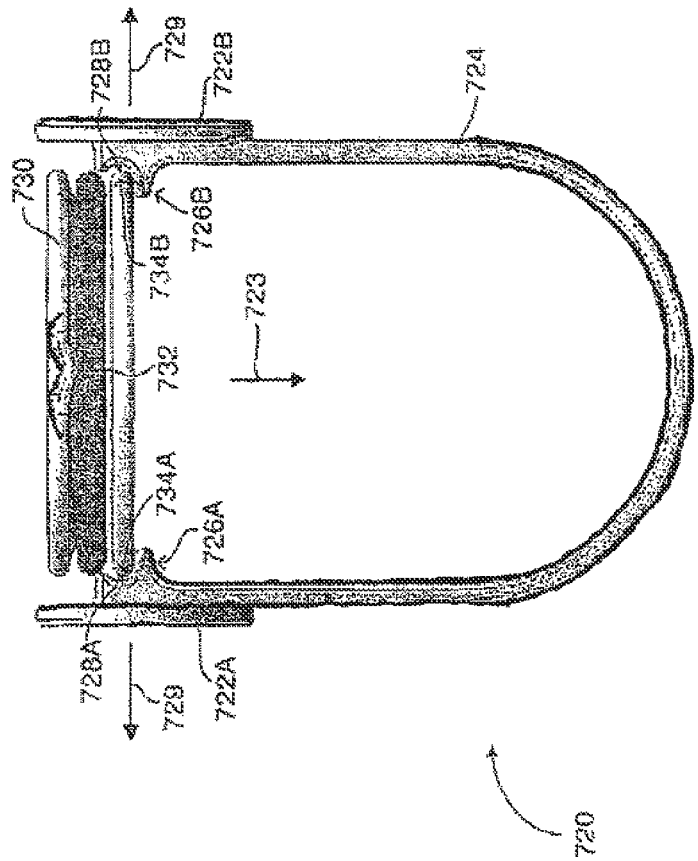
FIG. 15A
FIG. 15B

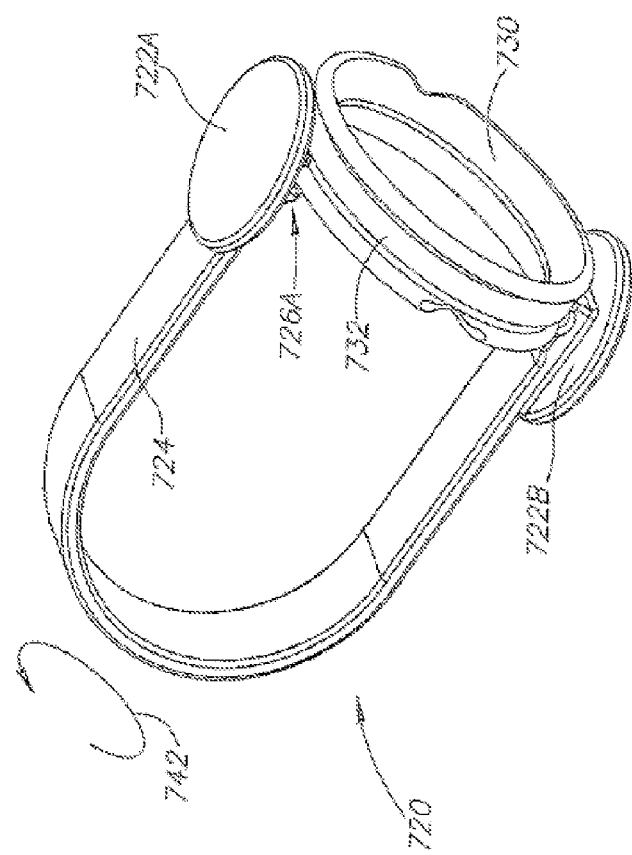
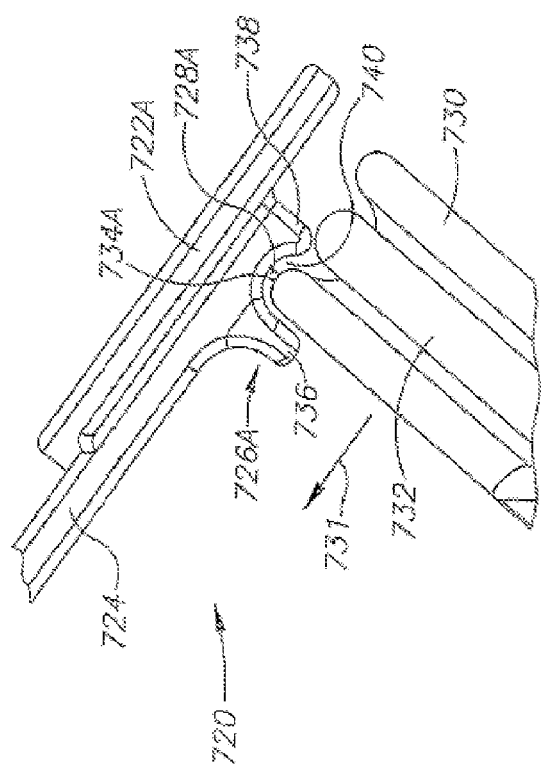
FIG.15D
FIG.15C

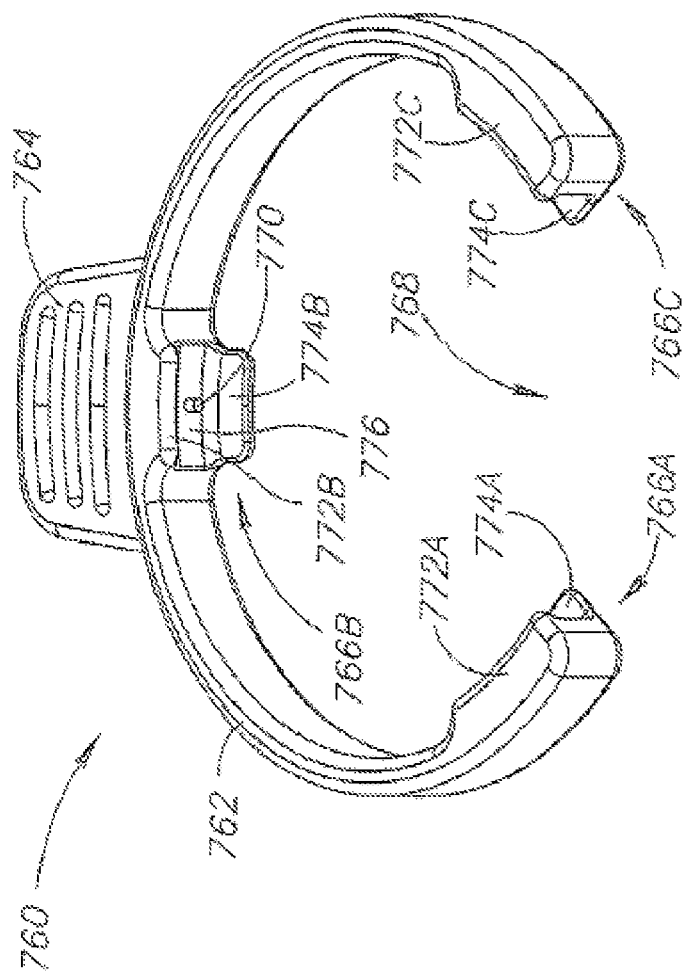

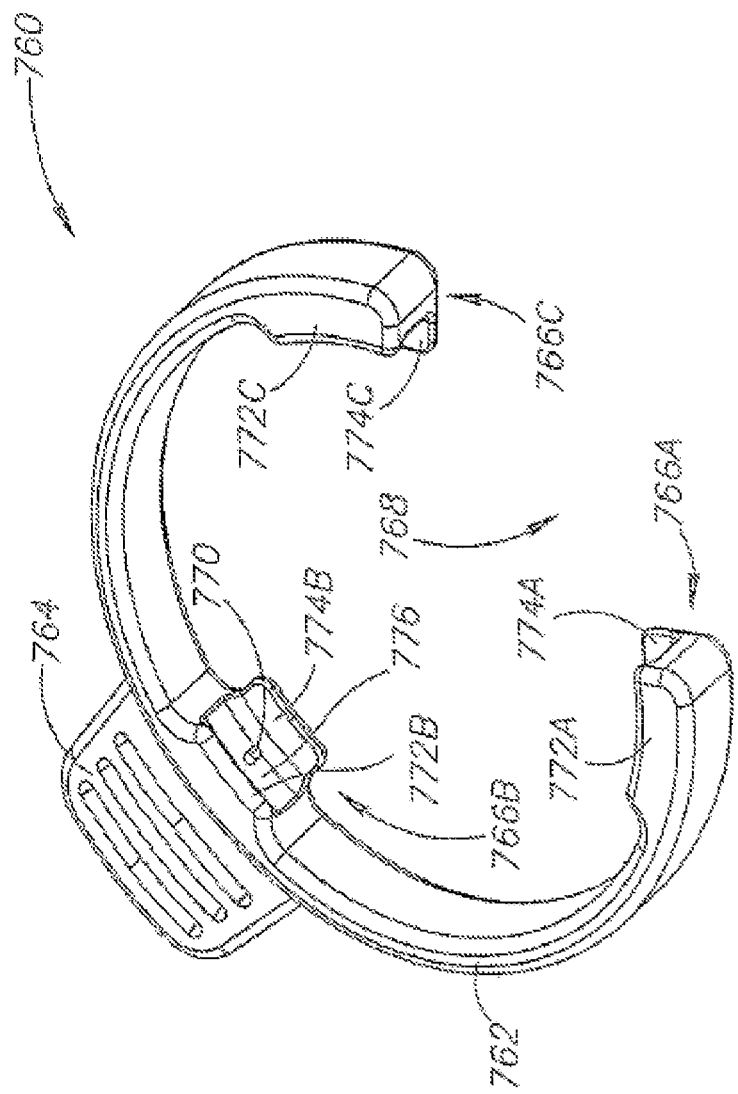

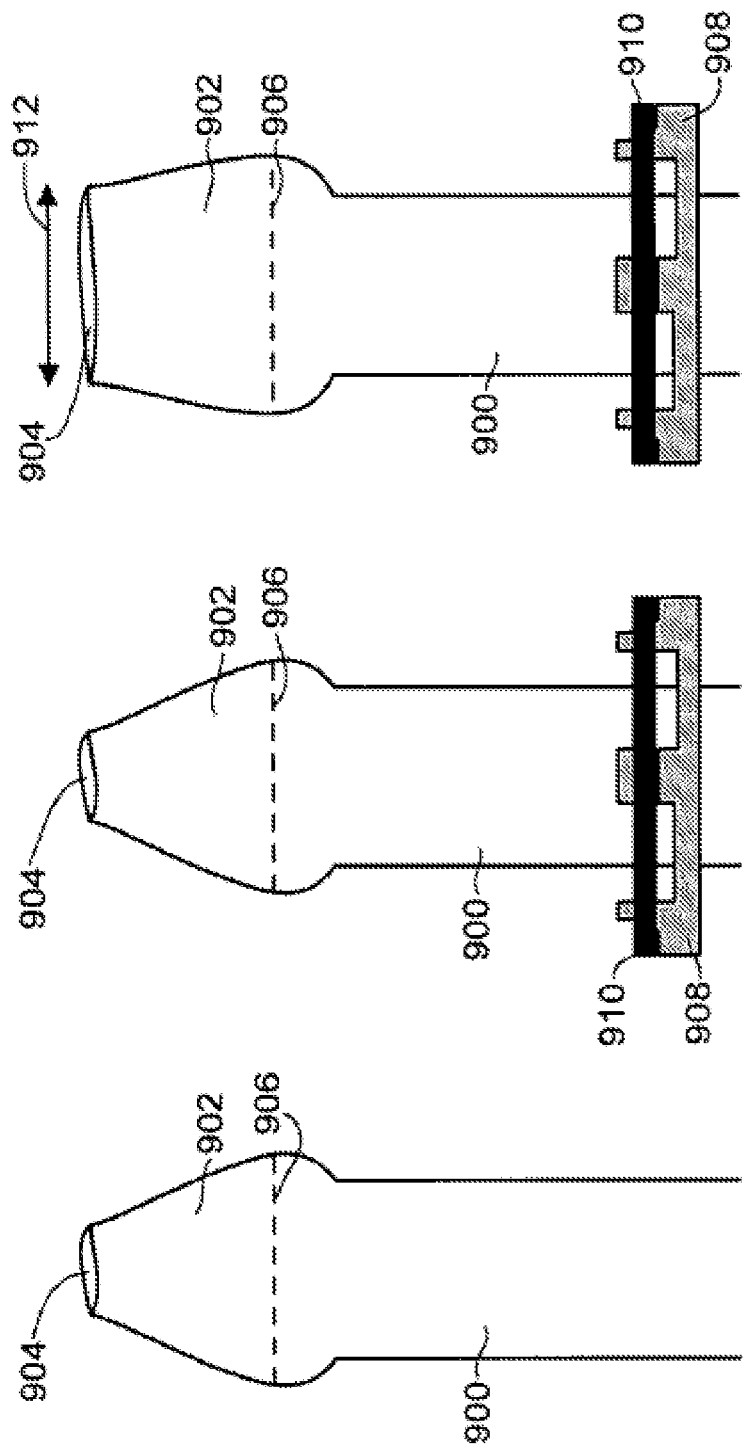

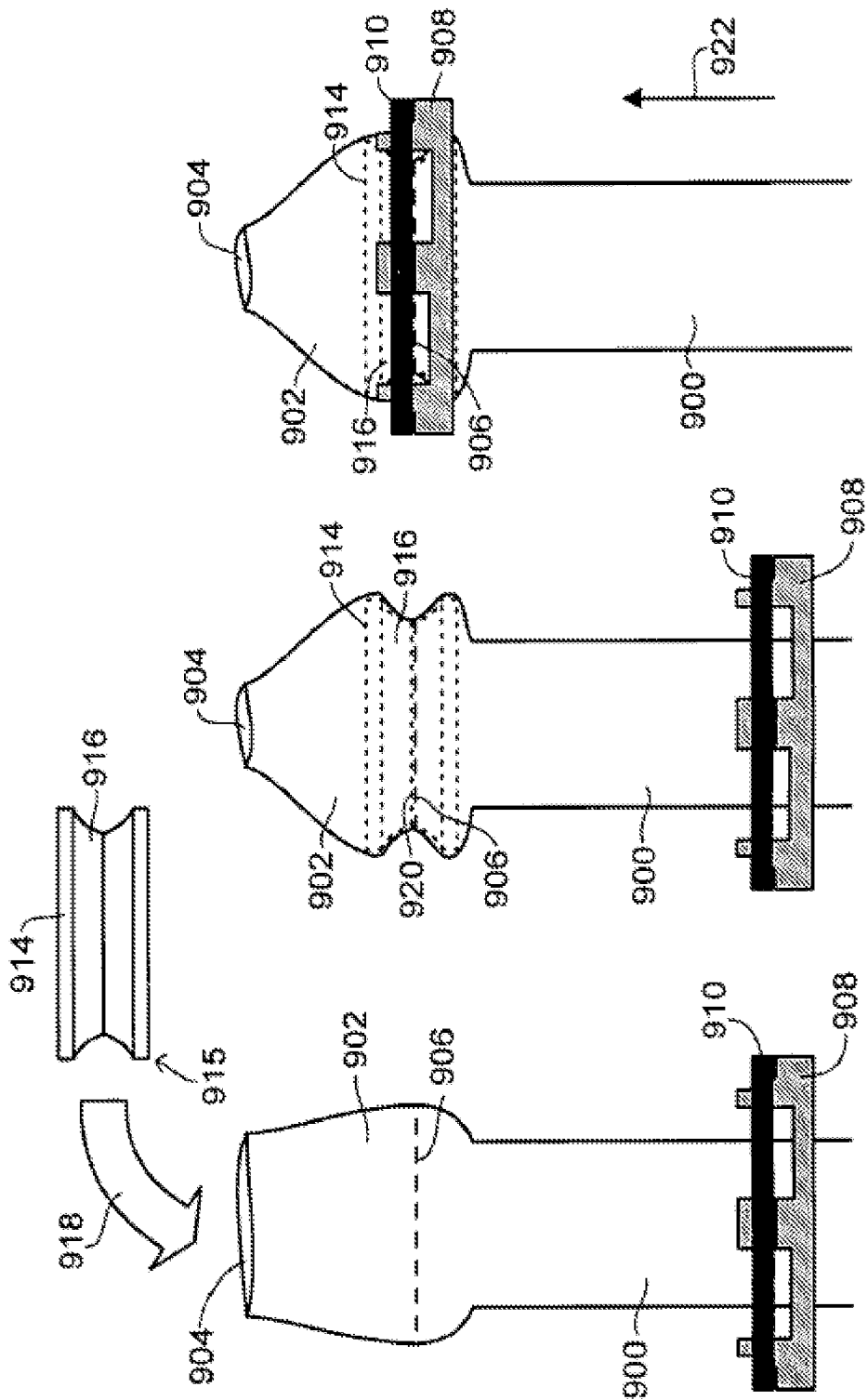

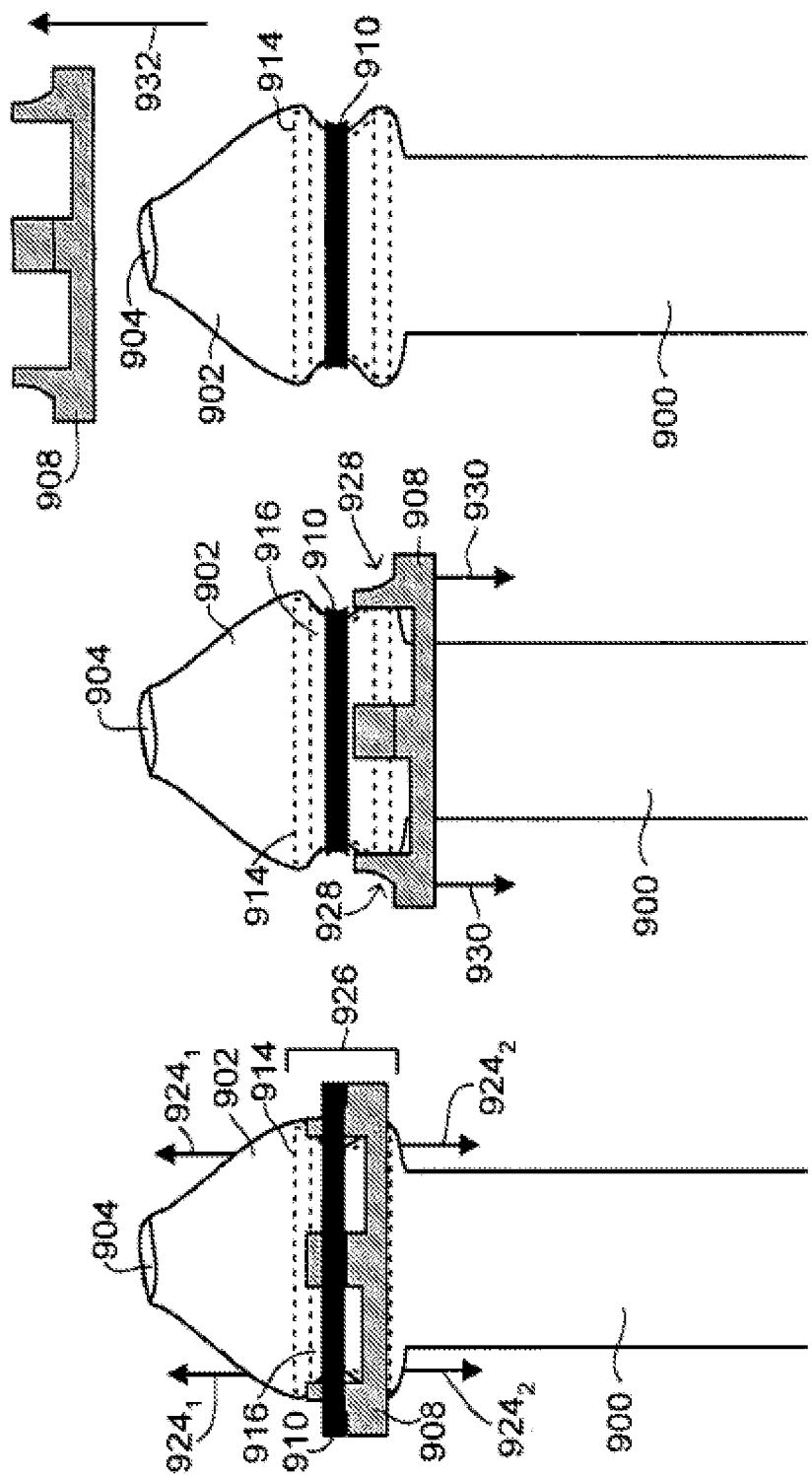

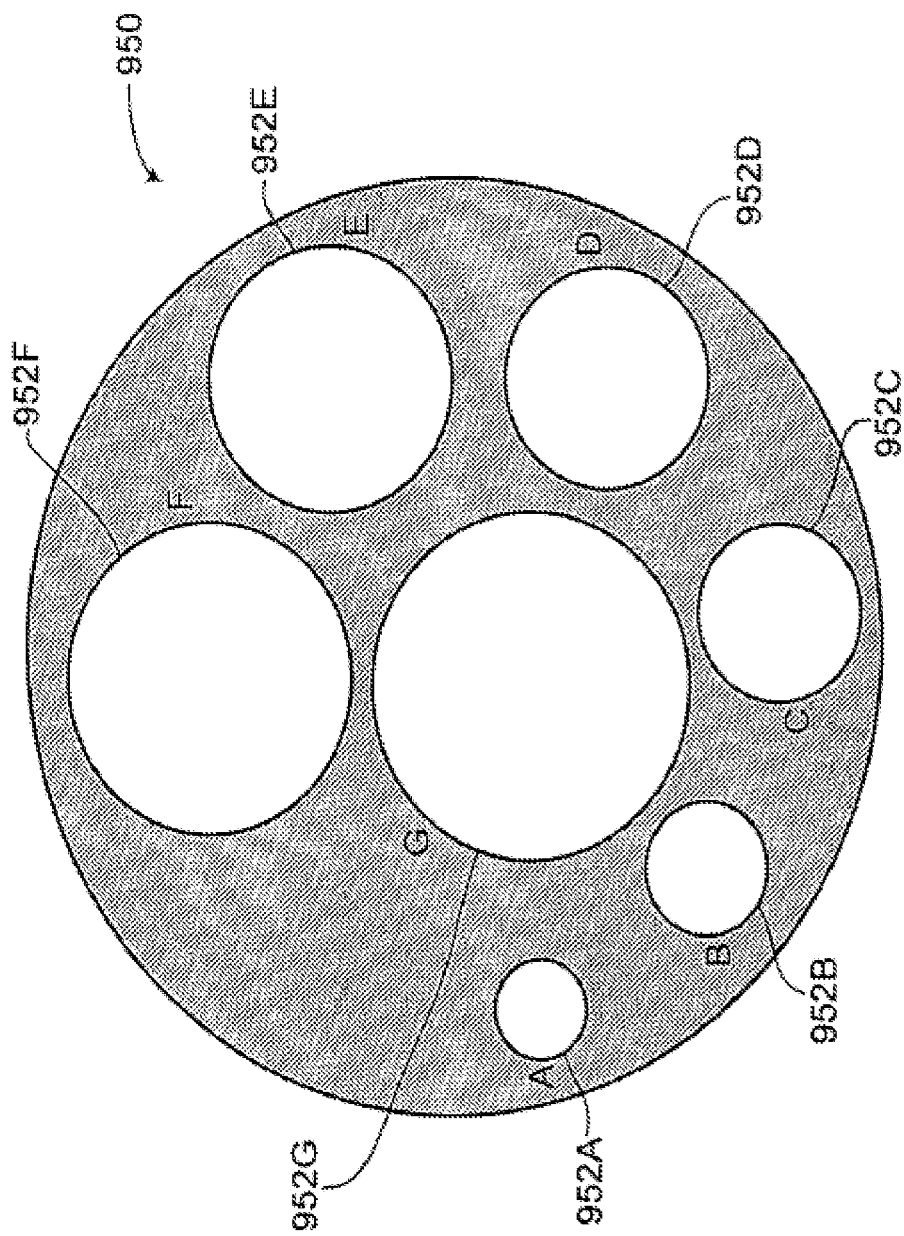

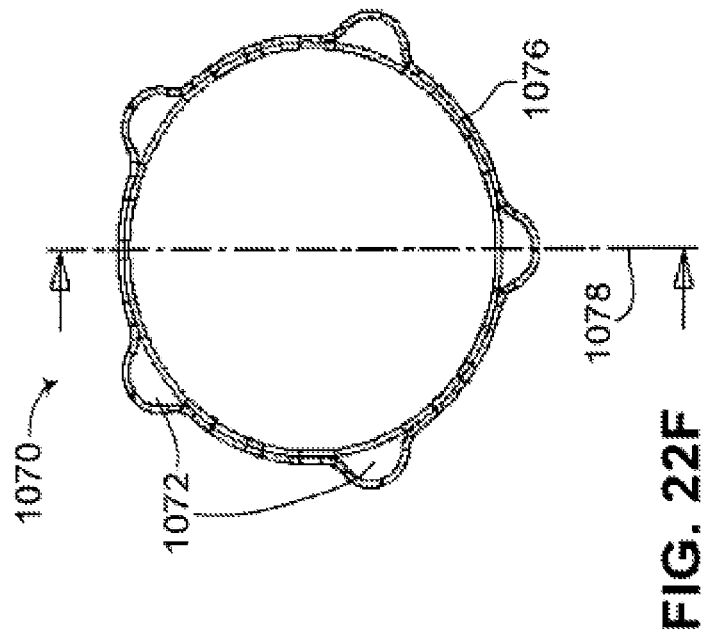
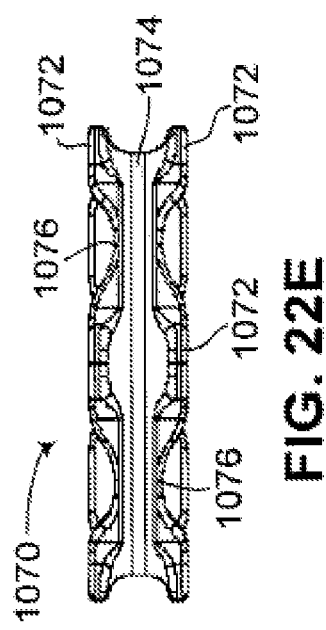
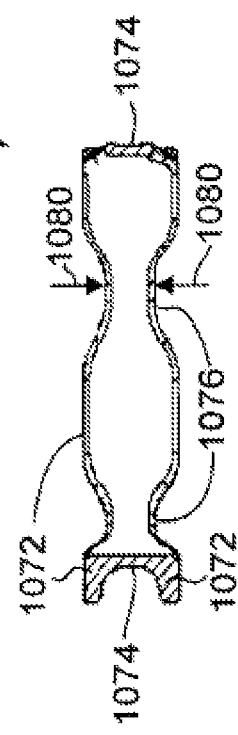
FIG. 22F
FIG. 22E
FIG. 22G

METHOD AND SYSTEM FOR CIRCUMCISION

RELATED APPLICATIONS

The present application is a Continuation of application Ser. No. 13/383,964, filed on Jan. 13, 2012, now U.S. Pat. No. 8,974,471, which is a national phase filing under 35 U.S.C. 371 of International application No. PCT/IL10/00568, filed on Jul. 15, 2010, which claims the benefit of and priority to Provisional application No. 61/225,947, filed on Jul. 16, 2009, Provisional application No. 61/244,157, filed on Sep. 21, 2009, Provisional application No. 61/300,525, filed on Feb. 2, 2010, and Provisional application No. 61/348,129, filed on May 25, 2010, all of which are incorporated herein by reference in their entirety.

BACKGROUND OF THE DISCLOSED TECHNIQUE

The foreskin of a penis is an excess of skin, located proximate to the distal end of the penis, also referred to as the prepuce. The foreskin substantially covers the head of the penis, also known as the glans of the penis, the glans penis or simply the glans. Circumcision is a surgical operation in which either a portion or all the foreskin of the penis is removed. Male circumcision is one of the most common surgical procedures in the world and has been performed for ritualistic as well as hygienic reasons since ancient times. Nowadays, it may be performed for clinical reasons or to comply with religious or cultural practices (also known as non-therapeutic circumcision). Non-therapeutic circumcisions are generally performed in a religious or cultural community by general practitioners and non-clinicians. Approximately a third of human males worldwide receive a circumcision at some point in their lives. Circumcision has traditionally been performed either immediately after birth, during childhood, during adolescence or occasionally on young adults (i.e., after the teenage years).

The human immunodeficiency virus (herein abbreviated HIV) is a virus which causes AIDS, a deadly disease which has claimed more than 25 million lives worldwide since its discovery in 1981. Approximately 2 million people worldwide are infected with HIV every year, wherein roughly two thirds of those infected with HIV live in Sub-Saharan Africa. More than 1 million deaths per year occur worldwide as a result of AIDS. Various worldwide attempts to reduce infection and spreading rates of HIV, for example through massive safer sex education programs and free condom distribution points, have not significantly reduced infection rates and can be considered partially successful in reducing the spread of HIV worldwide. Prior art randomized controlled studies as well as epidemiological studies have shown that circumcision can significantly reduce the risk of infection with HIV in males. One possible explanation of the results of such studies is that the skin cells of which the foreskin is constructed have less protection to diseases and infections than skin cells on other parts of the body. Thus, the skin cells of the foreskin are more prone to diseases and infections which may be transmitted by sexual relations when the foreskin is stretched and its skin cells are revealed. Based on these studies, the World Health Organization (known as the WHO) and the Joint United Nations Programme on HIV/AIDS (known as UNAIDS) have published position papers substantially recommending large scale circumcision of adult males worldwide living in regions and amongst populations having higher rates of HIV infection, i.e., HIV at risk regions and populations. These position papers include "Male circumcision: Global trends and determinants of prevalence, safety and acceptability," published by the WHO and UNAIDS in 2007, ISBN 978 92 4 159616 9 (WHO), and "Male Circumcision and HIV Prevention: Research Implications for Policy and Programming—Conclusions and Recommendations," a WHO/UNAIDS Technical Consultation presented in Montreux, Switzerland, on Mar. 6-8, 2007. In addition, other large governmental bodies have put forth possible biological explanations linking circumcision to reduction in HIV infection rate. One such biological explanation can be found on the website of the U.S.'s Centers for Disease Control and Prevention, at http://www.cdc.gov/hiv/resources/factsheets/circumcision.htm. In particular, the published papers of the WHO and the UNAIDS cited research which showed that the risk for infection of HIV is lowered by 44%-71% in circumcised men. The WHO has thus recommended circumcision to be incorporated among the main strategic tools countries and healthcare authorities should consider in order to reduce the spread of HIV.

One traditional method for performing circumcision is by surgically removing the foreskin after physically pulling the foreskin over the glans. In such methods, the foreskin is removed while it is still a live tissue, usually causing bleeding. In some cases, due to religious considerations, blood may be drawn even if bleeding does not occur. Such methods may involve hemorrhaging and a relatively long period of healing of the incision (e.g., up to a few weeks), while inducing sustainable pain in an individual. In most cases suturing is required when such a procedure is performed on adult males. Such methods, referred to also as a mini-surgery, can incur substantial costs on an individual undergoing such a procedure as well as on organizations conducting circumcisions on a large scale (such as national public health ministries). In addition, when the above mentioned circumcision procedure is performed on a large scale (i.e., for a large number of individuals such as thousands of individuals), such mini-surgeries may require many resources, including trained surgical personnel, a clean and sterile surgery environment as well as the availability and administration of local anesthesia. Otherwise, serious side effects may be incurred on individuals undergoing such procedures. In general, such methods are recognized as not being scalable for mass circumcision campaigns, in particular in areas where medical facilities may be sparse or not available and where skilled personnel is scarce. It is therefore desirable to have a circumcision device that is scalable for mass circumcision and is also associated with as little pain as possible since perceptions of pain will substantially reduce the willingness (also known as the compliance level) of males to undergo circumcision.

Other methods and devices for performing circumcision are known in the art. Such methods may require anesthesia, sutures, skilled personnel, may not be bloodless and may not be scalable for mass circumcision campaigns. One such method for performing a circumcision is shown on the website http://www.circ-ring.de/us/circ ring english.html (owned by the company Circ-Ring International and known commercially as the Zhenxi Ring), which discloses a device for performing a circumcision by applying the foreskin to a ring, and then clutching the foreskin with a tight fastening portion. Other variants of this method are known and are described below. In such a manner, the foreskin is tightly compressed and blood is prevented from flowing therein. The fastening portion is an enclosing clamp fastened by a screw portion. Excess skin (i.e., the foreskin) is removed using a scalpel or another sharp implement. As the foreskin is tightly compressed when the ring is placed around the penis, a local anesthesia is substantially required when the fastening portion is fastened and tightened around the penis to reduce any feelings of pain the individual may experience in his penis while the device is placed on his penis. As the ring fits securely around the penis in a flaccid state, pain may be experienced by the individual during an erection, such as erections which may occur during sleep.

A similar device to the Zhenxi Ring is disclosed in PCT International Publication No. WO 2007/022730A1 (also known commercially as the ShangRing and available on the website www.snnda.com). The compression mechanism of this device as well as the cutting of the excess skin when it is deployed on a penis are likely to make the removal process of the device painful, typically requiring the application of local anesthesia during placement of and removal of the device, as well as other additional procedures such as soaking the area adjacent to the device in iodine prior to removal of the device. In addition, use of this device, which includes an inner ring, may involve pain while the device is on an individual's penis, such as during erections occurring in the individual while the individual is asleep. Pain associated with use of the ShangRing as well as mechanisms for dealing with such pain are discussed in the following journal articles: "Clinical application of a new device for minimally invasive circumcision" to Peng et al., published in the Asian Journal of Andrology 2008, 10(3), pp. 447-454 and "Adult Male Circumcision Using the Chinese Shang Ring: Results of 328 Cases and a Recommended Standard Surgical Protocol in China" to Cheng et al., published in the National Journal of Andrology (China) July 2009, 15(7), pp. 584-592. The Peng article suggests prescribing medication having anti-libido attributes, such as oral diethylstilbestrol, to prevent erections while an individual is asleep. The Cheng article suggests making small incisions along the edge of the foreskin on the underside of the ring to minimize pain during nocturnal erections. Such incisions could increase the risk of infection in live skin tissue. Both suggestions just mentioned involve pain and possible risks related to the ring being too tight in certain circumstances. In addition, part of the procedure of using the ring involves making incisions in tissue that is not dead. Such incisions may involve an amount of bleeding and could potentially lead to infections.

U.S. Pat. No. 4,491,136 issued to LeVeen and entitled "Disposable Circumcision Device," is directed to a device for performing circumcision. The device includes a male and a female member. The male member is a tubular support having an annular groove. The female member is a clamp or an elastic ring, adapted to fit over the annular groove. The foreskin is stretched over the male member. The female member is then applied over the annular groove, compressing the foreskin along the groove. This action traps the foreskin between the two members. The excess foreskin is then cut off and the male member is removed from beneath the ring of the female member, forcing the cut end of the foreskin to be prevented from bleeding. After the ends of the foreskin have healed, the female member and rings are removed in a few days time. The device of LeVeen enables the ends of the foreskin to heal after the excess foreskin is cut off, which reduces the need for suturing. At the same time, this device still involves a surgical procedure of excising the foreskin while it is still a live tissue. In addition, the mechanism of trapping the foreskin between the two members does not enable natural detachment of the foreskin, thereby possibly causing pain to the individual while the device is deployed, used and then removed.

U.S. Pat. No. 5,269,788 issued to Nelson, III, and entitled "Adjustable Hemostatic Circumcision Dressing and Method of its Use," is directed to a device for performing circumcision. The device includes an inner arcuate member having a pair of ends, an elongated hollow connector piece and an outer arcuate grooved member. The inner member is positioned between the prepuce and shaft of a penis parallel to the corona of the glans of the penis. The hollow connector piece receives the pair of ends of the inner member. The outer arcuate grooved member is positioned over and encompasses the prepuce (i.e., foreskin), when it is pulled up over the inner member. The groove is disposed about the inner periphery of the outer member. The inner member press-fits into the outer member groove when the members are brought into mating relationship, with the foreskin held there between. A crushing action is thereby exerted upon the foreskin, causing hemostasis. After the application of the outer member, the foreskin is excised with a sharp instrument such as a scalpel or scissors or with a surgical cautery. The inner and outer members, securely in position, act as both a line of sutures and a sterile dressing for the circumcision. Between the members, pressure necrosis and healing occur in the course of approximately two to three weeks. On a return visit to a physician, the outer and inner members are removed to reveal the healed circumcision. The device of Nelson, III, requires a surgical removal of the foreskin at the time the device is deployed. In general, an individual may feel pain when such a device is used unless anesthesia is applied to the area of the penis surrounding the foreskin. In addition, this device requires a sterile environment as well as surgical tools to excise the foreskin at the time the device is deployed. As the foreskin in this device is excised while still a live tissue, an increased risk is involved in healthy skin tissue being incorrectly excised.

U.S. Pat. No. 7,303,567 issued to Smith, and entitled "Circumcision Device," is directed to a device for performing a circumcision. The device includes a ring, a bridge and a handle. The ring has a tapered interior surface, an open anterior end, an anterior opening defined by the interior surface at the anterior end, an open posterior end and a posterior opening defined by the interior surface at the posterior end. The posterior opening is larger than the anterior opening. The ring also includes an exterior surface and a groove circumferentially defined around the exterior surface adjacent to the anterior end. The bridge extends over the anterior opening and is fixedly connected to the anterior end at circumferentially spaced points thereof. The handle is fixedly but frangibly connected to the bridge at a junction between the handle and the bridge. The handle extends longitudinally and outwardly from the junction, being structurally weaker adjacent to the junction than to any other portion of the handle. The handle is thus readily breakable and detachable from the bridge at the junction.

To use the device, a surgeon grasps the handle of the circumcision device and positions the ring over the glans. The foreskin is pulled distally over the ring, followed by the tying of a ligature around the foreskin so as to compress the foreskin into the groove of the ring. Excess foreskin distal to the ligature and adjacent to the anterior end of the ring is trimmed off with scissors or a scalpel. Finally, the handle is broken off and detached from the bridge, leaving the bridge connected to the ring and the flange. The glans now partially protrudes from the anterior end so that its tip is in contact with the inner surface of the bridge. The bridge therefore acts as an obstruction to the glans, thereby limiting its protrusion from anterior end. Protrusion is sufficiently limited so that after 3-8 days, the ring and attached bridge are allowed to fall off the penis once the foreskin under the ligature dies. As described above in other prior art devices, the device of Smith requires the foreskin to be excised when the device is used. In addition, the nature of the mechanism of Smith may make it impractical for large scale use, possibly causing reluctance among males to undergo the procedure of circumcision.

Other patents and patent applications for methods and devices for performing a circumcision include Chinese (CN) Patent Application Publication No. 101327144A, Chinese (CN) Patent No. 2048737 and U.S. Pat. Nos. 2,272,072, 2,561,176 and 5,649,933.

SUMMARY OF THE PRESENT DISCLOSED TECHNIQUE

It is an object of the disclosed technique to provide a novel method and system for circumcision a penis bloodlessly and painlessly without requiring the use of sutures or bandages which overcomes the disadvantages of the prior art. In accordance with the disclosed technique, there is thus provided a system for effecting ischemic necrosis in a foreskin of a penis. The system includes a rigid ring, at least one elastic ring and at least one circumferential groove. The rigid ring includes an inner surface, the inner surface including an inner diameter, and an outer surface, the outer surface including an outer diameter. The elastic ring is configured to substantially fit around a surface of the rigid ring. The circumferential groove is located on a surface of at least one of the rigid ring and the elastic ring. The inner diameter of the rigid ring is at least slightly larger than a diameter of a shaft of the penis and a diameter of the elastic ring in a relaxed state is at least substantially equal to the diameter of the shaft of the penis. The rigid ring is placed around a first surface of the foreskin and the elastic ring is placed around a second surface of the foreskin, with the foreskin being placed within the circumferential groove. The rigid ring and the elastic ring thereby compress the foreskin in the circumferential groove with a compression force, wherein the compression force is sufficient to effect ischemic necrosis in the foreskin.

According to another aspect of the disclosed technique, there is thus provided a system for effecting ischemic necrosis in a foreskin of a penis, including a semi-rigid ring, at least one elastic ring and at least one circumferential groove. The semi-rigid ring includes an inner surface, the inner surface including an inner diameter, and an outer surface, the outer surface including an outer diameter. The elastic ring is configured to substantially fit around a surface of the semi-rigid ring. The circumferential groove is located on a surface of at least one of the semi-rigid ring and the elastic ring. The inner diameter of the semi-rigid ring in a relaxed state is at least slightly larger than a diameter of a shaft of the penis and a diameter of the elastic ring in a relaxed state is at least substantially equal to the diameter of the shaft of the penis. The semi-rigid ring is placed around a first surface of the foreskin, the elastic ring is placed around a second surface of the foreskin and the foreskin is placed within the circumferential groove. The semi-rigid ring and the elastic ring thereby compress the foreskin in the circumferential groove with a compression force, wherein the compression force is sufficient to effect ischemic necrosis in the foreskin.

According to a further aspect of the disclosed technique, there is thus provided a holding system for deploying an elastic ring around a rigid ring. The holding system is hollow and includes at least three flanges, each one of the three flanges being substantially located around a circumference of the holding system. The holding system has a first convex polygonal shape and when the elastic ring is stretched around the three flanges, it forms a second polygon shape. The rigid ring includes an inner rigid ring surface and an outer rigid ring surface. The inner rigid ring surface includes an inner rigid ring diameter and the outer rigid ring surface includes an outer rigid ring diameter. The rigid ring is placed around a glans of a penis, between the glans and a foreskin of the penis.

According to another aspect of the disclosed technique, there is thus provided a system for removing foreskin tissue, the foreskin tissue being compressed between at least one elastic ring and a rigid ring. The foreskin tissue is necrotic above the elastic ring. The system includes a closed loop suture string, the closed loop suture string including a roughened section located along a portion of the closed loop suture string. A diameter of the closed loop suture string is at least slightly larger than an outer diameter of the rigid ring.

According to a further aspect of the disclosed technique, there is thus provided a system for removing foreskin tissue, the foreskin tissue being compressed between at least one inner ring and at least one outer ring, the foreskin tissue extending above and below the outer ring. The system includes at least two elements, a connector and at least one cutter. Each one of the two elements includes an inner surface and an outer surface. The connector is coupled with the two elements and the cutter is coupled with the inner surface of at least one of the two elements. The connector is for coupling the two elements. The connector is configured to position the two elements around the least one inner ring and the foreskin tissue. When the two elements are positioned around the inner ring and the foreskin tissue, the cutter is positioned above the outer ring, substantially touching the foreskin tissue above the outer ring.

According to another aspect of disclosed technique, there is thus provided a system for tracking a circumcision device, the circumcision device including at least two elements. The system includes a respective unique identification for each one of the at least two elements an identification entry device and a processor. Each respective unique identification is coupled with a respective one of the two elements and the processor is coupled with the identification entry device. The identification entry device is for entering the respective unique identification in the processor. The processor authenticates the two elements before the circumcision device is used on an individual.

According to a further aspect of the disclosed technique, there is thus provided a method for circumcising a foreskin of a penis. The method includes the procedures of positioning a ring element around a first surface of the foreskin, positioning at least one elastic ring around a second surface of the foreskin, thereby compressing the foreskin with a compression force and removing the foreskin once the foreskin is necrotic. The compression force is sufficient to effect ischemic necrosis in the foreskin and the compression force is applied until the foreskin is necrotic.

According to another aspect of the disclosed technique, there is thus provided a method for circumcising a foreskin of a penis. The method includes the procedures of positioning at least one inner ring around an inner surface of the foreskin, positioning at least one outer ring around an outer surface of the foreskin, thereby compressing the foreskin between the inner ring and the outer ring with a compression force and removing the foreskin once the foreskin is necrotic. The compression force is sufficient to effect ischemic necrosis in the foreskin and the compression force is applied until the foreskin is necrotic.

According to a further aspect of the disclosed technique, there is thus provided a method for tracking a circumcision device, the circumcision device including at least two elements. The method includes the procedures of coupling a respective unique identification to each one of the at least two elements, entering the respective unique identification a first time into a processor and entering the respective unique identification a second time into the processor. The first time is to authenticate each one of the two elements before each one of the two elements is used on an individual and the second time is after each one of the two elements is removed from the individual.

According to another aspect of the disclosed technique, there is thus provided a system effecting a full degeneration of a skin tissue. The system includes a first, generally cylindrical, hollow element and a second, preformed elastic element sized to fit on an outside of the cylinder in an expanded condition. The first hollow element has a minimal inner diameter sized to fit around a human penis in an erected state and having a minimal outer diameter small enough to allow folding of a human penis foreskin thereon. The preformed elastic element is sized and shaped and has an elastic coefficient suitable to apply a pressure of between 0.5 and 20 atmospheres, to tissue positioned between the elastic element and the first hollow element. The pressure enables a painless ischemic necrosis until a full degeneration of the tissue.

According to a further aspect of the disclosed technique, there is thus provided a method of imposing full ischemic degeneration to a foreskin portion. The method includes the procedures of providing a circumcision clamp system, deploying the circumcision clamp and removing the circumcision clamp over 72 hours after deployment. The circumcision clamp system includes an inner ring configured to press a first surface of a skin tissue and an outer ring clamp member configured to press a second surface opposing the first surface of the skin tissue. The foreskin portion in-between the inner and outer rings is compressed in a continuous local compression pressure between 0.5 to 15 atmospheres.

According to another aspect of the disclosed technique, there is thus provided a method for performing a non-surgical cosmetic procedure to remove a dead tissue portion attached to a foreskin. The method includes the procedures of providing a circular clamping device to circumferentially clamp the foreskin, providing a cutting device to anchor around the distal surface of the clamping device and moving the cutting device with respect to the clamping device, thereby dissecting the dead tissue portion from foreskin. The clamping device includes a distal surface having a first pattern and located above the dead tissue portion. The cutting device includes a surface having a second pattern mating the first pattern of the clamping device distal surface and at least one blade projected between the mating patterns.

BRIEF DESCRIPTION OF THE DRAWINGS

The disclosed technique will be understood and appreciated more fully from the following detailed description taken in conjunction with the drawings in which:

FIG. 1 is a schematic illustration of a bloodless circumcision device, constructed and operative in accordance with an embodiment of the disclosed technique;

FIG. 3 is a schematic illustration of another bloodless circumcision device, for accommodating a plurality of penis sizes, constructed and operative in accordance with a further embodiment of the disclosed technique;

FIG. 4 is a schematic illustration of a further bloodless circumcision device, for accommodating a plurality of penis sizes, constructed and operative in accordance with another embodiment of the disclosed technique;

FIG. 6 is a schematic illustration showing different types of capturing rings, constructed and operative in accordance with another embodiment of the disclosed technique;

FIGS. 7A-7H are schematic illustrations showing different shapes of capturing rings, constructed and operative in accordance with a further embodiment of the disclosed technique;

FIGS. 8A-8B are schematic illustrations showing different types of introducer shapes, constructed and operative in accordance with another embodiment of the disclosed technique;

FIGS. 10A-10B are schematic illustrations showing a capturing ring including a groove on its inner side, constructed and operative in accordance with a further embodiment of the disclosed technique;

FIGS. 10C-10D are schematic illustrations showing another capturing ring including an embossed section on its inner side, constructed and operative in accordance with another embodiment of the disclosed technique;

FIGS. 14A-14E are schematic illustrations of different inner ring shapes and configurations for use with a bloodless circumcision device, constructed and operative in accordance with another embodiment of the disclosed technique;

FIGS. 15A-15D are schematic illustrations showing different views of a foreskin cutter, constructed and operative in accordance with a further embodiment of the disclosed technique;

FIGS. 16A-16D are schematic illustrations showing different views of another foreskin cutter, constructed and operative in accordance with another embodiment of the disclosed technique;

FIGS. 19A-19K are schematic illustrations showing the method of use of the capturing ring deployment system of FIGS. 18A-18D with a bloodless circumcision device, constructed and operative in accordance with a further embodiment of the disclosed technique;

FIG. 20 is a schematic illustration of size selector for determining the appropriate size of a bloodless circumcision device to be used on an individual, constructed and operative in accordance with another embodiment of the disclosed technique;

FIGS. 22A-22G are schematic illustrations of other inner ring shapes and configurations for use with a bloodless circumcision device, constructed and operative in accordance with a further embodiment of the disclosed technique.

DETAILED DESCRIPTION OF THE EMBODIMENTS

Figure 2C:
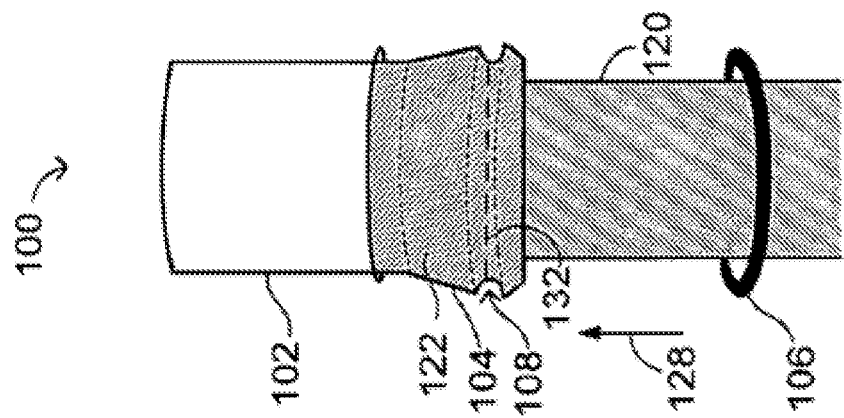
FIGS. 2A-2E are schematic illustrations showing the method of use of the circumcision device of FIG. 1, constructed and operative in accordance with another embodiment of the disclosed technique.

The disclosed technique overcomes the disadvantages of the prior art by providing a bloodless circumcision device, including an inner ring and a capturing ring, which are coupled together around the foreskin of a penis for causing controlled ischemic necrosis of the foreskin until the foreskin tissue degenerates, dehydrates or both. The bloodless circumcision device may also include a capturing ring deployment device, a removal device and optionally an introducer. The bloodless circumcision device is substantially painless and bloodless, allowing for a safe and precise detachment of the foreskin of the penis of a male individual once the foreskin has fully degenerated, dehydrated or both. It is noted that any references to individuals in the description of the disclosed technique refer to male individuals (i.e., infants, children, adolescents and adults). The inner ring, capturing ring or both may include a circumferential groove, or at least one recess, suited to tightly receive a portion of the foreskin. The capturing ring deployment device may be used to position the capturing ring on the inner ring accurately, thereby enabling the foreskin to be circumcised at a precise location. The capturing ring deployment device is used to hold the capturing ring in a stretched position, or a stretched form, before placement on the inner ring. The removal device is used to remove at least one of the capturing ring, the inner ring and a dead foreskin. The removal device can also prevent reuse of the bloodless circumcision device by rendering the bloodless circumcision device unusable. The introducer is a hollow elongated cylindrical element used to optionally position the inner ring on the penis of an individual. In some embodiments, the capturing ring can be an elastic ring, such as a rubber O-ring. The capturing ring and the inner ring may optionally have specific cross section shapes which increase the effectiveness of skin tissue degeneration and skin tissue self-detachment. The skin tissue of the foreskin is degenerated by uniformly compressing the foreskin between the inner ring, which may be rigid, semi-rigid, malleable, expandable, shrinkable or a combination of the aforementioned, and the capturing ring, which may be elastic. The compression of the foreskin eventually causes full necrosis of the foreskin which may then self-detach or be removed. The disclosed technique may be considered, fully or partially, a cosmetic non-surgical operation that only comprises the removal of dead tissue.

In some embodiments of the disclosed technique, the penis of an individual is circumcised bloodlessly by first pulling the foreskin of the penis down, away from the glans. The inner ring is then placed around the glans, optionally using the introducer and the foreskin is then pulled up over the inner ring. In other embodiments of the disclosed technique, the opening of the foreskin is stretched open and the inner ring is inserted through the opening of the foreskin around the glans of the penis. The inner ring is then maneuvered and positioned at a desired location around the glans. The inner ring is thus positioned between the inner surface of the foreskin and the glans of the penis. The capturing ring is then placed over the foreskin, substantially tightly fitting into the circumferential groove of the inner ring. The capturing ring is thus positioned around the outer surface of the foreskin. The capturing ring may be placed directly on the foreskin which is over the inner ring or may be placed on the foreskin which is over the inner ring with the aid of the capturing ring deployment device, leaving the foreskin compressed between the inner ring and the capturing ring. With the foreskin tightly compressed such that no blood reaches the skin tissue in the foreskin, controlled ischemic necrosis to the foreskin is caused. After a time period, usually a few minutes to a few hours, the cells in the skin tissue of the foreskin begin to die. Within a few days, for example after 72 hours or between 5-7 days, the skin tissue in the foreskin fully dehydrates and becomes hard and dry. At this point, the removal device can be used for excising the dead foreskin tissue from the live foreskin tissue still intact below the capturing ring in a substantially painless and bloodless manner. Alternatively, the foreskin either falls off along the circumference of the capturing ring naturally, or can easily be removed using any surgical or non-surgical cutting or peeling device such as an ordinary pair of scissors, a scalpel or a foreskin cutter, as described below, without any incision to live skin tissue and without any need for suturing. Once the foreskin has fallen off or has been removed, the inner ring can be removed manually or with the aid of a cutting device or the removal device. The shape and configuration of the inner ring and capturing ring enable consistent circumcision results to be achieved. Once the bloodless circumcision device has been removed from the individual, further suturing or bandaging is not needed. Therefore, the individual does not need any suturing or bandaging during or after the process of circumcision using the disclosed technique. As shown below, the disclosed technique does not necessitate highly skilled personnel and can be easily taught to individuals involved in a mass circumcision campaign.

As taught by the disclosed technique, the radial pressure caused by the compression of the capturing ring on the inner ring enables a painless and bloodless procedure for circumcision. The radial pressure is substantially high enough to stop blood circulation to the foreskin, thereby causing ischemic necrosis, preventing blood flow to the nerves in the foreskin and preventing dislodgment of the capturing ring from the inner ring during normal activity of the individual. At the same time, the radial pressure is not high enough to exert a crushing force on the foreskin which may cause pain to the individual. As an example, the radial pressure may vary between the ranges of 0.1-20 atmospheres. A specific range of compressive pressures may be set in order to allow for painless ischemic necrosis of the foreskin. For example, the specific range may be from 0.1-20 atmospheres, 0.5-15 atmospheres, 1.5-10 atmospheres or any combination thereof having higher, lower or intermediate values.

The disclosed technique also allows for cost effectiveness in a mass circumcision campaign, as the entire process of applying the bloodless circumcision device, removing the foreskin and removing the device from an individual can be done in any environment, even if not sterile and even without highly trained personnel. The disclosed technique only requires a minimal amount of training before use and application. The disclosed technique is thus cost efficient as compared with the costs of alternative methods for circumcision such as a typical mini-surgery. The disclosed technique further enables a safe and simple circumcision device. The dimensions of the capturing ring and the inner ring are selected such that damage is not caused to the penis if the penis becomes erect while the device is on an individual. In addition, no strings need to be attached or coupled to the foreskin surrounding the inner ring. Also, the circumcision device can be deployed and removed without use of anesthesia, either local or general. The circumcision device of the disclosed technique thus represents a simple and safe circumcision device which is completely bloodless, painless, does not require sutures, surgical cuts or incisions to skin tissue at the time of deployment or removal, can be easily removed without causing pain, or harm to the individual (even without anesthetics) and can be scaled to be used in a mass circumcision campaign.

It is noted that the term 'necrosis' substantially refers to tissue death, also known as gangrene. The term 'ischemia' refers to localized anemia (i.e., reduction in the number of red blood cells) in a portion of the body due to an obstruction. The term 'ischemic necrosis' therefore refers to tissue death caused by an obstruction which causes deprivation of the blood supply to the tissue. Ischemic necrosis can also refer to the process of tissue death caused by a continuous obstruction which causes deprivation of the blood supply to the tissue. It is also noted that the term 'hemostasis' refers the stoppage of bleeding. It is furthermore noted that the term 'degeneration' in medical usage refers to the deterioration of body tissue wherein the tissue changes from a higher to a lower or less functionally active form. Degeneration may also imply that the tissue undergoes an actual chemical change. When tissue has fully degenerated, the tissue can be considered dead or necrotic. During the process of degeneration, the tissue rots and eventually becomes dry and hard when most, if not all fluids in the tissue are absent.

In general, identical elements and components which appear in more than one figure are labeled using identical numbers. The dimensions of elements, components and features shown in the figures are not necessarily shown to scale and may be drawn for the purposes of clarity and convenience. Many of the figures presented are presented as schematic illustrations for explanatory purposes, and as such, certain elements and components may be substantially simplified and not drawn to scale. The figures are not intended to be production drawings.

Reference is now made to FIG. 1, which is a schematic illustration of a bloodless circumcision device, generally referenced 100, shown in a disassembled configuration, constructed and operative in accordance with an embodiment of the disclosed technique. Circumcision device 100 includes an introducer 102, an inner ring 104 and a capturing ring 106. Introducer 102 is an elongated hollow cylinder, suited to receive a penis. Introducer 102 is an optional element. The size of introducer 102 may be modified to receive different penis sizes. Inner ring 104 is a hollow cylinder, having a length smaller than that of introducer 102. Inner ring 104 may have a length, for example, of 2 centimeters. The inner diameter (not shown) of inner ring 104 is greater than the outer diameter of introducer 102, such that inner ring 104 may be fitted over introducer 102. Inner ring 104 includes a circumferential groove 108 on its outer side (not shown). The diameter of capturing ring 106 is such that it may tightly fit into circumferential groove 108 of inner ring 104. The inner surface of inner ring 104 (not shown) may be coated with, or made of a soft material, such as synthetic fleece, polyurethane latex or a soft silicone coating to ease placement of inner ring 104 over the penis of an individual and to reduce any potential pain or friction to the individual while inner ring 104 is properly positioned. Capturing ring 106 may be constructed of an elastic material such as rubber or silicone. Capturing ring 106 can also be manufactured from an elastic, super elastic, spring-like or distensible material, such as, but not limited to, silicon, polyurethane, stainless steel, Nitinol or any combination of such materials. Capturing ring 106 can further be manufactured from a shape memory alloy. Introducer 102 and inner ring 104 are typically constructed of a rigid material such as plastic. Introducer 102 and inner ring 104 can also be manufactured from a non-compressible, or minimally compressible biocompatible plastic material, such as, but not limited to, polycarbonate, silicon, silicone, polyether, polyethylene, polyurethane and the like. In addition, introducer 102 and inner ring 104 can also be manufactured from a biocompatible metal, such as, but not limited to, stainless steel. Furthermore, introducer 102 and inner ring 104 may be manufactured from a combination of a biocompatible plastic material and a biocompatible metal. Introducer 102, inner ring 104 and capturing ring 106 can be manufactured from biodegradable materials, such as polylactic acid (also known as PLA), or combinations of biodegradable materials, such as the polymers trimethylene carbonate (TMC), L-polylactic acid (LPLA), D,L-polylactic acid (DLPLA) and polyglycolic acid (PGA), which are commonly used in human implants. By manufacturing introducer 102, inner ring 104 and capturing ring 106 from biodegradable materials, any potential environmental impact from the use and disposal of bloodless circumcision device 100 can be minimized over time. It is noted that whereas the described embodiments of the bloodless circumcision device of the disclosed technique, including inner ring 104 and capturing ring 106, are designed to be single use devices to reduce the likelihood of cross infection, the elements of the disclosed technique may be manufactured from materials which can be recycled after use. In general, any surface on introducer 102 and inner ring 104 which comes in contact with the skin tissue of the foreskin should be soft and resilient. Circumferential groove 108 on the other hand, should be rigid and non-resilient.

It is noted that the inner diameter of inner ring 104 is equal to or larger than the diameter of the penis (not shown) over which it is placed when the penis is erect, thereby leaving sufficient space for penis erections without applying pressure on the penis itself when bloodless circumcision device 100 is used on the penis. For example, inner ring 104 may have a diameter which is 1 centimeter larger than the diameter of the shaft of the penis over which inner ring 104 is placed when the penis is flaccid. As another example, inner ring 104 may have a diameter which is the same or larger than the diameter of the shaft of the penis over which inner ring 104 is placed when the penis is erect. In another embodiment of bloodless circumcision device 100, the inner diameter of inner ring 104 as well as the inner diameter of capturing ring 106 may be smaller than the diameter of the glans penis over which they are placed and are placed in front of the glans penis in this case.

The diameter (not shown) of capturing ring 106, when not stretched, is generally smaller than the diameter (not shown) of the inner side (not shown) of inner ring 104. For example, the diameter of capturing ring 106 may be smaller than the diameter of the inner side of inner ring 104, or the diameter of circumferential groove 108, by 1-10 millimeters (herein abbreviated mm) In addition, the diameter of capturing ring 106, when not stretched, is generally larger than the widest point of the penis shaft (not shown) on which it is placed by at least 3 mm. In another embodiment, the diameter of capturing ring 106, when not stretched, is substantially equal to or larger than the diameter of the shaft of the penis when the penis is flaccid, measured from the sulcus at the base of the glans penis. The smaller diameter of capturing ring 106 as compared to the diameter of inner ring 104 is what produces pressure on the foreskin (not shown) in an inward radial direction, eventually leading to necrosis of the foreskin, as described below in FIGS. 2A-2E. The relative diameter of capturing ring 106 to inner ring 104, the penis shaft and the glans of the penis (both not shown) is significant for safety reasons, since if capturing ring 106 slips off inner ring 104, it will not apply pressure to the penis shaft or the glans of the penis, even if the penis is erect.

In general, capturing ring 106 is elastic in nature and when placed over a foreskin on inner ring 104, generates an inward radial pressure that is higher than the blood pressure in the blood vessels in the foreskin. As mentioned above, this inward radial pressure leads to necrosis of the foreskin. Also, as mentioned above, this inward radial pressure is not so high as to crush the blood vessels in the foreskin which may lead to a sensation of pain in the foreskin and to the individual using circumcision device 100. In addition, the pressure exerted by capturing ring 106 on inner ring 104 should be high enough to prevent the dislodgement of capturing ring 106 from circumferential groove 108, or the displacement of inner ring 104 during normal activity of the individual, including penis erections of the individual. In general, the minimal inward radial pressure required to cause ischemic necrosis of the foreskin can substantially be between 0.05 and 0.13 atmospheres, depending on the thickness, shape and size of an individual's foreskin as well as on anatomical and physiological parameters of the individual. Therefore the inward radial pressure of capturing ring 106 on the foreskin should be at least 0.05 atmospheres (which is approximately equal to 40 millimeters of mercury (mm Hg)). In general, the minimal inward radial pressure required to prevent capturing ring 106 from possibly dislodging from circumferential groove 108, for example during erections of the penis, can substantially be between 0.1 and 0.5 atmospheres, or possibly higher, such as at least 1 atmosphere or at least 2 atmospheres, again depending on anatomical and physiological parameters of the individual, such as the thickness, shape and size of the individual's foreskin. Alternatively therefore, the inward radial pressure of capturing ring 106 on the foreskin should be at least 0.1 atmospheres or greater, which will generally prevent the dislodgement of capturing ring 106 from circumferential groove 108, for example during erections of the penis. In general, a minimal inward radial pressure of approximately 3 to 20 atmospheres or more, may crush the blood vessels in the foreskin, thereby causing sensations of pain in the foreskin, irregardless of psychological aspects of pain relating to the individual. Therefore, the inward radial pressure of capturing ring 106 on the foreskin should be no more than 20 atmospheres to avoid inducing pain in the individual. In summary, the inward radial pressure, or compression force, of capturing ring 106 on the foreskin should be minimally 0.1 atmospheres and maximally 20 atmospheres, depending on anatomical and psychological parameters of the individual. The ranges of possible compression forces for the capturing ring of the disclosed technique on the foreskin is a matter of design choice and could range, for example, from 0.1-20 atmospheres, 0.5-10 atmospheres, 1-5 atmospheres or 1.5-3 atmospheres.

Given the range of inward radial pressures, the elasticity of capturing ring 106 should be selected to result in such a pressure range when it is stretched by a few millimeters (representing, for example, an increase in the length of capturing ring 106 by between 2.5%-20% of its length when not stretched). Thus depending on the material from which capturing ring 106 is constructed as well as its thickness, a small increase in its diameter when stretched may generate the above mentioned pressures. For example, such pressures may be achieved by increasing the diameter of capturing ring 106 when stretched from 0.1-5 millimeters dependent on the pressure considerations relating to capturing ring 106 mentioned above. Furthermore, if capturing ring 106 is made from a shape memory alloy, then capturing ring 106 may have two states, a larger diameter state when the temperature of capturing ring 106 is relatively cool and a smaller diameter state when the temperature of capturing ring 106 is relatively hot. In the larger diameter state, capturing ring 106 may have a diameter that is larger than the diameter of the penis. When capturing ring 106 is placed around a penis, it is placed when it is relatively cool. As body heat of the individual in the area of the penis heats up capturing ring 106, the diameter of capturing ring 106 shrinks to its diameter in the smaller diameter state. The diameter of capturing ring 106 when capturing ring 106 is in the smaller diameter state should be selected taking into consideration the above stated pressure requirements. In addition, the material, thickness and diameter of capturing ring 106 needs to be selected and determined while taking into consideration the above stated pressure requirements. One example of such a capturing ring would be a capturing ring made from EPDM rubber, having a thickness ranging from 1.5-3.5 mm, with a diameter ranging from 20-40 mm. The pressure of such a capturing ring on an inner ring can be between 0.5-20 atmospheres which is at least one order of magnitude higher than the pressure necessary for inducing necrosis of the foreskin. Table 1 below shows a few examples of possible dimensions for inner ring 104 and capturing ring 106 as well as the inward radial pressure exerted on a foreskin when compressed by capturing ring 106 and inner ring 104.

TABLE 1

Example Capturing Ring and Inner Ring Dimensions and Inward Radial Pressure

| Capturing Ring Inner Diameter (cm) | Capturing Ring Thickness (cm) | Inner Ring Outer Diameter (cm) | Pressure (atm) |
|---|---|---|---|
| 2.347 | 0.266 | 2.76 | 0.60 |
| 2.507 | 0.266 | 2.96 | 0.68 |
| 2.665 | 0.266 | 3.16 | 0.58 |
| 2.825 | 0.266 | 3.36 | 0.53 |
| 3.142 | 0.266 | 3.60 | 0.61 |

Figure 2B:
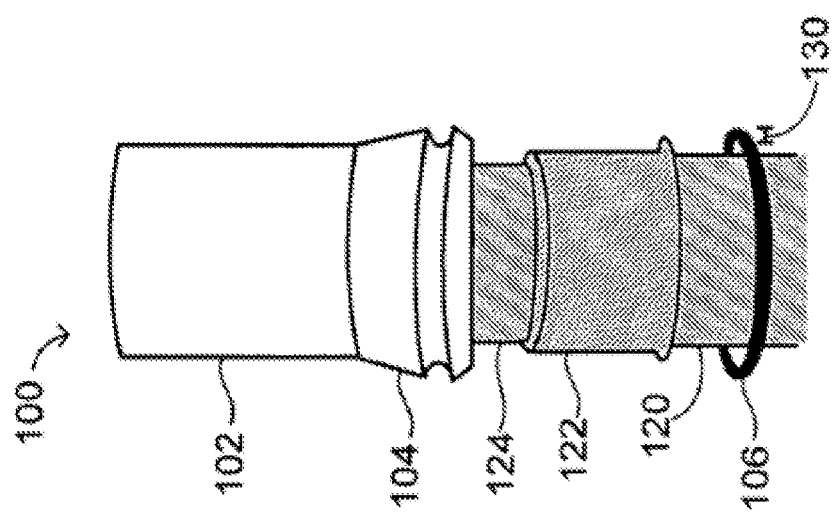
Figure 2A:
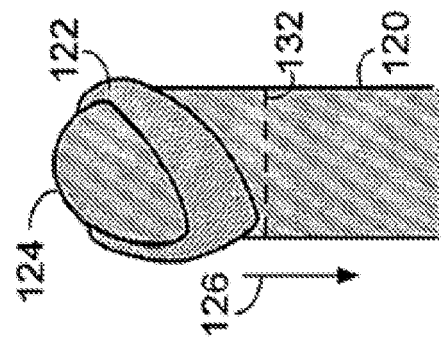
Figure 2E:
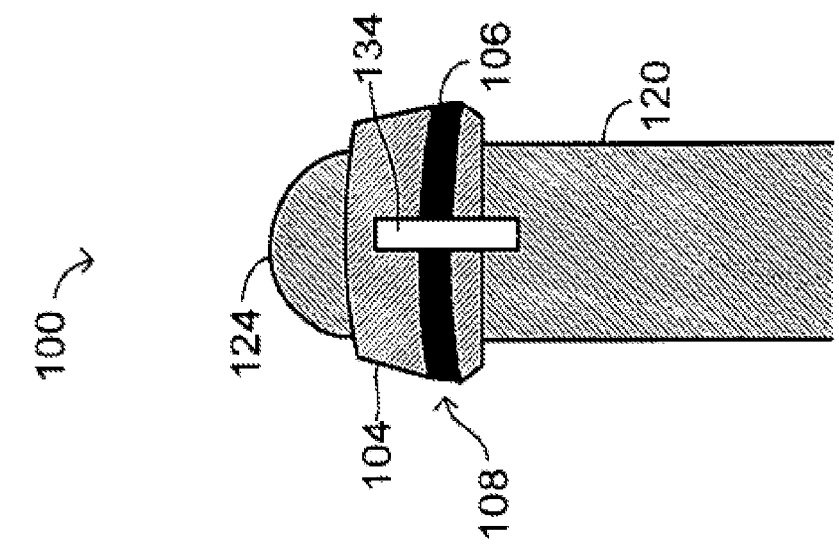
Figure 2D:
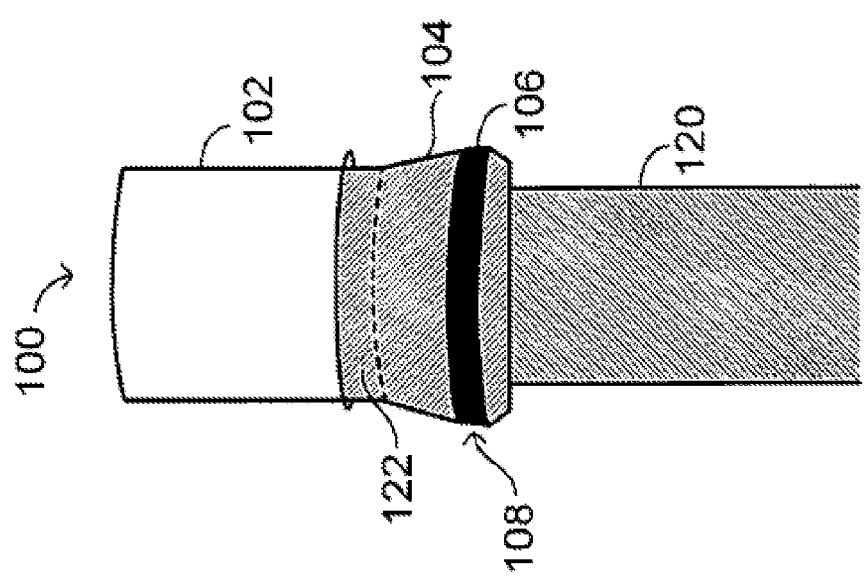

Reference is now made to FIGS. 2A-2E, which are schematic illustrations showing the method of use of the bloodless circumcision device of FIG. 1 on a penis, constructed and operative in accordance with another embodiment of the disclosed technique. FIGS. 2A-2E show the various steps of using the bloodless circumcision device of FIG. 1, each step demonstrating how the bloodless circumcision device is applied to the penis of an individual to circumcise the individual. FIG. 2A is a schematic illustration of a first step of the application of the bloodless circumcision device of FIG. 1. FIG. 2B is a schematic illustration of a second step of the application of the bloodless circumcision device of FIG. 1. FIG. 2C is a schematic illustration of a third step of the application of the bloodless circumcision device of FIG. 1. FIG. 2D is a schematic illustration of a fourth step of the application of the bloodless circumcision device of FIG. 1. And FIG. 2E is a schematic illustration of a fifth step of the application of the bloodless circumcision device of FIG. 1.

With reference to FIG. 2A, a penis 120 includes a glans 124 and a foreskin 122. In this first step, which is a preliminary step before the bloodless circumcision device is applied to penis 120, foreskin 122 is pulled down, away from glans 124, in a direction indicated by an arrow 126. The pulling of foreskin 122 exposes glans 124, which is normally covered by foreskin 122 in not erect uncircumcised males. Optionally, in the first step shown in FIG. 2A, a line, such as a dotted line 132, can be marked, using for example an erasable marker, on the shaft of the penis at the location where the individual desires to have foreskin 122 removed. If dotted line 132 is initially marked, then when foreskin 122 is pulled down, dotted line 132 becomes covered by foreskin 122. In an alternative to the first step, the opening (not shown) of foreskin 122 can be stretched open, either manually with the hands or with an instrument. With reference to FIG. 2B, in the second step of the application of the bloodless circumcision device, the various parts of bloodless circumcision device 100 (FIG. 1) are placed over penis 120. First, capturing ring 106 (FIG. 1) is placed over the shaft of penis 120 behind glans 124. Inner ring 104 (FIG. 1) is then placed over introducer 102 (FIG. 1), which in turn is placed over glans 124 and positioned over the shaft of penis 120 below the corona (not shown) of glans 124. The corona of glans 124 refers to the area of penis 120 where the shaft of penis 120 and glans 124 intersect. A sulcus (not shown), which forms part of the corona of glans 124, substantially separates the bottom of glans 124 from the shaft of penis 120. It is noted, however, that introducer 102 may be eliminated from the process if inner ring 104 is placed directly below glans 124. Capturing ring 106 has a width shown by a line 130. As shown in FIG. 2B, dotted line 132 is not visible. In an alternative to the second step, capturing ring 106 is placed over the shaft of penis 120 behind glans 124 and inner ring 104 is inserted vertically through the stretched open opening of foreskin 122, between foreskin 122 and glans 124. Inner ring 104 is then placed horizontally around glans 124. With reference to FIG. 2C, in the third step of the application of the bloodless circumcision device, foreskin 122 is pulled over inner ring 104, including circumferential groove 108 (FIG. 1), over glans 124. Foreskin 122 can be pulled in the direction indicated by an arrow 128 and extended as much as needed, thereby lining up dotted line 132 (i.e., the marked circumcision line) with circumferential groove 108 of inner ring 104. In this manner, the amount of foreskin to be removed can be adjusted according to the preference of an individual. If dotted line 132 was marked on the shaft of the penis in the first step, then when foreskin 122 is pulled up over inner ring 104, dotted line 132 can be aligned with circumferential groove 108 such that capturing ring 106 is placed on the shaft of penis 120 over the location where the individual desires to have foreskin 122 removed. In an alternative to the third step, inner ring 104 is maneuvered around glans 124 and foreskin 122 is adjusted such that inner ring 104 is placed at the desired location of the circumcision. With reference to FIG. 2D, in the fourth step of the application of the bloodless circumcision device, capturing ring 106 is placed over foreskin 122 at dotted line 132 (i.e., over inner ring 104), tightly fitting into circumferential groove 108 of inner ring 104. In this position, capturing ring 106 and inner ring 104 tightly compresses foreskin 122 along circumferential groove 108. If dotted line 132 was marked on the shaft of the penis in the first step, then when capturing ring 106 is placed in circumferential groove 108 in the fourth step, dotted line 132 is covered by capturing ring 106.

With reference to FIG. 2E, in the fifth step of the application of the bloodless circumcision device, introducer 102 is removed leaving inner ring 104 and capturing ring 106 on penis 120. Optionally in the fifth step, a single piece of medical grade adhesive tape 134 can be placed over the upper (i.e., the section of foreskin 122 to be removed which is above capturing ring 106) and lower (i.e., the section of foreskin 122 which is below capturing ring 106) sections of foreskin 122, thereby covering a portion of capturing ring 106, to prevent the individual from moving or repositioning capturing ring 106. As shown, all an individual sees once bloodless circumcision device 100 has been applied is capturing ring 106, which may have a width of approximately 1-4 millimeters, since inner ring 104 is covered by foreskin 122. The application of bloodless circumcision device 100 thus enables the individual to carry on with his daily routine without any interruption or disturbance caused by a device placed around a portion of his penis. In addition, as mentioned above in FIG. 1, since the diameter of inner ring 104 is equal to or larger than the diameter of penis 120 when penis 120 is erect, the application of bloodless circumcision device 100 minimizes the likelihood of harm to the shaft of penis 120, pain an individual using bloodless circumcision device 100 may feel if his penis becomes erect while using the device, or both. According to the disclosed technique, bloodless circumcision device 100 is left on penis 120 until foreskin 122 dies. Typically, ischemic necrosis of the foreskin will cause full foreskin death after a minimum of at least 72 hours. Therefore bloodless circumcision device 100 is left on penis 120 for a minimum of at least 72 hours.

It is also noted that according to the disclosed technique, the foreskin of a penis can be circumcised bloodlessly without requiring bandaging or suturing by compressing the foreskin between two closed hollow surfaces, at least one of which is rigid, at a compression force sufficient to cause ischemic necrosis of the foreskin. According to the disclosed technique, the compression force should be applied to the foreskin until the foreskin is dead and dry, i.e., until the foreskin tissue is fully necrotic. At this point, the dead and dry foreskin tissue can be removed, thereby circumcising the penis. For example, according to the disclosed technique, a prior art circumcision device can be used to apply a compression force around the foreskin high enough to cause ischemic necrosis. Such a prior art circumcision device is then left on the penis, compressing the foreskin, until full necrosis is effected on the foreskin, usually a few days after the device is placed on the individual. The necrotic foreskin is then removed from the individual before the device is removed from his penis.

In one embodiment of the disclosed technique capturing ring 106 is provided with a string, such as a suture string, for removing the capturing ring (and subsequently inner ring 104 if desired) before foreskin 122 falls off or is removed, if bloodless circumcision device 100 has to be removed. The string forms a closed loop around capturing ring 106. This is shown below in FIG. 7G. For example, if an incorrect size bloodless circumcision device was placed on an individual, capturing ring 106 from the bloodless circumcision device can be removed by simply pulling on the string. Such an embodiment enables the individual using bloodless circumcision device 100 to remove capturing ring 106 by themselves. According to another embodiment of the disclosed technique, capturing ring 106 can include at least one hole for inserting a removal device for removing capturing ring 106 before foreskin 122 falls off or is removed. The removal device may be a string which can be threaded through the at least one hole or a tool designed to firmly couple with the at least one hole in capturing ring 106 for removing capturing ring 106. Such an embodiment does not easily enable the individual using bloodless circumcision device 100 to remove capturing ring 106 by themselves and may require the individual to go to a trained personnel to have capturing ring 106 removed. This embodiment enables the use of bloodless circumcision device 100 to be more controlled and supervised by a trained personnel as capturing ring 106 cannot be easily removed by the individual using the device. An example of this is shown below in FIG. 7H.

Capturing ring 106 and inner ring 104 tightly compress foreskin 122 such that no blood reaches the foreskin tissue, causing controlled ischemic necrosis to foreskin 122. As mentioned above, the pressure exerted by capturing ring 106 on foreskin 122 is higher than the capillary pressure exerted by the blood vessels in foreskin 122, thereby causing the controlled ischemic necrosis of foreskin 122. The pressure exerted by capturing ring 106 on foreskin 122 should be higher than approximately 0.05 atmospheres, although a preliminary check may be used to determine a minimal individual specific pressure to be exerted by capturing ring 106 on foreskin 122 to cause ischemic necrosis of foreskin 122 of the individual. In one embodiment of the disclosed technique, substantially higher pressures can be used to firmly couple capturing ring 106 to inner ring 104 or to circumferential groove 108 and to avoid undesired dislodgment of capturing ring 106 from inner ring 104 or circumferential groove 108. For example, the pressure exerted by capturing ring 106 may be greater than 0.5 atmospheres or greater than 1 atmosphere. In addition, capturing ring 106 and inner ring 104 obstruct the blood supply to nerves around the area of foreskin 122, thereby reducing or eliminating any notion of pain or other sensations an individual may feel in the area on penis 120 where the bloodless circumcision device is placed. After a period usually lasting a few hours, the tissue in the foreskin begin to degenerate due to necrosis and within a few days is fully necrotic, degenerated and completely dry. The tissue of the foreskin may fall off or self-detach naturally, or may be removed using a foreskin cutter along the circumference of capturing ring 106. Foreskin 122 may fall off, or be removed, without an incision and no blood may be present during the entire process. Due to necrosis, the tissue connecting foreskin 122 to penis 120, also referred to as the circumcision line, heals autonomously, thereby eliminating the need for sutures of the tissue. In addition, since the tissue around the circumcision line fully degenerates, the tissue does not undergo a healing process. After foreskin 122 is separated from penis 120, inner ring 104 and capturing ring 106 may be removed from penis 120, which is now circumcised.

It is noted that in the case of a small diameter capturing ring (not shown), small as compared to the size of a respective inner ring (not shown), being placed on foreskin 122, the pressure exerted by the capturing ring may be significantly higher then the capillary pressure of the blood vessels in foreskin 122. At such a pressure, the capturing ring may begin cutting through the necrotic tissue of foreskin 122, possibly detaching foreskin 122 from penis 120 before foreskin 122 is fully necrotic and dry. This detachment of the foreskin may occur after a day, a few days or even after a number of hours after the placement of capturing ring 106 on foreskin 122, depending on the pressure exerted by capturing ring 106 on foreskin 122. Early detachment of the foreskin before the circumcision line has fully dehydrated may result in a skin dehiscence at the circumcision line due to weak skin tissue. Such a skin dehiscence may occur when the penis is under increased tension such as during an erection. Such a skin dehiscence may result in bleeding, infections and prolonged healing due to secondary infections. In order to reinforce the skin tissue at the circumcision line, according to one embodiment of the disclosed technique, a biological glue (such as medical grade n-butyl cyanoacrylate, medical grade octyl-cyanoacrylate or medical grade flexible collodion, a combination of such glues or any other known biocompatible glues, biologic glues, adhesion tapes, such as Tegaderm, or adhesive tapes) is applied to the area of the circumcision after the removal of the inner ring (not shown). Such a biological "instant adhesive" glue may be applied to the area on penis 120 where foreskin 122 fell off (herein referred to as the circumcision area), to avoid any breakage or tearing of the skin tissue around the circumcision area before complete healing of the circumcision area occurs. In addition, right after capturing ring 106 is placed over foreskin 122 and inner ring 104, an adhesive tape or biocompatible glue may be applied over capturing ring 106 and foreskin 122. The adhesive tape or biocompatible glue may be treated with at least one of an anti-inflammatory substance, antibiotics and an anesthetic substance. In the case of an adhesive tape, it may be left until foreskin 122 is detached or it may be changed periodically, such as once a day, once every other day and so on. It is noted that in certain circumstances, inner ring 104 may be removed before foreskin 122 has become fully necrotic and dry. At this stage, the inner surface (not shown) of the foreskin, the surface of the corona of the glans of the penis (not show) or both may adhere to inner ring 104, possibly causing pain or bleeding to the individual if the inner ring is removed. This pain or bleeding can be substantially prevented in such circumstances by manufacturing the inner and outer surfaces of inner ring 104 to have a smooth surface or by coating them with an anti-adhesive material in order to prevent tissue adhesion of the penis to the inner ring.

In the embodiment of the disclosed technique in which inner ring 104 and capturing ring 106 are both smaller in diameter than glans 124, the following alternative steps are followed for applying bloodless circumcision device 100 to penis 120. In a first step (not shown) inner ring 104 is pushed into the opening of foreskin 122 over glans 124. In this step, inner ring 104 is pushed far enough over glans 124 such that the urinary meatus (opening on penis 120 from which urine is released—not shown) is exposed and pressure is not exerted on the urethra (not shown). In addition, inner ring 104 may include a soft backing on its inner side (not shown), such as a soft silicone, thereby preventing the exertion of pressure on glans 124 by the portion of inner ring 104 which is in contact with glans 124. In a second step (not shown) foreskin 122 is pulled and stretched over inner ring 104. In a third step (not shown), capturing ring 106 is pushed over foreskin 122 until it fits securely over inner ring 104 and until it fits into circumferential groove 108, such that a compression force is exerted on foreskin 122 between inner ring 104 and capturing ring 106, stopping the blood supply to foreskin 122. After a period usually lasting a few hours, the tissue in the foreskin dies due to ischemic necrosis and within a few days falls off, or can be removed, along the circumference of capturing ring 106. It is noted that in this embodiment, the opening of inner ring 104 permits the passage of urine until foreskin 122 detaches. In addition, in this embodiment, since inner ring 104 is pushed up against the tip of glans 124 but is not placed over the shaft of penis 120, the likelihood of pain experienced by an individual using the device during an erection is minimized.

It is noted that the inner surface of inner ring 104 may be fabricated from a soft material such that contact of inner ring 104 with glans 124 will not exert significant pressure on glans 124 during erections and will not cause pain to penis 120 during erections. Alternatively, inner ring 104 may be manufactured from a flexible and minimally compressible material such as polyethylene, polyurethane or silicone, as mentioned above. In such a case inner ring 104 may be deformed in order to introduce it through the opening of foreskin 122 (not shown). Such an inner ring is relevant in the case when penis 120 suffers from phimosis. After being deformed and placed around glans 124, due to its elastic nature inner ring 104 will resume its circular shape and will be positioned behind the corona of glans 124 under foreskin 122. Afterwards, capturing ring 106 can be applied over foreskin 122, with capturing ring 106 being placed in circumferential groove 108.

According to a further embodiment of the disclosed technique, capturing ring 106 is manufactured from a material having a distensibility coefficient as well as a specified thickness such that the pressure exerted by capturing ring 106 is sufficient to cause necrosis to foreskin 122 or is sufficient to cut through the necrotic skin tissue (i.e., fully degenerated skin tissue) of foreskin 122 but is not sufficient enough to cause injury to the shaft of penis 120, for example in the case that capturing ring 106 inadvertently slips off of inner ring 104. According to the disclosed technique, the diameter of capturing ring 106 when not stretched over foreskin 122 and inner ring 104 should be equal to or larger than the diameter of the shaft of penis 120 (i.e., behind glans 124) when penis 120 is flaccid yet smaller than the diameter of circumferential groove 108 of inner ring 104. For example, the diameter of capturing ring 106 can be between 1-10 millimeters smaller than the diameter of circumferential groove 108 of inner ring 104.

It is noted that in another embodiment of the disclosed technique, capturing ring 106 may be made of a solid and rigid material, having a fixed diameter and inner ring 104 may be made of an elastic or distensible material. In such an embodiment, the following alternative steps are followed for applying bloodless circumcision device 100 to penis 120. In a first step (not shown), foreskin 122 is pulled down in the direction of arrow 126. This step is similar to what is shown in FIG. 2A.

In a second step (not shown), capturing ring 106 is placed on the shaft of penis 120, over foreskin 122 and inner ring 104 is placed behind glans 124. Introducer 102 may be used to properly position inner ring 104 over glans 124. This step is similar to what is shown in FIG. 2B. In a third step (not shown), inner ring 104 is compressed around glans 124, thereby reducing its diameter, while foreskin 122 is pulled up over inner ring 104. In a fourth step (not shown), while inner ring 104 is still compressed and after foreskin 122 has been pulled up, capturing ring 106 is placed in line with circumferential groove 108, and the compression force on inner ring 104 is released. As the compression force is released, inner ring 104 expands to its initial diameter such that a uniform radial force is exerted on foreskin 122 by inner ring 104 in the radial direction of capturing ring 106, thus stopping the blood supply to foreskin 122. Foreskin 122 is thus compressed against capturing ring 106, which is rigid and solid having a fixed diameter. After a period usually lasting a few hours, the tissue in the foreskin begins to die due to ischemic necrosis and within a few days is completely necrotic. The tissue in the foreskin may then fall off, or can easily be removed, along the circumference of capturing ring 106. It is noted that in this embodiment, capturing ring 106 may include a groove on its inner side (not shown), or a circumferential embossed section on its inner side (also not shown), on which inner ring 104 exerts an outward radial compression force on foreskin 122. These types of capturing rings are shown and described below in FIGS. 10A-10D.

It is also noted that inner ring 104 and capturing ring 106 may be covered by various ointments, creams, medications or other ingredients to enhance the circumcision process of bloodless circumcision device 100. For example, inner ring 104 and capturing ring 106 may be covered by a medicated ointment to enhance faster and smoother healing of the skin tissue when foreskin 122 detaches from penis 120. Such ointments may be placed on inner ring 104 and capturing ring 106 by dipping them in such ointments. As another example, inner ring 104 and capturing ring 106 may be covered by an ointment to prevent bacterial growth (such as Ambipor or polydimethylsiloxane, also known as dimethicone), to reduce inflammation, to cure an infection or to relieve or reduce pain at the boundary line on penis 120 where foreskin 122 is detached. In addition, inner ring 104 and capturing ring 106 may be fabricated of a porous plastic material which can include the antibacterial ointments mentioned above as well as alcohol. Also, inner ring 104 and capturing ring 106 may be fabricated from a porous plastic material embedded with other compounds such as copper-based antimicrobial fibers (for example, fibers sold by the company Cupron). Silver and silane-based antimicrobial additives (for example, silver-based products made by the company AcryMed) could also be embedded or coated on inner ring 104 and capturing ring 106. Inner ring 104 and capturing ring 106 may be dipped in such ointments before being applied to penis 120. Furthermore, inner ring 104 and capturing ring 106 may be embedded or injected with such ointments such that they release slowly when placed on penis 120. In addition, materials known to expedite the rate of necrosis, the rate at which skin dies or the rate at which dead skin tissue dries up can be embedded in inner ring 104 and capturing ring 106 by way of injection. In another embodiment, inner ring 104 and capturing ring 106 can be coated with such materials. Such materials can include silver, which is known to those skilled in the art as an antiseptic. Also, inner ring 104, capturing ring 106 or both can be coated or embedded with alcohol which may aid in drying up glans 124 and expediting the healing process of penis 120. As noted, inner ring 104 and capturing ring 106 can also be made of plastics which possess drug-eluting compounds or drug-eluting coatings. As such compounds and coatings are eventually fully released from inner ring 104 and capturing ring 106, inner ring 104 and capturing ring 106 can also be made of medical polymers having intrinsically antimicrobial side groups which remain on the surface of inner ring 104 and capturing 106. Such medical polymers are known to those skilled in the art (see for example the referenced report of the 2008 Eighth World Biomaterials Congress in Amsterdam, The Netherlands, at http://www.omnexus.com/resources/editorials.aspx?id=22117). Numerous grades of acetal copolymers including inorganic antimicrobial additives are available, such as Anti-Crobe from the company Ticona. Since these antimicrobial additives are distributed evenly throughout these materials they are claimed to not abrade or scratch off from the surface of such materials as do antimicrobial coatings.

Furthermore, it is noted that inner ring 104 and capturing ring 106 may be embedded with or covered with microelectronic devices to enable fast healing and to reduce the likelihood of an edema forming at the circumcision area once foreskin 122 falls off or is removed. An example of such a device includes the ActiPatch, sold by BioElectronics Corporation. Inner ring 104, capturing ring 106, or both may also be embedded with a transcutaneous electrical nerve stimulator, also known as a TENS unit, for transmitting electrical signals to the circumcision area for relieving pain electronically. In addition, or as an alternative to the TENS unit, a micro vibrator could be embedded in inner ring 104, capturing ring 106 or both to provide the user of bloodless circumcision device 100 (FIG. 1) with a pleasure mechanism while he cannot, or is advised not to have sexual intercourse while waiting for his foreskin to fall off and for his penis to heal. Inner ring 104, capturing ring 106, or both may furthermore be coated with known biodegradable polymers used in site-specific drug delivery devices and methods. Inner ring 104, capturing ring 106, or both may also be fabricated from such known biodegradable polymers used in site-specific drug delivery devices and methods. Examples of such are available from SurModics, such as their Eureka SOLO biodegradable coating. In other embodiments of the disclosed technique, inner ring 104, capturing ring 106, or both may be embedded with known drug delivery systems for the controlled release of therapeutic proteins to the circumcision area. For example, when inner ring 104 is placed on penis 120, therapeutic proteins to the circumcision area may be released by inner ring 104 according to a fully controlled drug release profile. An example of such a system is the OctoDEX drug delivery system, sold by OctoPlus. Bloodless circumcision device 100 may be fabricated in a variety of colors or patterns.

It is also noted that bloodless circumcision device 100 may include a unique identification, such as a barcode, a number, a code in an embedded radio frequency identification (herein abbreviated RFID) tag and the like on bloodless circumcision device 100. The unique identification may be used by an individual for follow-up, verification and tracking purposes, either by phone or over the Internet. For example, the unique identification may be given to the individual by the personnel, such as the healthcare personnel, deploying the bloodless circumcision device on the individual. The unique identification may also be on the bloodless circumcision device itself. The individual may then be able to call a data center, or access a data center website, to report pain, swelling or other side effects, on a periodic basis, resulting from use of the bloodless circumcision device. Such a data center or data center website can also function as a circumcision registry, similar to immunization registries that are known in the art and are commonly used. In some embodiments of the disclosed technique, inner ring 104, capturing ring 106, or both may be embedded with an RFID tag, a barcode, or both, for medical authentication, verification and supply chain optimization or both. Authentication can include determining if a medical device is legit (and not counterfeit) as well as determining if a medical is still valid to be used (or has expired). Such an addition to inner ring 104 and capturing 106 can aid in reducing the likelihood of their reuse as well as enabling improved monitoring of compliance to directives in large scale circumcision campaigns. In this embodiment, inner ring 104, capturing ring 106, or both can be tracked and monitored from the location where and time when they are fabricated to the location where and time when they are used on an individual. Such RFID tags are known and are available, for example, from the company 3M. RFID tags may also be used in inner ring 104, capturing ring 106, or both for commencing and stopping the release of medication or drugs if inner ring 104, capturing ring 106, or both are also embedded with a drug delivery system. RFID tags embedded in inner ring 104, capturing ring 106 or both could further be used to communicate with a drug delivery activation system (not shown), whereby after deploying bloodless circumcision device 100 (FIG. 1) on a user, the RFID tags are activated. The RFID tags then send a signal to the drug delivery activation system to initiate the diffusion of pain medications or anti-inflammatory compounds in inner ring 104, capturing ring 106 or both. The drug delivery activation system may execute a procedure of RFID tag recognition before initiating the diffusion of medications or compounds. In general, RFID tags and barcodes can be read by a scanner and information, such as the device's identification number, the manufacturer as well as the expiry date, can be sent from the scanner (using known technologies such as Bluetooth, Wi-Fi or via a cable) to a local computer, or uploaded directly to a location on the Internet, where software can be used to track inventory, process management or both. Such information could enable strict monitoring in compliance in the use of bloodless circumcision device 100 (FIG. 1), reduce the possibility of reuse of bloodless circumcision device 100, thereby increasing the safety level in use of the device on a large scale, and also reduce the likelihood of using unsafe devices, such as counterfeit bloodless circumcision devices.

The various steps of usage of the bloodless circumcision device of FIG. 1 shown in FIGS. 2A-2E can be performed by substantially any individual on himself or on another individual after a short training session. The short training session may include training on how to properly prepare the penis for circumcision (e.g., washing and cleaning), how to choose the correct size of bloodless circumcision device 100 (FIG. 1) for a given penis size (also described below in FIG. 20), as well as how to properly use and place bloodless circumcision device 100 on a penis. As described, bloodless circumcision device 100 (FIG. 1) does not require a sterile environment (such as an operating room), anesthesia or sterile surgical instruments. In this regard, personnel having undergone the short training session can use bloodless circumcision device 100 to perform circumcisions quickly and efficiently on substantially large amounts of males in any location providing a generally clean environment. The bloodless circumcision device of the disclosed technique is thus cost efficient as compared to the cost of alternative methods for circumcision such as the cost of a mini-surgery. The bloodless circumcision device of the disclosed technique is also simple and scalable as compared to the complexity of alternative methods for circumcision such as a mini-surgery. The bloodless circumcision device of the disclosed technique is also suitable for mass circumcision campaigns due to its safety, scalability and simplicity of use.

As mentioned in the background section, roughly two thirds of those infected with HIV in the world live in Sub-Saharan Africa. Application of the disclosed technique to circumcise males living in Sub-Saharan Africa may potentially reduce the spread of HIV in that continent. Various societies, villages and groups in Sub-Saharan Africa may have cultural, religious or traditional associations with specific colors. In addition in such societies, villages and groups, specific colors may have specific or particular cultural, religious or traditional significance. According to the disclosed technique, bloodless circumcision device 100 is fabricated in a color that takes into account cultural, religious or traditional significance, associations or both when blood circumcision device 100 is to be used in a society, village or group which attributes such significance or associations to specific colors.

It is noted that bloodless circumcision device 100, when being used on infants, can be packaged with other devices and products relevant to infants, such as an umbilical cord clamp, infant diapers, an infant pacifier, alcoholic swabs and the like. Such a package can be marketed as a friendly and convenient pack for parents. In addition, bloodless circumcision device 100 can also be packaged with other accessories and devices used in the context of its deployment, for example rubber gloves and a disinfectant solution. Furthermore, bloodless circumcision device 100 may be packaged with medication, an anesthetic cream, such as EMLA, or both, which can be spread in or around circumferential groove 108. The medication or anesthetic cream may be packaged in a sealed contained which is either manually breakable, controlled by an RFID (i.e., the seal is opened from a signal sent or receive by an RFID embedded in bloodless circumcision device 100) or both. Bloodless circumcision device 100 may also be packaged with a grip or handle to allow for easy removal of foreskin 122 after a few days, once foreskin 122 has become necrotic and the skin tissue in foreskin 122 has died.

Reference is now made to FIG. 3, which is a schematic illustration of another bloodless circumcision device, for accommodating a plurality of penis sizes, generally referenced 150, constructed and operative in accordance with a further embodiment of the disclosed technique. Bloodless circumcision device 150 represents a bloodless circumcision device similar to bloodless circumcision device 100 (FIG. 1). Whereas bloodless circumcision device 100 can be used for a single specified penis size, bloodless circumcision device 150 can be used for a plurality of penis sizes. Bloodless circumcision device 150 includes an introducer 152, a set of inner rings 154 and a set of capturing rings 155. Set of inner rings 154 includes a first size inner ring 160A, a second size inner ring 160B and a third size inner ring 160C. It is noted that the inner diameter of each inner ring in set of inner rings 154 is substantially slightly larger than the diameter of the penis size for which it is to be used for, leaving space for penis erections while bloodless circumcision device 150 is on the penis without applying pressure to the penis itself. Each inner ring in set of inner rings 154 includes a respective circumferential groove on its outer side. First size inner ring 160A includes a circumferential groove 158A, second size inner ring 160B includes a circumferential groove 158B and third size inner ring 160C includes a circumferential groove 158C. Set of capturing rings 155 includes a first size capturing ring 156A, a second size capturing ring 156B and a third size capturing ring 156C. The diameter of a respective capturing ring is such that it fits substantially tightly into a respective circumferential groove of a respective inner ring. First size capturing ring 156A fits substantially tightly into circumferential groove 158A, second size capturing ring 156B fits substantially tightly into circumferential groove 158B and third size capturing ring 156C fits substantially tightly into circumferential groove 158C. It is obvious to the worker skilled in the art that additional inner rings and respective capturing rings of various sizes can be included in bloodless circumcision device 150. Introducer 152 and each inner ring in set of inner rings 154 are typically constructed of a rigid material such as plastic, whereas each capturing ring in set of capturing rings 155 may be constructed of an elastic material such as rubber.

Introducer 152 is an elongated hollow cylinder, suited to receive a penis. The diameter of introducer 152 is substantially similar to the diameter of the largest inner ring in set of inner rings 154, in this case, first size inner ring 160A. As such, introducer 152 can be used to receive different penis sizes. Each inner ring in set of inner rings 154 is a hollow cylinder, having a shorter length than that of introducer 152. In one embodiment of the disclosed technique, some of the inner rings in set of inner rings 154 may have an inner diameter (not shown) greater than the outer diameter of introducer 152, such that a particular inner ring may be fitted over introducer 152. For example, first size inner ring 160A has an inner diameter greater than the outer diameter of introducer 152. Some of the inner rings in set of inner rings 154 may have an outer diameter (not shown) smaller than the inner diameter (not shown) of introducer 152, such that a particular inner ring must be fitted over a penis before introducer 152 is placed over the penis. For example, third size inner ring 160C must be fitted over the penis before introducer 152 is placed over the penis. Bloodless circumcision device 150 is used as described above in FIGS. 2A-2E except that it can accommodate a plurality of penis sizes using a single introducer.

Reference is now made to FIG. 4, which is a schematic illustration of a further bloodless circumcision device, for accommodating a plurality of penis sizes, generally referenced 200, constructed and operative in accordance with another embodiment of the disclosed technique. Bloodless circumcision device 200 represents a bloodless circumcision device substantially similar in design and use to bloodless circumcision device 150 (FIG. 3) and includes an introducer 202, a set of inner rings 204, a set of capturing rings 206 and a deployment ring 216. Set of inner rings 204 includes a first size inner ring 210A, a second size inner ring 210B and a third size inner ring 210C. It is noted that the inner diameter of each inner ring in set of inner rings 204 is substantially slightly larger than the diameter of the penis size for which it is to be used for, leaving space for penis erections while bloodless circumcision device 200 is on the penis without applying pressure to the penis itself. Each inner ring in set of inner rings 204 includes a respective circumferential groove on its outer side as well as a respective selector tab also on its outer side. Introducer 202 may also include a selector tab on its outer side (not shown). First size inner ring 210A includes a circumferential groove 208A and a selector tab 214A, second size inner ring 210B includes a circumferential groove 208B and a selector tab 214B and third size inner ring 210C includes a circumferential groove 208C and a selector tab 214C. Set of capturing rings 206 includes a first size capturing ring 212A, a second size capturing ring 212B and a third size capturing ring 212C. The diameter of a respective capturing ring is such that it fits substantially tightly into a respective circumferential groove of a respective inner ring. First size capturing ring 212A fits substantially tightly into circumferential groove 208A, second size capturing ring 212B fits substantially tightly into circumferential groove 208B and third size capturing ring 212C fits substantially tightly into circumferential groove 208C. Deployment ring 216 includes an inner ring 218 and an outer ring 220. Introducer 202, each inner ring in set of inner rings 204 and deployment ring 216 are typically constructed of a rigid material such as plastic, whereas each capturing ring in set of capturing rings 206 may be constructed of an elastic material such as rubber. Deployment ring 216 can be constructed from the same materials that inner ring 104 (FIG. 1) is constructed from, such as biodegradable materials. Deployment ring 216 can also be referred to as a deployment element and can be embodied having various shapes configured to place a given capturing ring on a given inner ring. It is obvious to the worker skilled in the art that additional inner rings and respective capturing rings of various sizes can be included in bloodless circumcision device 200.

Introducer 202 and set of inner rings 204 can be manufactured as a single element. It is noted that in one embodiment of the disclosed technique, the section where introducer 202 couples with first size inner ring 210A, the section where first size inner ring 210A couples with second size inner ring 210B and the section where second size inner ring 210B couples with third size inner ring 210C can be made of a thinner amount of material than the other sections of introducer 202 and set of inner rings 204 to ease their respective detachment from one another. In such an embodiment, selector tabs 214A-214C may not be required and set of inner rings 204 can be fabricated without selector tabs 214A-214C (not shown). In another embodiment, set of rings 204 are manufactured as a single element and introducer 202 is manufactured as a single separate element. Introducer 202 is an elongated hollow cylinder, suited to receive a penis. The diameter of introducer 202 is substantially similar to the diameter of the largest inner ring in set of inner rings 204, in this case, first size inner ring 210A. As such, introducer 202 can be used to receive different penis sizes. Each inner ring in set of inner rings 204 is a hollow cylinder, having a shorter length than that of introducer 202. In using bloodless circumcision device 200, the appropriate sized inner ring in set of inner rings 204 is selected. Using the respective selector tab, the appropriate inner ring is detached. If the smallest size inner ring was not selected then the other sized inner rings which are not needed can also be detached using their respective selector tabs. Alternatively, inner rings having a size smaller than the appropriately sized inner ring to be used are first detached using the respective selector tab of the largest sized inner ring which is smaller than the appropriately sized inner ring to be used. Inner rings having a size larger than the appropriately sized inner ring to be used can be left attached to introducer 202 while introducer 202 is used to place the appropriately sized inner ring on the penis. Once the appropriately sized inner ring is placed on the penis, the other larger sized inner rings as well as introducer 202 can be broken off using a respective selector tab on the larger sized inner rings. Each inner ring in set of inner rings 204, as well as introducer 202, may be coupled together by a tamper proof seal such that each inner ring, as well as introducer 202, can be detached easily without affecting the functionality of another inner ring or of introducer 202. By manufacturing bloodless circumcision device 200 such that at least set of inner rings 204 are a single element, bloodless circumcision device 200 is substantially a one-size-fits-all device. In this respect, clinics or other locations set up to offer circumcision services to uncircumcised males using the device of the disclosed technique do not need to maintain multiple sizes of the device at a given clinic.

Deployment ring 216 is be used to easily place a given capturing ring in set of capturing rings 206 onto a respective one of set of inner rings 204. A detailed embodiment of deployment ring 216 is shown below in FIGS. 18A-18D. Deployment ring 216 is a substantially a hollow tube, having a shorter length than each one of set of inner rings 204. Inner ring 218 and outer ring 220 are substantially a single element made from a single piece of material. The inner diameters of outer ring 220 and inner ring 218 are substantially the same, whereas the outer diameter of outer ring 220 is slightly larger than the outer diameter of inner ring 218. Deployment ring 216 can be used to place a given capturing ring onto a given inner ring by first placing the given capturing ring around inner ring 218. Inner ring 218 is substantially large enough that each one of set of capturing rings 206 can be placed around inner ring 218, wherein smaller capturing rings may need to be stretched in order to be placed around inner ring 218. Once a given capturing ring has been placed on inner ring 218, deployment ring 216 is placed over the shaft of a penis. As described above in FIGS. 2A-2E, a given inner ring and introducer are then applied to the penis. The given capturing ring is then removed from inner ring 218 and placed around the given inner ring, in the circumferential groove of that inner ring. Deployment ring 216 may be removed from the shaft of the penis immediately after one of the capturing rings is placed in the circumferential groove on an inner ring if deployment ring 216 has a diameter larger than the diameter of the inner ring placed around the glans of the penis (not shown). If deployment ring 216 has a diameter equal to or smaller than the diameter of the inner ring placed around the glans of the penis, then deployment ring 216 either remains on the shaft of the penis until bloodless circumcision device 200 is removed a few days later, or it is removed from the shaft of the penis after placement of the capturing ring by being cut off or broken off. Deployment ring 216 may include a tab (not shown) or a perforated section (not shown) for easily breaking it off to facilitate its removal from the shaft of the penis. Deployment ring 216 can substantially reduce the likelihood that a capturing ring will get tangled in the pubic hairs of an individual while the capturing ring is placed on the shaft of the penis and then on a given inner ring. It is noted that deployment ring 216 can be shaped as any kind of convex polygon, such as a rectangle, square, pentagon or other convex polygonal shapes. In such an embodiment, the diameter of an inscribed circle in the convex polygon must be at least equal to the diameter of the shaft of the penis (not shown). Bloodless circumcision device 200 is used as described above in FIGS. 2A-2E except that it can accommodate a plurality of penis sizes using a single introducer.

Figure 5:
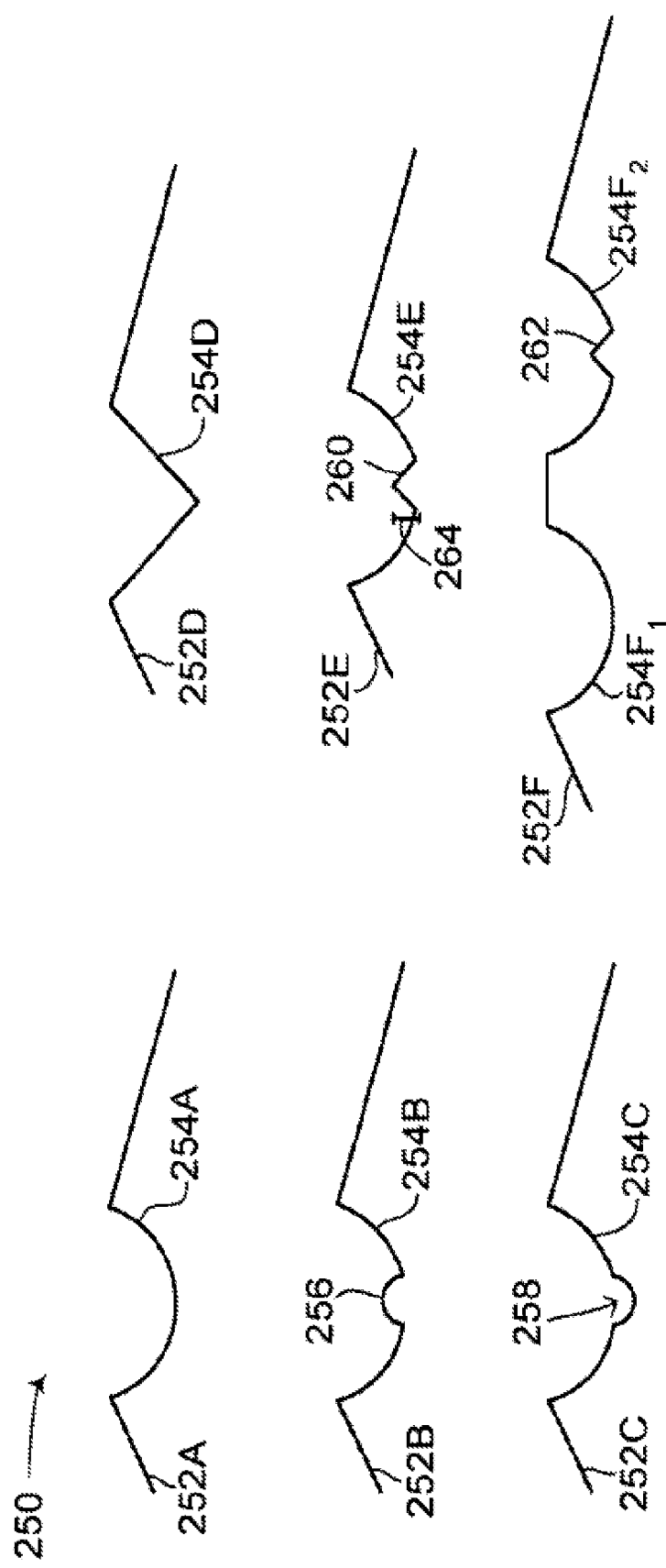
FIG. 5 is a schematic illustration showing different types of circumferential grooves, constructed and operative in accordance with a further embodiment of the disclosed technique.

Reference is now made to FIG. 5, which is a schematic illustration showing different types of circumferential grooves, generally referenced 250, constructed and operative in accordance with a further embodiment of the disclosed technique. In FIG. 5, cross sectional views of six inner rings are shown, each inner ring having a different type of circumferential groove shape. A first inner ring 252A includes a circumferential groove 254A. First inner ring 252A and circumferential groove 254A are substantially similar to inner ring 104 (FIG. 1) and circumferential groove 108 (FIG. 1). Circumferential groove 254A is a standard groove having a semi-circular or 'U' shape. A second inner ring 252B includes a circumferential groove 254B. Circumferential groove 254B includes a circumferential embossed section 256, which can be referred to as a ridge section. When a capturing ring (not shown) is placed in circumferential groove 254B, the capturing ring exerts a compression force on a foreskin (not shown) placed over second inner ring 252B on either side of circumferential embossed section 256. Circumferential groove 254B may expedite the circumcision process by applying a compression force to the foreskin at two separate locations. In addition, if the foreskin to be circumcised is irregular in its radial thickness, the application of a compression force at two separate locations increases the probability that the compression force will be exerted on areas of the foreskin having a smaller thickness. A third inner ring 252C includes a circumferential groove 254C. Circumferential groove 254C includes an inner groove 258. When a capturing ring (not shown) is placed in circumferential groove 254C, if the foreskin to be circumcised is irregular in its radial thickness or substantially thick, then inner groove 258 can accommodate any excess foreskin (i.e., thick foreskin), such that a more uniform compression force is exerted circumferentially on the foreskin. A fourth inner ring 252D includes a circumferential groove 254D. Circumferential groove 254D is a groove having a ridge-like shape, an edge-like shape or a 'V' shape.

A fifth inner ring 252E includes a circumferential groove 254E. Circumferential groove 254E includes a sharp ridge section 260, which can be referred to as a sharp edge section. The height of sharp ridge section 260, as indicated by a line 264, may be for example between 0.05 to 1.5 millimeters. When a capturing ring (not shown) is placed in circumferential groove 254E, the capturing ring exerts an increased compression force on a foreskin (not shown) placed over fifth inner ring 252E, specifically on sharp ridge section 260. The increased compression force on the foreskin as well as the shape of sharp ridge section 260 may cause the foreskin to detach from the penis (not shown) quicker, once the foreskin becomes necrotic, than in the embodiments shown in first to fourth inner rings 252A-252D, as sharp ridge section 260 gradually cuts through the necrotic foreskin.

A sixth inner ring 252F includes at least two circumferential grooves, a first circumferential groove $254F_1$ and a second circumferential groove $254F_2$. Additional circumferential grooves (not shown) may be included in sixth inner ring 252F, the number of circumferential grooves being a matter of design choice. First circumferential groove $254F_1$ may be referred to as a proximal circumferential groove, as it is located closer to the shaft of the penis (not shown) than second circumferential groove 254F$_2$. Second circumferential groove 254F$_2$ may be referred to as a distal circumferential groove, as it is located farther from the shaft of the penis than first circumferential groove 254F$_1$. In one embodiment, second circumferential groove 254F$_2$ can include a sharp ridge section 262, as in fifth inner ring 252E and first circumferential groove 254F$_1$ can have a standard groove having a semi-circular or 'U' shape as in first inner ring 252A. In such an embodiment, two capturing rings are used to exert pressure on the foreskin (not shown), a first capturing ring (not shown) over first circumferential groove 254F$_1$ and a second capturing ring (not shown) over second circumferential groove 254F$_2$. The second capturing ring will exert a higher pressure on the foreskin than the first capturing ring, resulting in necrosis of the foreskin at sharp ridge section 262. Due to the shape of sharp ridge section 262, the necrotic foreskin may detach early as sharp ridge section 262 gradually cuts through the necrotic foreskin. The first capturing ring may exert less pressure on the foreskin, not causing necrosis to the foreskin and not cutting through the foreskin. The first capturing ring may be used to hold the foreskin in place against sixth inner ring 252F after the necrotic foreskin has been detached at second circumferential groove 254F$_2$ until the circumcision area (not show) of the penis (not show) fully heals. In another embodiment, the capturing ring placed in second circumferential groove 254F$_2$ may be significantly tighter than the capturing ring placed in first circumferential groove 254F$_1$, thereby resulting in a similar scenario as described above. In a further embodiment, any one of circumferential grooves 254A-254E may be used in either one of the circumferential grooves of sixth inner ring 252F.

In addition, as mentioned above, an inner ring and a capturing ring of the disclosed technique may be covered, dipped in, coated or embedded with an ointment, cream, ingredient or medication for expediting the process of necrosis, preventing bacterial growth, reducing pain and inflammation or for healing the skin tissue at the location where the foreskin falls off or is removed. Inner groove 258 may be filled with or injected with any such ointment in liquid or gel form such that the ointment is in contact with the skin tissue of the foreskin when the bloodless circumcision device (not shown) of the disclosed technique is applied to a penis. It is noted that any of the inner rings of the disclosed technique, such as inner rings 104 (FIG. 1), 160A-160C (FIG. 3) and 210A-210C (FIG. 4) can be manufactured to have any of the circumferential grooves shown in FIG. 5. In addition, other circumferential groove configurations, such as combinations of the circumferential grooves shown in FIG. 5, are possible and are a matter of design choice.

Reference is now made to FIG. 6, which is a schematic illustration showing different types of capturing rings, generally referenced 280, constructed and operative in accordance with another embodiment of the disclosed technique. A capturing ring 282 is shown in a perspective view in FIG. 6. A capturing ring 284 shows an orthogonal view of capturing ring 282. Capturing rings 282 and 284 are substantially the same as capturing rings 106, 156A-156C and 212A-212C and represent a single capturing ring of a given axial thickness, shown by an arrow 290A. A group of capturing rings 286 is shown in a perspective view in FIG. 6. A group of capturing rings 288 shows an orthogonal view of group of capturing rings 286. Each capturing ring in group of capturing rings 286 is substantially similar. When each capturing ring in group of capturing rings 288 is placed on top of each other, as shown in FIG. 6, the combined axial thickness of group of capturing rings 288, shown by an arrow 290B, is substantially similar to the axial thickness of capturing ring 284. As an example, group of capturing rings 286 includes five capturing rings, which when combined together substantially have the same thickness, size and diameter as capturing ring 282. According to another embodiment of the disclosed technique, a given size capturing ring may be manufactured as a plurality of smaller thickness capturing rings, for example as two rings, three rings, four rings, five rings, and so on, so that the combined thickness of the plurality of smaller thickness capturing rings matches the thickness of the given size capturing ring. Manufacturing a given size capturing ring as a plurality of smaller thickness capturing rings reduces concerns and issues in manufacturing defects, since if a single capturing ring in a group of capturing rings is defective, such as one of the capturing rings in group of capturing rings 286, the other capturing rings in the group of capturing rings can still be used. If a given capturing ring, such as capturing ring 282, is defective, then the capturing ring may not be used. In addition, by reducing the thickness of a capturing ring, capturing rings may be more easily positioned on the foreskin and an inner ring, since smaller thicknesses make capturing rings, which are made of a stretchable material, easier to stretch. Also, a plurality of capturing rings enables the amount of pressure applied to the foreskin to be controlled, as an increase in the number of capturing rings placed around the foreskin and an inner ring will increase the pressure exerted on the foreskin. It is noted that the capturing rings of the disclosed technique can be manufactured according to any of the types of capturing rings shown in FIG. 6 and described herein.

Figure 7E:
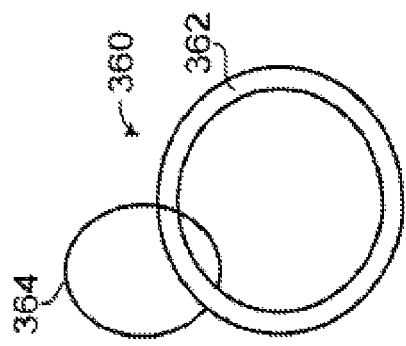

Reference is now made to FIGS. 7A-7H, which are schematic illustrations showing different shapes of capturing rings, constructed and operative in accordance with a further embodiment of the disclosed technique. FIG. 7A shows a capturing ring shape, generally referenced 300, and includes a side orthogonal view 302 of capturing ring 300 and a top orthogonal view 304 of capturing ring 300. In this embodiment, capturing ring 300 is shaped as a spring in its axial direction, including at least one coil. As shown in side orthogonal view 302, capturing ring 300 includes three coils. As shown in top orthogonal view 304, capturing ring 300 can be stretched radially in the directions of arrows 306, thereby increasing its diameter in order to place capturing ring 300 in the circumferential groove (not shown) of an inner ring (not shown). Once placed on an inner ring over the foreskin (not shown) of an individual, due to the spring shape of capturing ring 300, once the force in the direction of arrows 306 is released capturing ring 300 returns to its original diameter, exerting a uniform radial force on the foreskin in the direction of the inner ring. FIG. 7B shows another capturing ring shape, generally referenced 310, shown in a cross sectional view. The cross sectional shape of capturing ring 310 is substantially a gear 312, having a plurality of outer teeth 314 and inner teeth 316. Between the plurality of teeth (both inner and outer) is a plurality of spaces 318. When capturing ring 310 is placed over the foreskin (not shown) of an individual, inner teeth 316 and plurality of spaces 318 between inner teeth 316 exert an inward radial compression force on the foreskin. Due to the gear shape of capturing ring 310, capturing ring 310 can accommodate foreskin having an irregular thickness circumferentially, since inner teeth 316 will exert a greater force on the foreskin than plurality of spaces 318. Outer teeth 314 are optional and may be manufactured as part of capturing ring 310 to simplify the manufacturing process of capturing ring 310. It is noted that capturing ring 310 may be designed to have other cross sectional shapes, such as a triangular cross sectional shape, a star cross sectional shape and the like. Other cross sectional shapes are possible as is obvious to one skilled in the art.

FIG. 7C shows a further capturing ring shape, generally referenced 320, shown in a top orthogonal view. Capturing ring 320 includes a first section 322 and a second section 324. First section 322 and second section 324 are separate elements and can be detached from one another. Second section 324 includes a set of arms 325. First section 322 includes a set of arm receivers (not shown), for receiving set of arms 325 as well as an opening 326. First section 322 is stretched open and placed around a foreskin (not shown) and an inner ring (not shown). Second section 324 is then stretched open and placed around first section 322 such that set of arms 325 enter the set of arm receivers on first section 322, thereby rigidly coupling first section 322 with second section 324. It is obvious to one skilled in the art that other coupling mechanisms could be used to couple first section 322 with second section 324. FIG. 7D shows another capturing ring shape, generally referenced 330, and includes a cross sectional view 332 of capturing ring 330 and a top orthogonal view 334 of capturing ring 330. Capturing ring 330 is substantially shaped as a spring in its circumferential direction, having a diameter shown by an arrow 335. The diameter of the spring may be, for example, 1 to 3 millimeters. The spring of capturing ring 330 is closed into a loop, giving capturing ring 330 a toroidal shape, as shown in top orthogonal view 334. Also, as shown in top orthogonal view 334, capturing ring 330 can be stretched radially in the directions of arrows 336, thereby increasing its diameter in order to place capturing ring 330 in the circumferential groove (not shown) of an inner ring (not shown). Once placed on an inner ring over the foreskin (not shown) of an individual, due to the spring shape of capturing ring 330, once the force in the direction of arrows 336 is released capturing ring 330 returns to its original diameter, exerting a uniform radial force on the foreskin in the direction of the inner ring.

Figure 7G:
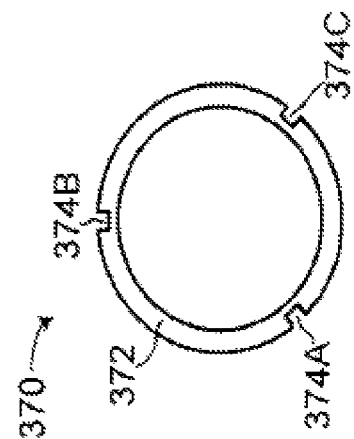
Figure 7F:
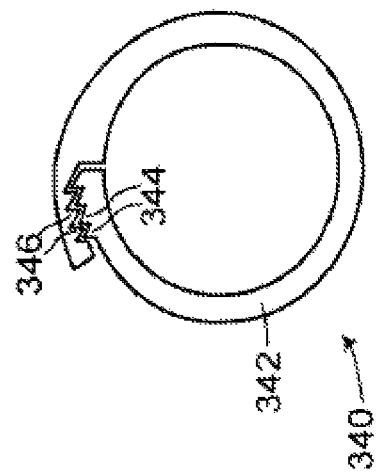
Figure 7H:
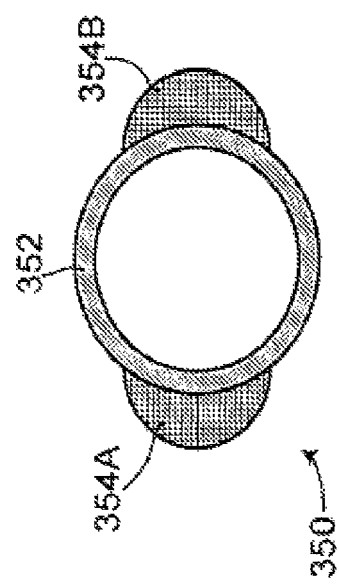

FIG. 7E shows a further capturing ring shape, generally referenced 340, shown in a top orthogonal view. Capturing ring 340 is made from a single piece of material 342 and includes a set of inner teeth 344 and a set of outer teeth 346. Capturing ring 340 can be opened up and placed around a foreskin (not shown) and an inner ring (not shown). Once placed around the foreskin, capturing ring 340 can be placed into a closed position (as shown in FIG. 7E) by interlocking set of inner teeth 344 into set of outer teeth 346. As shown, capturing ring 340 can be ratcheted by interlocking fewer or more of set of inner teeth 344 into set of outer teeth 346. It is obvious to one skilled in the art that other mechanisms, for example a mechanism using snaps, can be used to place and hold capturing ring 340 in a closed position. In addition, capturing ring 340 enables the compression pressure it exerts on a foreskin (not shown) and an inner ring (not shown) to be selected. For example, capturing ring 340 may be embodied having a plurality of teeth such that a plurality of compression pressures can be selected. In such an embodiment, a pressure meter may be optionally included with the disclosed technique which can be coupled with capturing ring 340 to measure the compression pressure of capturing ring 340 while it is placed around the foreskin and the inner ring. FIG. 7F shows another capturing ring shape, generally referenced 350, shown in a top orthogonal view. Capturing ring 350 includes a capturing ring 352 and leaflets 354A and 354B. Capturing ring 352 is substantially similar to capturing ring 106 (FIG. 1). Leaflets 354A and 354B can be constructed in a plurality of other shapes, such as half rings (not shown) or lines (now shown). Leaflets 354A and 354B simplify grasping capturing ring 352. Leaflets 354A and 354B are provided to facilitate the handling and placing of capturing ring 352 on an inner ring (not shown). FIG. 7G shows a further capturing ring shape, generally referenced 360, shown in a top orthogonal view, mentioned above in the description of FIGS. 2A-2E. Capturing ring 360 includes a capturing ring 362 and a suture string 364. Capturing ring 362 is substantially similar to capturing ring 106 (FIG. 1). Suture string 364 forms a closed loop around capturing ring 362 and can be used to remove capturing ring 362 once capturing ring 362 has been placed around a penis (not shown) before the foreskin of the penis falls off or before it is removed. FIG. 7H shows another capturing ring shape, generally referenced 370, shown in a top orthogonal view, mentioned above in the description of FIGS. 2A-2E. Capturing ring 370 includes a capturing ring 372 and a plurality of holes 374A, 374B and 374C. Capturing ring 372 is substantially similar to capturing ring 106 (FIG. 1). A removal device can be coupled with plurality of holes 374A, 374B and 374C for removing capturing ring 372 once capturing ring 372 has been placed around a penis (not shown) before the foreskin of the penis falls off or is removed. It is noted that other arrangements of plurality of holes 374A, 374B and 374C are possible and that the three holes shown in capturing ring 372 are brought merely as an example. According to the disclosed technique, the embodiment of capturing ring 372 should have at least one hole (not shown) to which a removal device can be coupled with for removing capturing ring 372.

Reference is now made to FIGS. 8A-8B, which are schematic illustrations showing different types of introducer shapes, constructed and operative in accordance with another embodiment of the disclosed technique. FIG. 8A shows a first introducer shape, generally referenced 380, shown in a longitudinal cross section view. First introducer 380 includes an introducer 382. Introducer 382 has a circular shape and includes three separate sections, a top section 388, an inner ring receiving section 390 and a tapered section 392. Introducer 382 has an opening 394 at the end of tapered section 392, into which the glans of a penis (not shown) is inserted. Tapered section 392 may be made of an elastic or distensible material to received the glans of a penis as the penis is inserted into introducer 382. As the penis is inserted into introducer 382, tapered section 392 may expand to accommodate the penis. An inner diameter of introducer 382, shown by an arrow 396, is uniform along top section 388 and inner ring receiving section 390. The outer diameter (not shown) of introducer 382 is larger in top section 388 than in inner ring receiving section 390. Inner ring receiving section 390 can receive an inner ring 384 having a circumferential groove 386. FIG. 8B shows a second introducer shape, generally referenced 410, shown in a longitudinal cross section view. Second introducer 410 includes an introducer 412. Introducer 412 has a circular shape and includes three separate sections, a top section 418, an inner ring receiving section 420 and a conical section 422. Introducer 412 has an opening 424 at the end of conical section 422, into which the glans of a penis (not shown) is inserted. Conical section 422 may be made of an elastic or distensible material to received the glans of a penis as the penis is inserted into introducer 412. As the penis is inserted into introducer 412, conical section 422 may expand to accommodate the penis. An inner diameter of introducer 412, shown by an arrow 426, is uniform along top section 418 and inner ring receiving section 420. The outer diameter (not shown) of introducer 412 is larger in top section 418 than in inner ring receiving section 420. Inner ring receiving section 420 can receive an inner ring 414 having a circumferential groove 416.

Using either first introducer 382 or second introducer 412, inner ring 384 or inner ring 414 is placed on its respective introducer in its respective inner ring receiving section. The introducer is then placed over the opening of the foreskin near the glans of a penis. As the introducer is moved down over the penis, the opening of the foreskin (not shown) is dilated and the foreskin is stretched around either tapered section 392 or conical section 422 as the introducer is moved towards the glans of the penis. This is important if the penis on which the bloodless circumcision device of the disclosed technique is to used suffers from phimosis, a medical condition in which the foreskin of the penis is constricted and cannot be drawn back. As the foreskin and its opening are dilated and stretched by either tapered section 392 or conical section 422, inner ring 384 or inner ring 414 is advanced over the glans of the penis and the foreskin is pulled up over a respective inner ring.

Figure 9A:
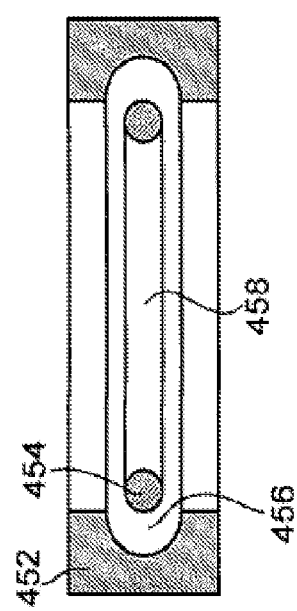
FIGS. 9A-9B are schematic illustrations showing another bloodless circumcision device, constructed and operative in accordance with a further embodiment of the disclosed technique.
Figure 9B:
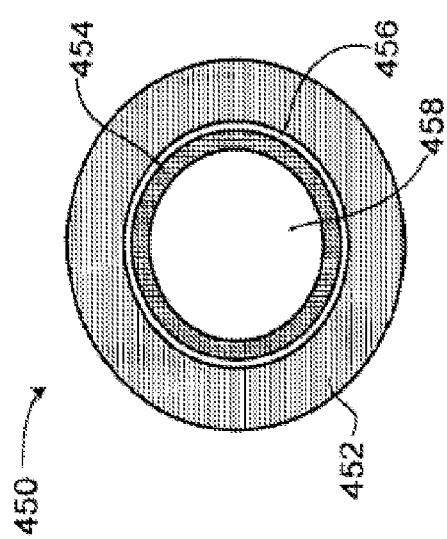

Reference is now made to FIGS. 9A and 9B, which are schematic illustrations showing another bloodless circumcision device, generally referenced 450, constructed and operative in accordance with a further embodiment of the disclosed technique. Bloodless circumcision device 450 includes an outer ring 452 and a capturing ring 454. FIG. 9A shows bloodless circumcision device 450 from an orthogonal top view, whereas FIG. 9B shows bloodless circumcision device 450 in a cross sectional view. Bloodless circumcision device 450 operates in a manner similar to bloodless circumcision device 100 except that the location and placement of the inner ring and the capturing ring are reversed. Capturing ring 454 is substantially similar to capturing ring 106 (FIG. 1) and has a circular cross section. Outer ring 452 operates in a similar yet reversed manner to inner ring 104 (FIG. 1). Outer ring 452 includes an inner circumferential groove 456. Inner circumferential groove 456 may be shaped like any of the circumferential groove shapes shown above in FIG. 5.

In bloodless circumcision device 450, once the foreskin of a penis (not shown) has been pulled down away from the glans of the penis (not shown), capturing ring 454 is placed over the glans of the penis. As shown in FIGS. 9A and 9B, the glans of the penis is placed in the opening 458 of capturing ring 454. The diameter of capturing ring 454 is such that it is slightly larger than the diameter of the penis during an erection. The foreskin is then pulled up over capturing ring 454. Outer ring 452 is then placed over the foreskin such that capturing ring 454 is aligned with inner circumferential groove 456. Capturing ring 454 and inner circumferential groove 456 exert pressure on the foreskin, thereby starting a process of ischemic necrosis of the foreskin, as the outer diameter (not shown) of capturing ring 454 is substantially the same as the inner diameter (not shown) of outer ring 452. It is noted that capturing ring 454 may be made out of a soft, distensible, resilient material and outer ring 452 may be made out of a rigid material. In another embodiment of the disclosed technique, capturing ring 454 may be made out of a rigid material and outer ring 452 may be made out of a soft, distensible, resilient material. In a further embodiment, capturing ring 454 may have a cross section shaped like a triangle, as shown below in FIG. 9D. Other cross section shapes for capturing ring 454 are possible.

Figure 9C:
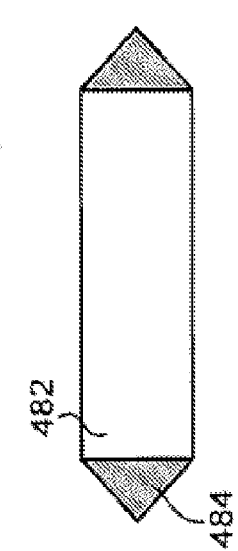
FIGS. 9C-9D are schematic illustrations showing the capturing ring of FIGS. 9A-9B, constructed and operative in accordance with another embodiment of the disclosed technique.
Figure 9D:
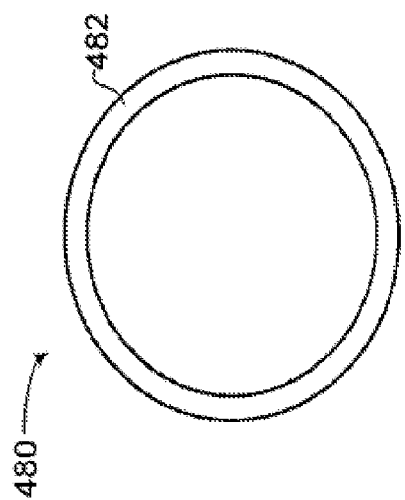

Reference is now made to FIGS. 9C-9D, which are schematic illustrations showing the capturing ring of FIGS. 9A-9B, generally referenced 480, constructed and operative in accordance with another embodiment of the disclosed technique. FIG. 9C shows capturing ring 480 from an orthogonal top view, whereas FIG. 9D shows capturing ring 480 in a cross sectional view. Capturing ring 480 includes a capturing ring 482 and a tapered circumference section 484, which extends around the outer circumference of capturing ring 482. Capturing ring 482 is substantially similar to capturing ring 454 (FIGS. 9A and 9B). Tapered circumference section 484 has a cross section shaped like a triangle, yet other cross sectional shapes of tapered circumference section 484 are possible. When capturing ring 482 is placed over the glans of a penis (not shown) and the foreskin of the penis (not shown) is pulled up over capturing ring 482, tapered circumference section 484 exerts an outward radial pressure on the foreskin. When an outer ring (not shown) is then placed over the foreskin such that capturing ring 482 is aligned with the inner circumferential groove (not shown) of the outer ring, then the outer ring and capturing ring 482 exert an increased pressure on the foreskin, thereby causing ischemic necrosis. Tapered circumference section 484 may increase the pressure exerted on the foreskin, thereby quickening the process of ischemic necrosis of the foreskin.

Reference is now made to FIGS. 10A-10B, which are schematic illustrations showing a capturing ring including a groove on its inner side, generally referenced 500, constructed and operative in accordance with a further embodiment of the disclosed technique. FIG. 10A shows capturing ring 500 in a cross sectional view and FIG. 10B shows capturing ring 500 in a top orthogonal view. Capturing ring 500 includes a capturing ring section 502 and an inner groove 504. Capturing ring 500 can be used in the embodiment of the bloodless circumcision device of the disclosed technique described above in reference to FIGS. 2A-2E, where the capturing ring may be made of a solid and rigid material, having a fixed diameter and the inner ring may be made of an elastic or distensible material. In such an embodiment, once the foreskin (not shown) is placed between an elastic inner ring (not shown) and capturing ring 500, inner groove 504 enables any excess foreskin (i.e., thick foreskin) to be accommodated for, such that a more uniform compression force is exerted circumferentially on the foreskin.

Reference is now made to FIGS. 10C-10D which are schematic illustrations showing another capturing ring including an embossed section on its inner side, generally referenced 520, constructed and operative in accordance with another embodiment of the disclosed technique. FIG. 10C shows capturing ring 520 in a cross sectional view and FIG. 10D shows capturing ring 520 in a top orthogonal view. Capturing ring 520 includes a capturing ring section 522 and an embossed section 524 on the inner side of capturing ring 520. Embossed section 524 can be embodied having other shapes, such as a tapered shape or a pointed shaped. Capturing ring 520 can be used in the embodiment of the bloodless circumcision device of the disclosed technique described above in reference to FIGS. 2A-2E, where the capturing ring may be made of a solid and rigid material, having a fixed diameter and the inner ring may be made of an elastic or distensible material. In such an embodiment, once the foreskin (not shown) is placed between an elastic inner ring (not shown) and capturing ring 520, embossed section 524 exerts an increased pressure on the foreskin thereby expediting the process of ischemic necrosis.

Figure 11:
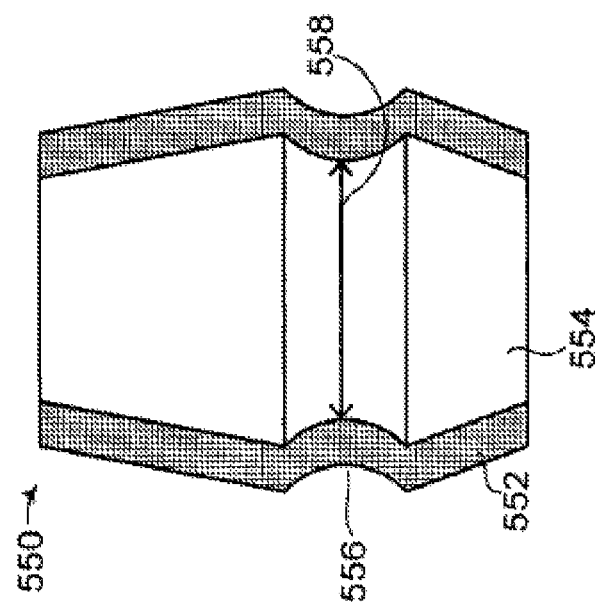
FIG. 11 is a schematic illustration of a cross section of the inner ring of FIG. 1, constructed and operative in accordance with a further embodiment of the disclosed technique.

Reference is now made to FIG. 11, which is a schematic illustration of a cross section of the inner ring of FIG. 1, generally referenced 550, constructed and operative in accordance with a further embodiment of the disclosed technique. Inner ring 550 is substantially similar to inner rings 104 (FIG. 1), 160A-160C (FIG. 3) and 210A-210C (FIG. 4). Inner ring 550 includes a circumferential groove 556 and a hollow 554 where the glans of a penis (not shown) is placed. This thickness of the material from which inner ring 550 is fabricated from is shown in a section 552. An inner diameter 558 of inner ring 550 is shown via a double-headed arrow. Inner diameter 558 represents the smallest diameter from one side of circumferential groove 556 to the other side of circumferential groove 556. In general, according to the disclosed technique, the size of a given capturing ring (not shown) to be used with a given inner ring like inner ring 550, such as in the case where the bloodless circumcision device of the disclosed technique is to be used for multiple penis sizes, is determined based on the size of the inner diameter of the inner ring. In general, the inner ring size is determined based on the diameter of the shaft of the penis on which it will be used. For the bloodless circumcision device of the disclosed technique to be used effectively and safely, the outer diameter of a given capturing ring (not shown) in a relaxed state should not be smaller than the inner diameter of the inner ring to which it will be used with. Otherwise, if the capturing ring slips off the inner ring onto the penis, may exert too great a pressure on the foreskin or the shaft of the penis, thereby causing pain to the individual.

Figure 12:
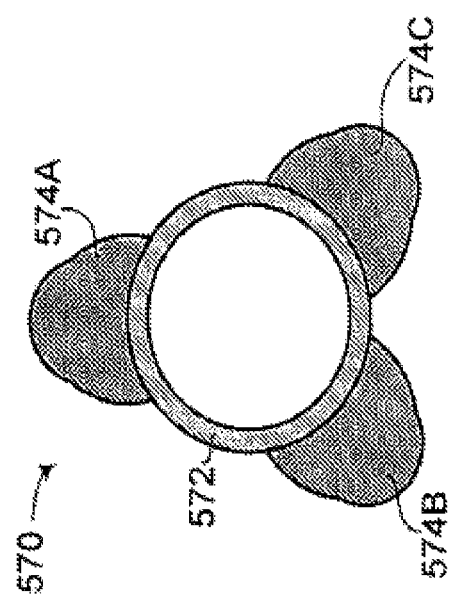
FIG. 12 is a schematic illustration of a further capturing ring for foreskin disposal, constructed and operative in accordance with another embodiment of the disclosed technique.

Reference is now made to FIG. 12, which is a schematic illustration of a further capturing ring for foreskin disposal, generally referenced 570, constructed and operative in accordance with another embodiment of the disclosed technique. Capturing ring 570 includes a capturing ring 572. Capturing ring 572 is substantially similar to capturing rings 106 (FIG. 1), 156A-156C (FIG. 3), 212A-212C (FIG. 4) and 350 (FIG. 7F). Capturing ring 572 includes a plurality of flaps 574A, 574B and 574C. Plurality of flaps 574A-574C are substantially similar to leaflets 354A and 354B (FIG. 7F) of capturing ring 350. Plurality of flaps 574A-574C is substantially fabricated from a soft, distensible, elastic material. Using capturing ring 572, once the foreskin (not shown) has died plurality of flaps 574A-574C can be folded up over the foreskin. By then pulling up on plurality of flaps 574A-574C, capturing ring 572 as well as the foreskin can be removed from the penis (not shown) and disposed of, such as in a waste basket or garbage pail, without the individual having to handle or touch the foreskin which has undergone necrosis. Other shapes, forms and the number of flaps on capturing ring 572 are possible as is obvious to one skilled in the art. Plurality of flaps 574A-574C and capturing ring 572 can be constructed from a single piece of material. In an alternative embodiment, plurality of flaps 574A-574C and capturing ring 572 can each be constructed from a single piece of material. In such an embodiment plurality of flaps 574A-574C may be coupled to one another by an elastic ring (not shown) have dimensions similar to the dimensions of capturing ring 572. In this embodiment, plurality of flaps 574A-574C may be coupled to capturing ring 572 by placing the elastic ring under capturing ring 572 and folding plurality of flaps 574A-574C over capturing ring 572 and the foreskin. Squeezing on plurality of flaps 574A-574C and pulling in an upward motion will remove capturing ring 572 and the foreskin without the individual having to touch or handle the dead necrotic skin of the foreskin.

Figure 13A:
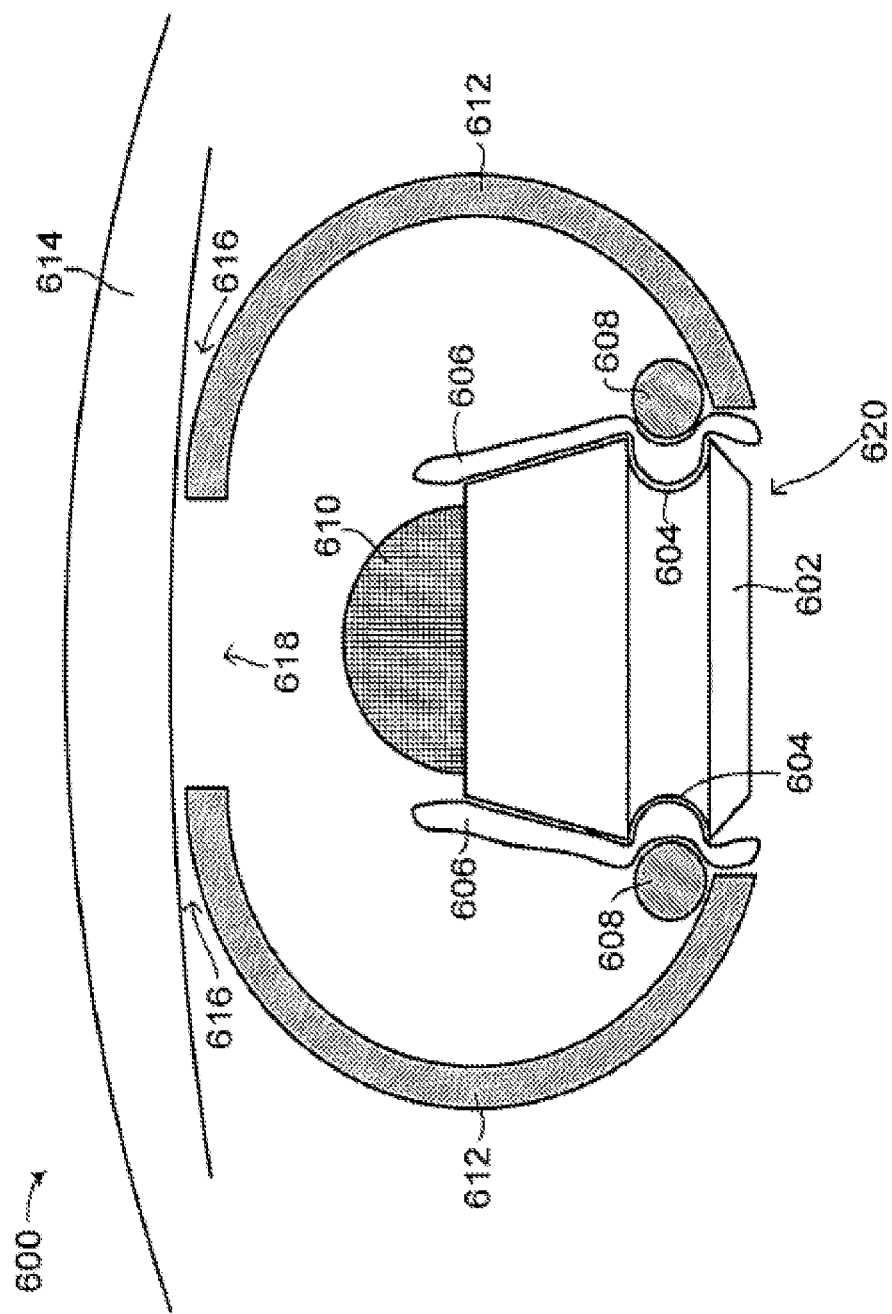
FIGS. 13A-13C are schematic illustrations of another bloodless circumcision device, constructed and operative in accordance with a further embodiment of the disclosed technique.
Figure 13B:
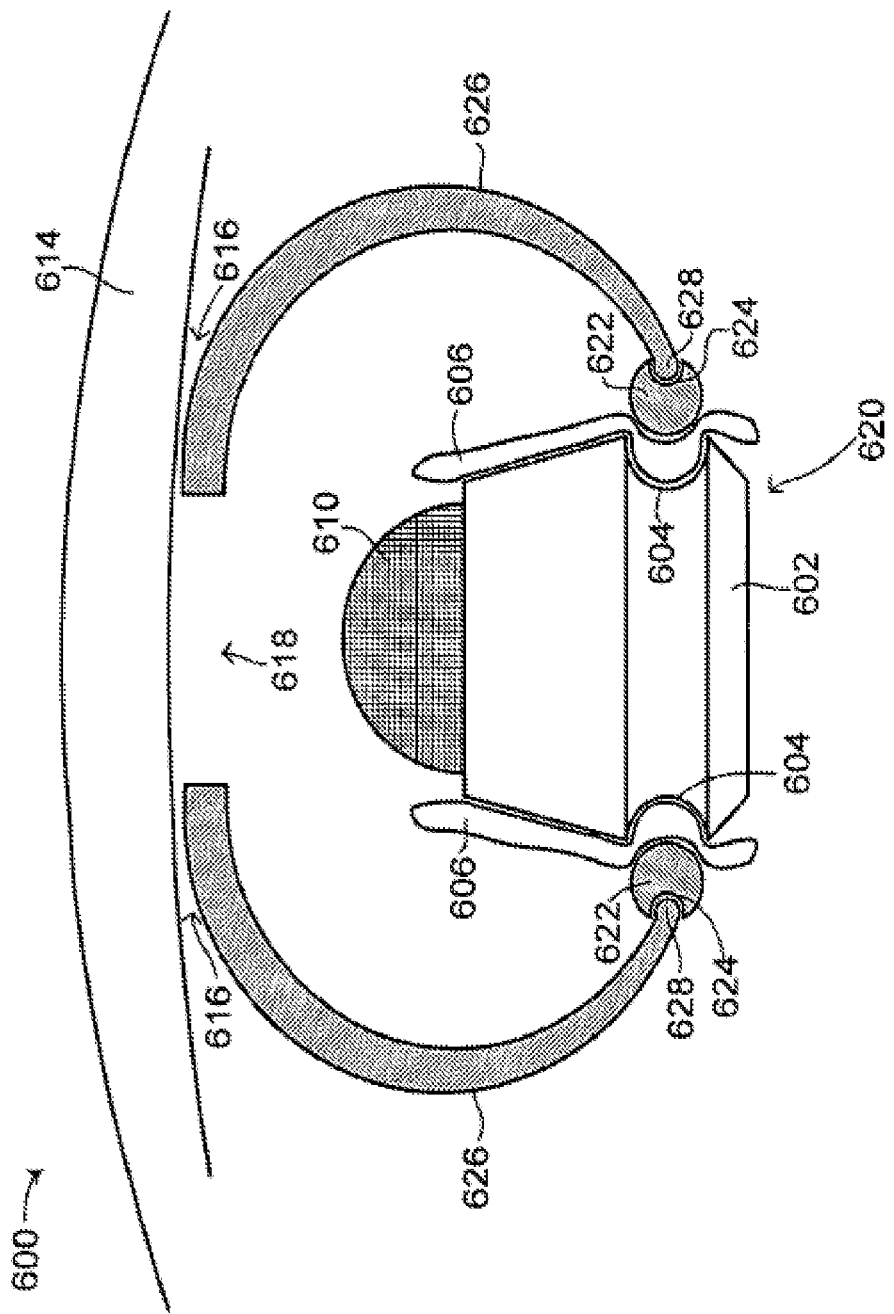
Figure 13C:
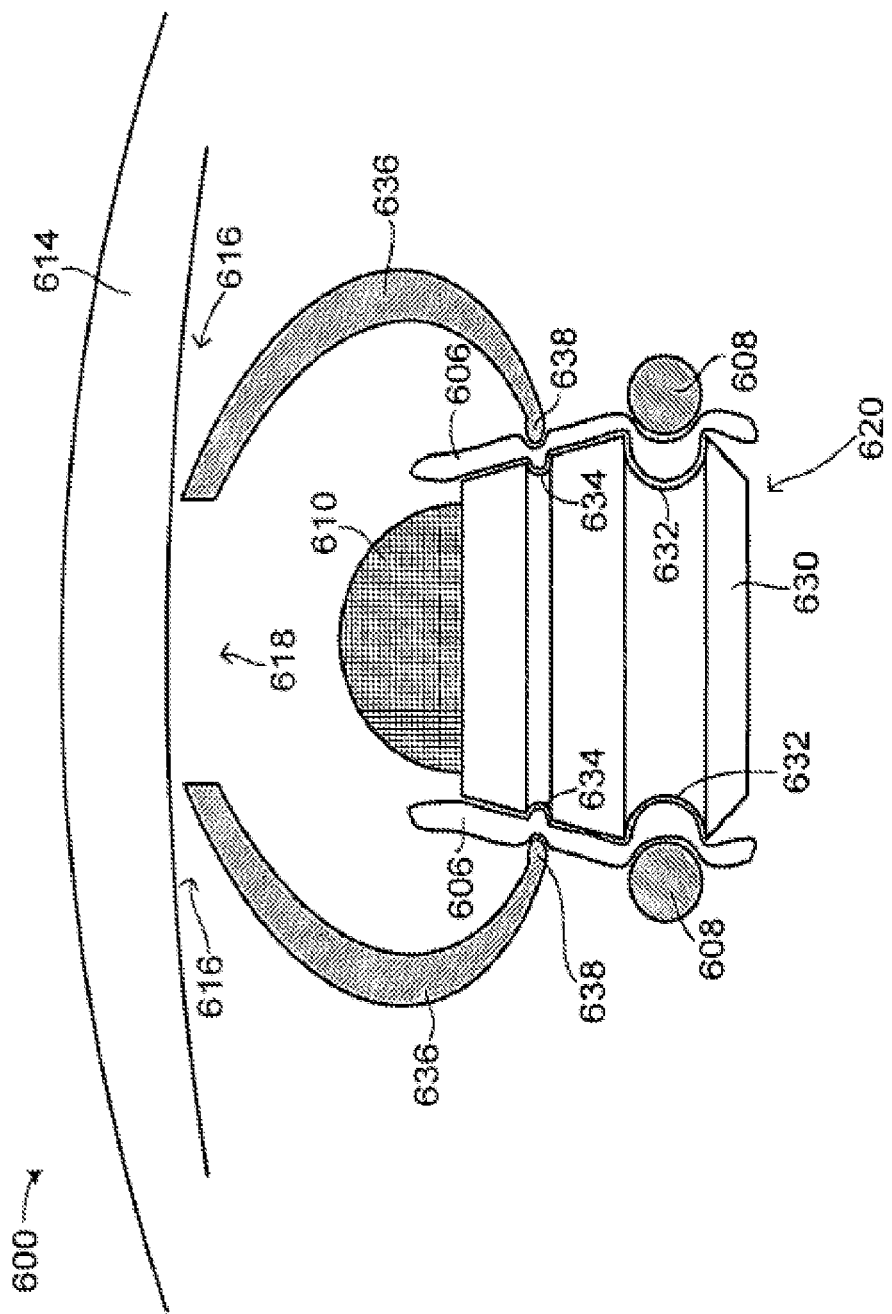

Reference is now made to FIGS. 13A-13C, which are schematic illustrations of another bloodless circumcision device, generally referenced 600, constructed and operative in accordance with a further embodiment of the disclosed technique. FIG. 13A shows a first embodiment of bloodless circumcision device 600 for reducing friction between the glans of the penis and a garment, like an undergarment such as a diaper. Bloodless circumcision device 600 may be used on infants, children or adults for reducing potential friction between the glans of the penis and an undergarment. FIG. 13A shows an inner ring 602 placed on the shaft of a penis (not shown). Inner ring 602 includes a circumferential groove 604. The individual's foreskin 606 (shown cross sectionally) has been pulled up over inner ring 602 and a capturing ring 608 (shown cross sectionally), having a circular cross section, has been placed over foreskin 606. Capturing ring 608 is substantially aligned with circumferential groove 604. As shown, when bloodless circumcision device 600 is used, the glans 610 of the penis may be exposed. Bloodless circumcision device 600 includes a protective element 612 (shown cross sectionally) for distancing glans 610 from an undergarment 614. Undergarment 614 may be underwear, boxer shorts or a diaper. As shown by arrows 616, protective element 612 rubs against undergarment 614 instead of glans 610 rubbing against undergarment 614. Protective element 612 is substantially round having an upper opening 618 and a lower opening 620. Upper opening 618 distances glans 610 from undergarment 614 while enabling glans 610 to remain aerated. When used with infants, aerating glans 610 may expedite the drying up process of glans 610. Lower opening 620 may have a diameter which is slightly smaller than the diameter of capturing ring 608 when capturing ring 608 is placed over foreskin 606 and inner ring 602. As such, when protective element 612 is placed over glans 610 under capturing ring 608, the larger diameter of capturing ring 608 may keep protective element 612 in place.

FIG. 13B shows a second embodiment of bloodless circumcision device 600 for reducing friction between the glans of the penis and an undergarment, such as a diaper. Similar elements to FIG. 13A are numbered using identical numbers in FIG. 13B. In FIG. 13B, capturing ring 608 (FIG. 13A) has been replaced by a capturing ring 622 (shown cross sectionally). Capturing ring 622 has an inner groove 624. In FIG. 13B, protective element 612 (FIG. 13A) has been replaced by a protective element 626 (shown cross sectionally). Protective element 626 has a curved end 628. Curved end 628 is substantially similar in size to inner groove 624. Curved end 628 can be inserted into inner groove 624. Inner groove 624 is used for coupling protective element 626 to capturing ring 622, thereby holding protective element 626 in place.

FIG. 13C shows a third embodiment of bloodless circumcision device 600 for reducing friction between the glans of the penis and an undergarment, such as a diaper. Similar elements to FIG. 13A are numbered using identical numbers in FIG. 13C. In FIG. 13C, inner ring 602 (FIG. 13A) has been replaced by an inner ring 630. Inner ring 630 includes a first circumferential groove 632 and a second circumferential groove 634. Capturing ring 608 is substantially aligned with first circumferential groove 632. In FIG. 13C, protective element 612 (FIG. 13A) has been replaced by a protective element 636 (shown cross sectionally). Protective element 636 has a curved end 638. Curved end 638 is substantially similar in size to second circumferential groove 634. Curved end 638 can be inserted into second circumferential groove 634. Second circumferential groove 634 is used for exerting additional pressure on foreskin 606 and for coupling protective element 636 to inner ring 630, thereby holding protective element 636 in place.

Protective elements 612, 626 and 636 may be made of a rigid material, such as hard plastic, or a soft, distensible and elastic material. In the case that protective elements 612, 626 and 636 are made of a rigid material, each protective element may be made from two identical parts which can be snapped together over bloodless circumcision device 600. In the case that protective elements 612, 626 and 636 are made from a soft elastic material, lower opening 620 of each protective element may be stretched over bloodless circumcision device 600.

It is also noted that besides the embodiments shown in FIGS. 13A, 13B and 13C, a cover may also be provided with the bloodless circumcision device of the disclosed technique for covering the inner ring, such as inner ring 608 (FIGS. 13A and 13C). Such a covering (not shown) can reduce friction between the inner ring and the areas of the body around the penis which may rub against the inner ring during an individual's daily activities while wearing the circumcision device of the disclosed technique.

Reference is now made to FIGS. 14A-14E, which are schematic illustrations of different inner ring shapes and configurations for use with a bloodless circumcision device, generally referenced 650, 660, $670_1$, $670_2$ and 690 respectively, constructed and operative in accordance with another embodiment of the disclosed technique. FIG. 14A shows an inner ring 650. Inner ring 650 is shown in a cross sectional view. Inner ring 650 includes a circumferential groove 652. A capturing ring 654 is placed over a foreskin (not shown) inside circumferential groove 652. As shown in FIG. 14A, circumferential groove 652 is asymmetrical along a vertical axis 656. Due to the asymmetrical shape of circumferential groove 652, capturing ring 654 rests in a section 658 of circumferential groove 652. When inner ring 650 is placed around a penis (not shown) section 658 may be distal or proximal to the corona of the penis (not shown). The asymmetrical shape of circumferential groove 652 may ease the placement of capturing ring 654 on inner ring 650. The asymmetrical shape of circumferential groove 652 may also reduce the likelihood of capturing ring 654 accidentally falling off inner ring 650. In addition, the shape of circumferential groove 652 may enable easier removal of capturing ring 654 as well as any dry, dead foreskin (not shown) while reducing the likelihood of touching any live tissue during such a removal. In addition, if the increased curvature of circumferential groove (i.e., section 658) is positioned towards the distal side of the penis, the removal of capturing ring 654 and inner ring 650 may be easier as the necrotic tissue to be cut can be cut substantially close to capturing ring 654. Cutting the necrotic tissue substantially close to capturing ring 654 substantially reduces the amount of necrotic tissue that needs to pass over inner ring 650 before inner ring 650 is removed. Other asymmetrical shapes for circumferential groove 652 are possible and are a matter of design choice.

FIG. 14B shows an inner ring 660 from a top orthogonal view. Inner ring 660 can be opened and closed using a mating mechanism. Inner ring 660 includes a female connector 662 and a male connector 664. Female connector 662 and male connector 664 have complementary shapes. The shapes of female connector 662 and male connector 664 in inner ring 660 are merely examples. Other shapes for female connector 662 and male connector 664 are possible and are a matter of design. Inner ring 660 is closed by inserting male connector 664 in female connector 662. As FIG. 14B shows a top orthogonal view of inner ring 660, male connector 664 may be inserted into female connector 662 in a direction perpendicular to the plane of FIG. 14B. As inner ring 660 can be opened and closed, inner ring 660 may be more easily inserted into the opening of the foreskin of an individual (not shown) and then subsequently closed around the corona of the glans penis (not shown) of the individual.

FIGS. 14C and 14D show an inner ring in a cross sectional view, generally referenced $670_1$ and in a top orthogonal view, generally referenced $670_2$. Inner rings $670_1$ and $670_2$ include a circumferential groove 672, an inner lip 674, an outer lip 678 and an opening 676. As shown in more detail in FIG. 14E, a penis (not shown) in inserted into opening 676 in the direction of an arrow 675. Unlike other inner rings of the disclosed technique described above, the radial direction of circumferential groove 672, shown as an arrow 677, is parallel to the direction in which the penis is inserted into opening 676 (i.e., the direction of arrow 675). In other inner rings of the disclosed technique, such as inner ring 104 (FIG. 2B), the radial direction of the circumferential groove is perpendicular to the direction in which the penis is inserted into the opening of the inner ring. As shown in FIGS. 14C and 14D, inner lip 674 is slightly larger than outer lip 678. Inner lip 674 includes an overhang 688 over circumferential groove 672. FIG. 14E shows how inner ring $670_1$ (FIG. 14C) is used with the disclosed technique as a bloodless circumcision device, generally referenced 690. FIG. 14E shows a penis (not labeled) including a shaft 680, a glans 682 and a foreskin 684. As shown, foreskin 684 is stretched over inner ring $670_1$ which is inserted over glans 682 through opening 676. Foreskin 684 is pulled over outer lip 678, inserted into circumferential groove 672 and then pulled over inner lip 674. A capturing ring 686 is then inserted into circumferential groove 672, thereby compressing foreskin 684 between capturing ring 686 and inner lip 674, causing ischemic necrosis to foreskin 684. An overhang 688 of inner lip 674 substantially prevents capturing ring 686 from unintentionally slipping out of circumferential groove 672.

According to the disclosed technique, a bloodless circumcision device is applied to the foreskin (not show) of a penis (not shown), causing the foreskin to undergo ischemic necrosis, resulting in tissue death of the foreskin tissue. In certain cases, after a few days, the necrotic foreskin may fall off naturally. In other cases, it may take between a week to two weeks for the necrotic foreskin to fall off naturally. In either case, since the tissue in the foreskin is substantially dead after a few days, according to the disclosed technique, the dead foreskin may be removed using a foreskin cutter without having to wait until the dead foreskin falls off naturally. In general, necrosis of the foreskin according to the disclosed technique leads to dry gangrene (i.e., tissue death without subsequent bacterial decomposition). The necrotic foreskin becomes substantially dry, and in many cases the necrotic foreskin also hardens. Regular or tailored scissors or cutters can then be used to remove the dead tissue. Various embodiments of such a foreskin cutter are shown below in FIGS. 15A-15D, 16A-16D and 17A-17B. Each of these embodiments enables a necrotic foreskin to be removed simply and safely in a consistent and standardized manner. These factors are relevant for providing a safe and scalable device for bloodless circumcisions on a large scale.

Reference is now made to FIGS. 15A-15D, which are schematic illustrations showing different views of a foreskin cutter, generally referenced 720, constructed and operative in accordance with a further embodiment of the disclosed technique. Identical elements in FIGS. 15A-15D are labeled using identical numbers. Foreskin cutter 720 is used to cut and remove a dead foreskin (not shown) from a penis (not shown) on which the bloodless circumcision device (not shown) of the disclosed technique was applied. FIG. 15A shows foreskin cutter 720 in a side orthogonal view. Foreskin cutter 720 includes two pressure grips 722A and 722B, a connector 724, two inner ring holders 726A and 726B and two cutters 728A and 728B. Connector 724 couples pressure grip 722A with pressure grip 722B. Cutters 728A and 728B are coupled with inner ring holders 726A and 726B respectively. Cutters 728A and 728B may be embodied as small and sharp blades, pins or needles. Alternatively, cutters 728A and 728B may be designed or fabricated from a material suitable to only cut through hardened, dry or dead skin tissue, thereby increasing the safety of foreskin cutter 720 in the event it is accidentally used on live skin tissue. For example, cutters 728A and 728B may be designed having a coarse surface which can cut through dry or dead skin tissue but not through soft, live skin tissue. Inner ring holders 726A and 726B are coupled with pressure grips 722A and 722B and with connector 724. Pressure grips 722A and 722B, connector 724 and inner ring holders 726A and 726B can be fabricated as a single element made from a semi-hard plastic, for example. Foreskin cutter 720 is generally shaped like the Greek letter omega in capital form (Ω), having one side open. Connector 724 is flexible enough that pressure grips 722A and 722B can be pulled in an outward radial direction, shown as arrows 729. Pressure grips 722A and 722B are substantially large enough that a finger can respectively be placed on each one.

Foreskin cutter 720 is used as follows. An inner ring 730, along with a capturing ring 732 are placed around the foreskin (not shown) of a penis (not shown), as described above in various embodiments of the disclosed technique. Once the foreskin has died, foreskin cutter 720 is used to excise the dead foreskin. In FIG. 15A, the location of the penis is such that the penis is inserted into inner ring 730 in the direction of an arrow 723. Therefore, the foreskin located between capturing ring 732 and inner ring holders 726A and 726B, and any excess foreskin located beyond inner ring holders 726A and 726B in the direction of arrow 723, is dead foreskin. Any foreskin located before capturing ring 732 and foreskin cutter 720 is live foreskin. The foreskin therefore extends above and below capturing ring 732. Foreskin cutter 720 is positioned over inner ring 730 by pulling pressure grips 722A and 722B in the direction of arrows 729, positioning inner ring holders 726A and 726B adjacent to inner ring 730 and then releasing the pulling motion on pressure grips 722A and 722B such that inner ring holders 726A and 726B fit around inner ring 730. Optionally, pressure grips 722A and 722B may be compressed inwardly, thereby applying inward radial pressure to inner ring 730 (i.e., in opposite directions of arrows 729). As shown below in FIG. 15B, inner ring holders 726A and 726B are shaped to hold inner ring 730 firmly in place.

As inner ring holders 726A and 726B are positioned adjacent to inner ring 730, cutters 728A and 728B substantially pierce the foreskin (not shown) which is flush against inner ring 730 at sections 734A and 734B of inner ring 730. This is shown more clearly in FIG. 15C. As mentioned above, the foreskin in this area is dead foreskin. Pressure grips 722A and 722B are gripped by two fingers (not shown) and pressure is exerted radially inward towards inner ring 730. By exerting an inward radial pressure, cutters 728A and 728B cut through the foreskin at sections 734A and 734B eventually touching inner ring 730. Using pressure grips 722A and 722B, foreskin cutter 720 is then rotated, thereby enabling cutters 728A and 728B to cut the remainder of the foreskin. Depending on the thickness of the foreskin (not shown), cutters 728A and 728B may not fully pierce the foreskin. In such a scenario, foreskin cutter 720 is rotated while an inward pressure from pressure grips 722A and 722B is exerted, thereby gradually peeling away the dead layers of skin tissue attaching the necrotic foreskin to the penis.

FIG. 15B shows a close-up perspective view of pressure grip 722A and inner ring holder 726A. Inner ring holder 726A includes a cutter 728A, an upper lip 736, a lower lip 738 and a groove 740. Upper lip 736 is substantially larger than lower lip 738 thereby preventing inner ring 730 (FIG. 15A) from sliding past upper lip 736. Upper lip 736 also enables only the distal outer surface of inner ring 730 (in reference to the penis inserted in inner ring 730 in the direction of arrow 723 (FIG. 15A) as shown in FIG. 15A) to be cut by the cutters and not other sections of inner ring 730 or other objects, thereby increasing the safety of foreskin cutter 720. In addition, upper lip 736 adds increased support to the coupling of the inner ring holders to an inner ring. Groove 740 is curved to substantially match at least one of the distal end or the proximal end of inner ring 730. Upper lip 736, lower lip 738 and groove 740 substantially fit into inner ring 730, thereby gripping inner ring 730 and holding it firmly in place. FIG. 15C shows a close-up side orthogonal view of pressure grip 722A and inner ring holder 726A used with inner ring 730. As shown, upper lip 736 prevents inner ring 730 from sliding any further into foreskin cutter 720 in the direction of an arrow 731. When pressure is applied at pressure grip 722A, cutter 728A substantially touches inner ring 730 at section 734A. When used on a penis (not shown), the foreskin (not shown) of the penis is sandwiched between groove 740 and section 734A of inner ring 730. Cutter 728A can thus cut or peel away the foreskin. Cutter 728A does not touch capturing ring 732. FIG. 15D shows foreskin cutter 720 in a perspective view. As shown in FIG. 15D, pressure grips 722A and 722B can be embodied as being slightly concave, thereby facilitating the gripping of the pressure grips via the fingers (not shown). Also as shown, once pressure is applied to pressure grips 722A and 722B and the foreskin (not shown) is pierced, foreskin cutter 720 is rotated in the direction of an arrow 742. As foreskin cutter 720 is rotated in the direction of arrow 742, groove 740 and cutters 728A and 728B (all not shown in FIG. 15D) substantially slide around the outer circumference of inner ring 730. Cutters 728A and 728B substantially cut or peel away the foreskin such that it can be excised. As shown in FIGS. 15A, 15C and 15D, upper lip 736 enables foreskin cutter 720 to only fit around the outer side of inner ring 730 (for example, the areas denoted by sections 734A and 734B). Upper lip 736, lower lip 738 and groove 740 are substantially shaped to match the shape of the outer surface of inner ring 730, thereby increasing the safety of foreskin cutter 720 by substantially enabling cutters 728A and 728B to cut only when inner ring holders 726A and 726B substantially couple with inner ring 730. Hence, the structure of foreskin cutter 720 does not allow it to be mistakenly placed on inner ring 732 or on the inner side of inner ring 730, where skin tissue on the penis may still be alive and healthy. As such, cutters 728A and 728B of foreskin cutter 720 will only cut, peel and remove dead, necrotized foreskin and not living tissue.

Foreskin cutter 720 may be supplied in a kit or can be provided as a supplementary instrument with the bloodless circumcision device of the disclosed technique, including at least an inner ring as described above. In some embodiments, the foreskin cutter cannot cut through foreskin tissue unless coupled with an already deployed inner ring (not shown) such that together the foreskin cutter and the inner ring function as a foreskin tissue holding and removing system.

Figure 16A:
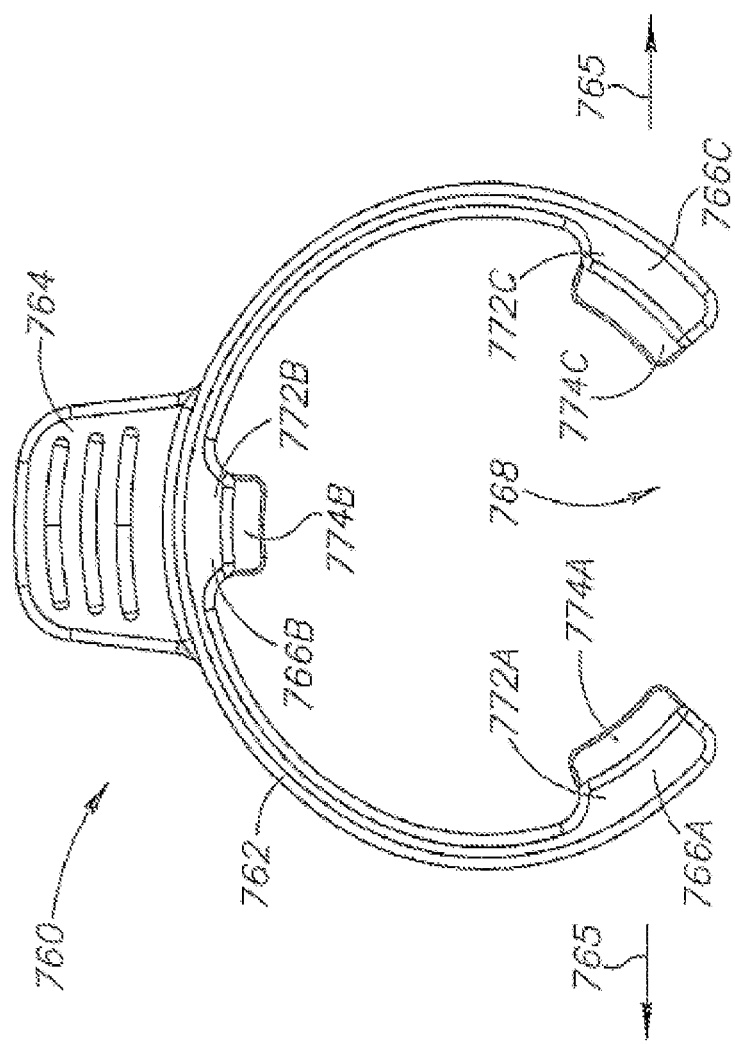

Reference is now made to FIGS. 16A-16D, which are schematic illustrations showing different views of another foreskin cutter, generally referenced 760, constructed and operative in accordance with another embodiment of the disclosed technique. FIG. 16A shows foreskin cutter 760 from a top orthogonal view. Foreskin cutter 760 includes an open ring 762, a grip 764 and inner ring holders 766A, 766B and 766C. Open ring 762 has an opening 768, enabling open ring 762 to be stretched in the direction of arrows 765. Inner ring holders 766A, 766B and 766C each respectively include an upper lip 772A, 772B and 772C and a lower lip 774A, 774B and 774C. As shown, lower lips 774A, 774B and 774C jut out of open ring 762 slightly more than upper lips 772A, 772B and 772C. The areas between the upper lips and the lower lips (not shown in FIG. 16A) respectively form a groove (not shown). Grip 764 is coupled with open ring 762 and is centered on open ring 762. Grip 764 can be gripped by at least two fingers. Inner ring holders 766A, 766B and 766C are coupled with open ring 762 and are evenly spaced around open ring 762. FIGS. 16B and 16C show perspective views of foreskin cutter 760. In FIGS. 16B and 16C, a groove 776 in inner ring holder 766B is visible. Similar grooves exist in inner ring holders 766A and 766C. Centered in groove 776 is a cutter 770. Cutter 770 may be embodied as a pin. Cutter 770 may also be fabricated from a material suitable to only cut through hardened, dry or dead skin tissue, thereby increasing the safety of foreskin cutter 760 in the event it is accidentally used on live skin tissue. Upper lip 772B and lower lip 774B cover cutter 770 thereby preventing cutter 770 from accidentally cutting and damaging skin or an individual while foreskin cutter 760 is handled.

Figure 16D:
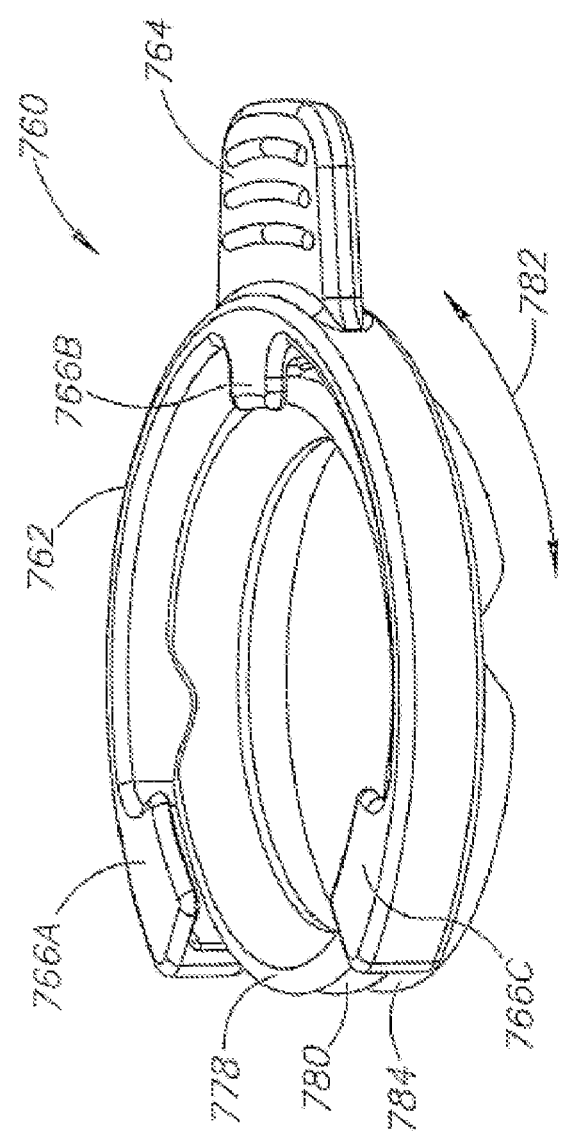

FIG. 16D shows how foreskin cutter 760 is used to excise a dry foreskin (not shown) before it falls off by itself. Unlike foreskin cutter 720 (FIGS. 15A-15D), which was placed vertically over the foreskin, foreskin cutter 760 is place horizontally around the foreskin. FIG. 16D includes an inner ring 778 and a capturing ring 780, which is placed in a circumferential groove 784 of inner ring 778. The diameter of open ring 762 is slightly larger than the diameter of inner ring 778. Once inner ring 778 and capturing ring 780 have been placed on the foreskin and the foreskin has become necrotic, open ring 762 is stretched in the direction of arrows 765 (FIG. 16A) and placed around the upper rim (not shown) of inner ring 778. The grooves in inner ring holders 766A, 766B and 766C firmly fit around the upper rim of inner ring 778. Upper lips 772A-772C and lower lips 774A-774C are shaped to firmly hold the upper rim of inner ring 778 in place and to prevent foreskin cutter 760 from being placed around capturing ring 780, around the lower rim (not shown) of inner ring 778 or from sliding down inner ring 778. Cutter 770 is located in groove 776 such that when foreskin cutter 760 is placed around inner ring 778, cutter 770 pierces the dry foreskin above capturing ring 780. By gripping grip 764, foreskin cutter 760 can be rotated in either direction shown by an arrow 782 around the upper rim of inner ring 778. The groove between upper lips 772A-772C and lower lips 774A-774C, such as groove 776, enable foreskin cutter 760 to be rotated around inner ring 778. By rotating foreskin cutter 760 around inner ring 778, cutter 770 peels and cuts the dry foreskin, substantially excising the foreskin.

It is noted that foreskin cutters 720 (FIGS. 15A-15D) and 760 (FIGS. 16A-16D) can also be used to excise foreskin which is not necrotic but still alive. In such an embodiment, cutters 728A, 728B (FIGS. 15A-15D) and 770 (FIGS. 16A-16D) should be sharp such that they can cut through live skin tissue. This embodiment of the foreskin cutters may be used to excess the foreskin of a penis (not shown) when the foreskin is held, clamped or positioned using a prior art circumcision device.

Figure 17B:
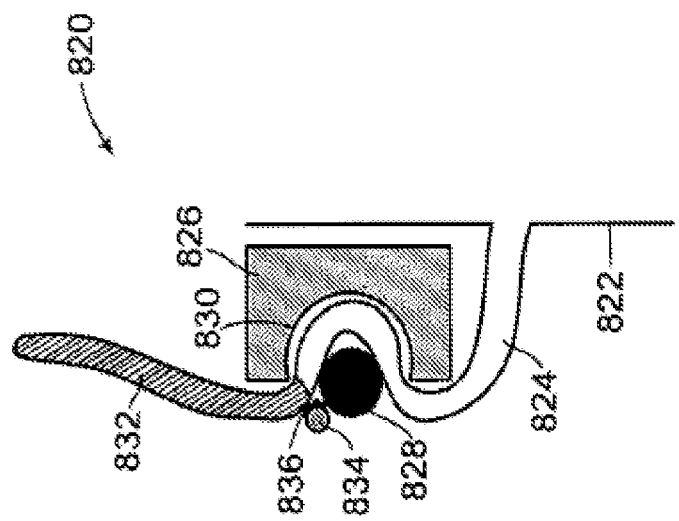
FIGS. 17A-17B are schematic illustrations showing a further foreskin cutter, constructed and operative in accordance with a further embodiment of the disclosed technique.
Figure 17A:
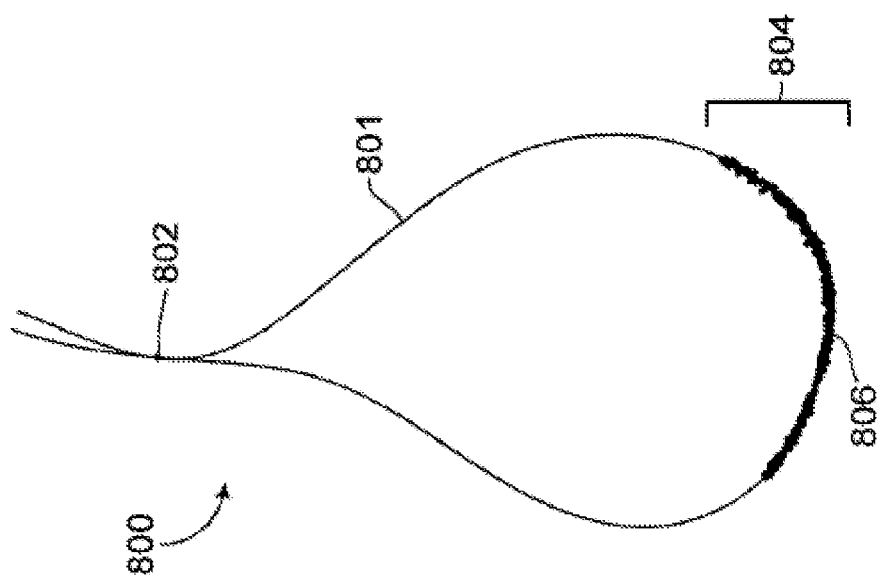

Reference is now made to FIGS. 17A-17B, which are schematic illustrations showing a further foreskin cutter, generally referenced 800 and 820 respectively, constructed and operative in accordance with a further embodiment of the disclosed technique. FIG. 17A shows a foreskin cutter 800, substantially constructed from a suture string 801. The suture string 801 is either knotted or glued at a point 802, thereby forming a teardrop shape. Suture string 801 can be knotted or glued to form other closed shapes as is obvious to one skilled in the art. Suture string 801 includes a roughened section 806. Roughened section 806 may be sharp, toothed, abrasive and the like. As shown, roughened section 806 forms only a part of suture string 801, depicted in FIG. 17A as a section 804. Roughened section 806 is substantially opposite point 802. The diameter of suture string 801 is larger than the diameter of an inner ring.

FIG. 17B shows how the foreskin cutter of FIG. 17A is used to excise a dry and dead foreskin. FIG. 17B shows a side orthogonal view of the bloodless circumcision device used on a penis (not shown). The penis includes a shaft 822 and a foreskin 824. An inner ring 826 is placed around shaft 822 between shaft 822 and foreskin 824. Foreskin 824 is inserted into a circumferential groove 830 of inner ring 826. A capturing ring 828 is then placed around circumferential groove 830, thereby causing controlled ischemic necrosis to a portion of foreskin 824. After a period of a few hours, the portion of foreskin 824 above capturing ring 828, shown as a necrotic portion 832, begins to die. After a period of a few days, necrotic portion 832 is completely dead and dry. Once necrotic portion 832 is completely dry, a foreskin cutter 834, similar to foreskin cutter 800 (FIG. 17A), is placed around foreskin 824 at the base of necrotic portion 832. Foreskin cutter 834 is substantially a closed shape suture string have a roughened portion 836. Roughened portion 836 is placed against the base of necrotic portion 832 and foreskin cutter 834 is pulled such that roughened portion 836 abuts against the base of necrotic portion 832. Foreskin cutter 834 is then rotated horizontally around shaft 822. As foreskin cutter 834 is rotated around, roughened portion 836 substantially abrades and peels through necrotic portion 832, thus excising the necrotic portion of the foreskin.

Reference is now made to FIGS. 18A-18D, which are schematic illustrations showing a capturing ring deployment system, generally referenced 850, constructed and operative in accordance with another embodiment of the disclosed technique. Capturing ring deployment system 850 includes a ring holder 852, a capturing ring 854 and an inner ring 856. Inner ring 856 includes a circumferential groove 858. Ring holder 852 includes three flanges 860A, 860B and 860C. Each of flanges 860A-860C respectively includes a raised edge 862A, 862B and 862C as well as a resting surface 864A, 864B and 864C. Ring holder 852 is substantially annular in shape having an opening 853. Ring holder 852 can be constructed as other closed shapes and is a matter of design choice. For example, ring holder 852 can be shaped as a convex polygon. In general, ring holder 852 has a diameter which is larger than inner ring 856 and capturing ring 854, although in other embodiments of the disclosed technique, ring holder 852 has a diameter which is substantially at least equal to a diameter of a shaft of a penis (not shown). If ring holder 852 has a convex polygonal shape, then the diameter of an inscribed circle in the polygonal shape should be at least equal to a diameter of the shaft of the penis. Flanges 860A-860C are evenly spaced around ring holder 852. Ring holder 852 may optionally include more than three flanges (not shown). Raised edges 862A-862C extend from resting surfaces 864A-864C on the inner side of ring holder 852. Ring holder 852 is used to hold capturing ring 854 in a stretched state while inner ring 856 is positioned around a penis (not shown). Ring holder 852 is also used to aid in positioning inner ring 856 at its desired position around the penis, when capturing ring 854 in its stretched state substantially couples ring holder 852 to inner ring 856. Ring holder 852 is further used to transfer capturing ring 854 in its stretched state to circumferential groove 858 when inner ring 856 has been properly positioned. FIGS. 18A-18D show the various stages of how capturing ring deployment system 850 is used.

Figure 18A:
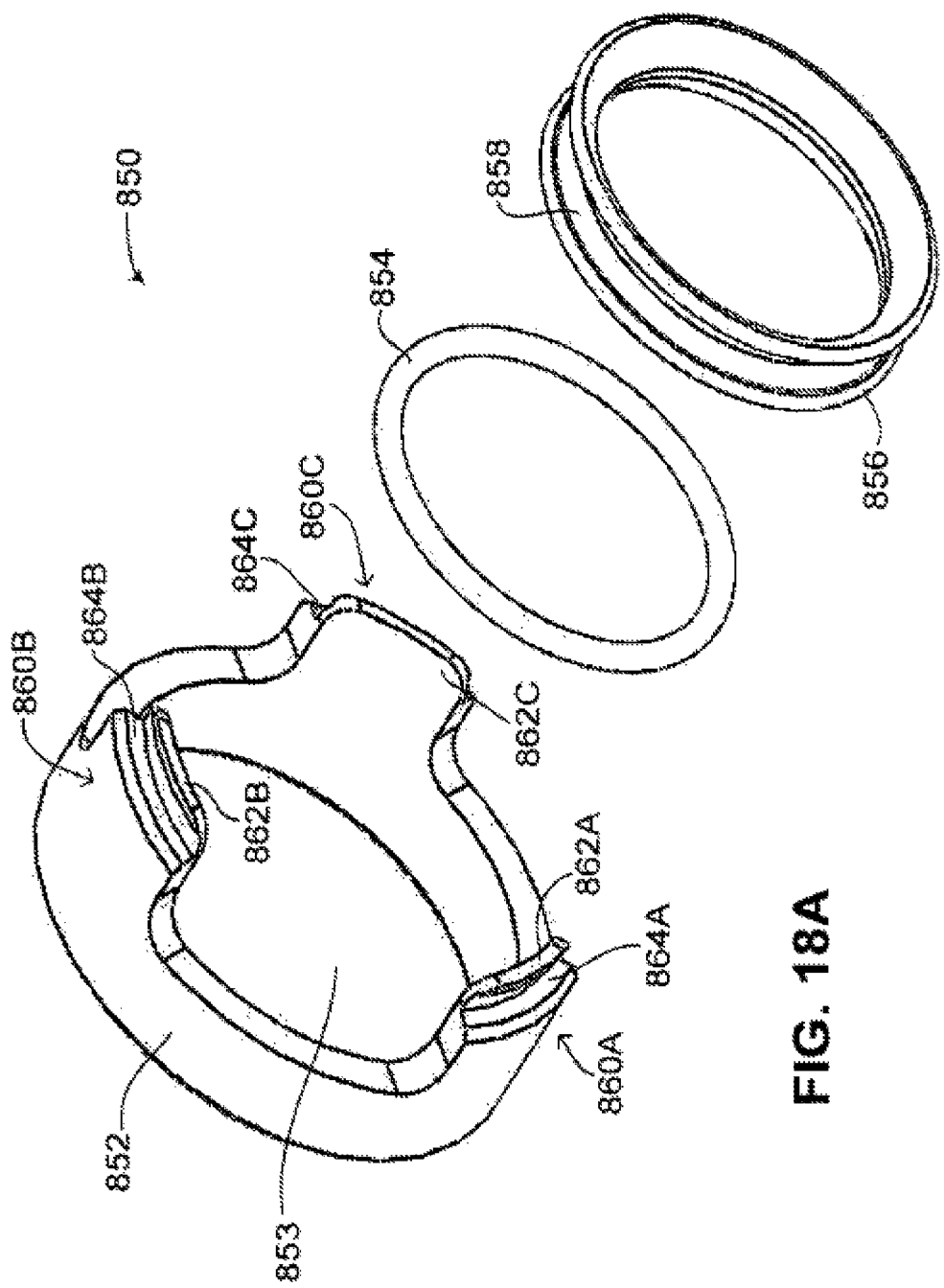
FIGS. 18A-18D are schematic illustrations showing a capturing ring deployment system, constructed and operative in accordance with another embodiment of the disclosed technique.
Figure 18B:
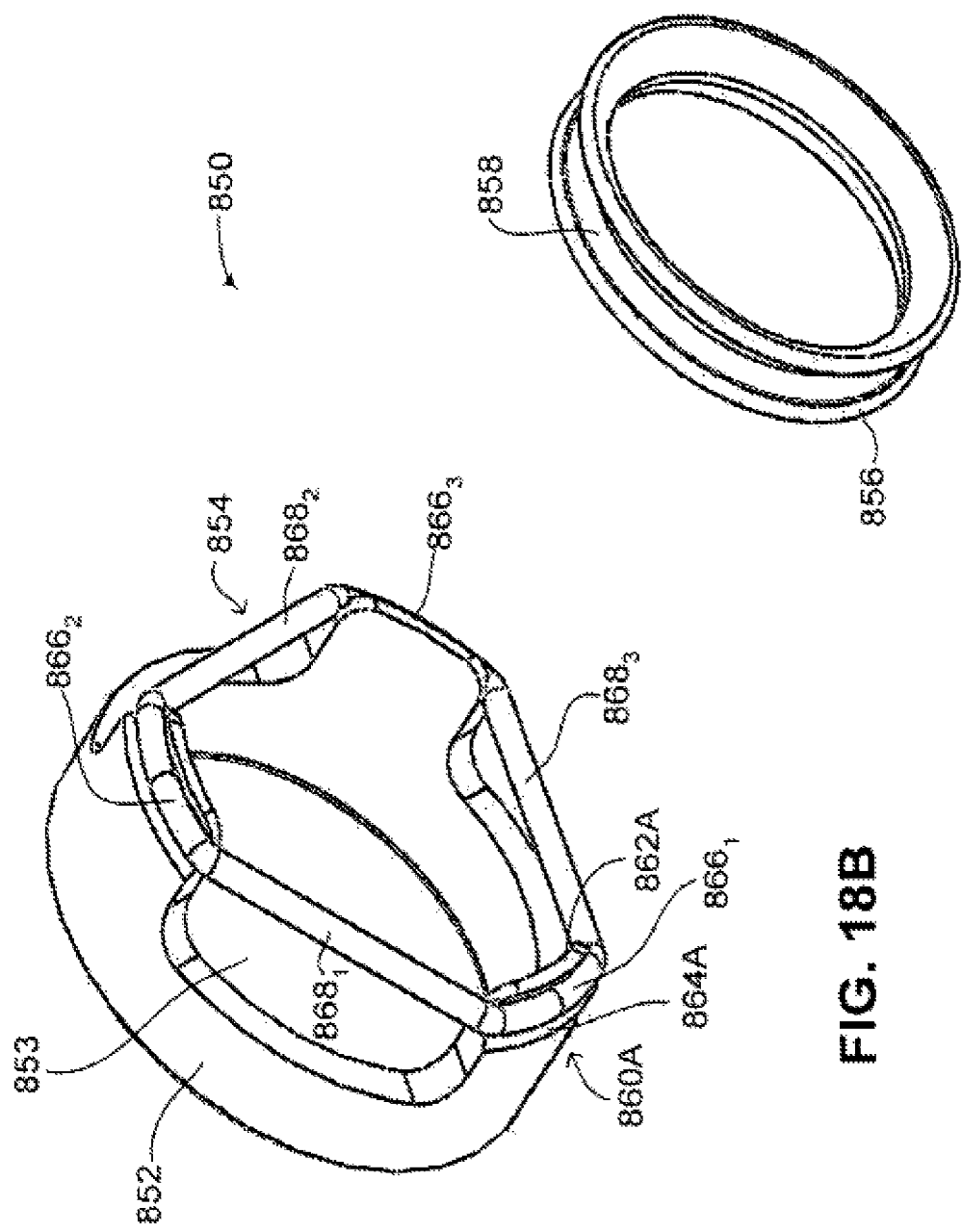

In FIG. 18A, the various elements of capturing ring deployment system 850 are shown as separate elements. In FIG. 18B, capturing ring 854 is stretched around flanges 860A-860C. In its stretched state, capturing ring 854 rests on the resting surfaces of ring holder 852, such as resting surface 864A. The raised edges of ring holder 852, such as raised edge 862A, retain capturing ring 854 in its stretched state. Due to the position and number of flanges 860A-860C, when capturing ring 854 is stretched around the flanges, capturing ring 854 assumes a substantially triangular shape. If ring holder 852 included four flanges (not shown), then when capturing ring 854 would be stretched around the flanges, capturing ring 854 might assume a square shape (not shown), a trapezoid shape (not shown) or a quadrilateral shape (not shown) depending on the relative positions of the flanges. Accordingly, a plurality of more than three flanges can be located on ring holder 852 thereby giving capturing ring 854 a convex polygonal shape, depending on the number and relative positions of the flanges. As shown, when stretched around the flanges, three sections of capturing ring 854, sections $866_1$, $866_2$ and $866_3$ rest on the resting surfaces, representing vertex-like sections of capturing ring 854. The remaining sections of capturing ring 854, shown as edge sections $868_1$, $868_2$ and $868_3$ become taut and represent edge-like sections of capturing ring 854. As described in greater detail in FIG. 18C, the relative distances between edge sections $868_1$, $868_2$ and $868_3$ are such that the diameter of inner ring 856 is slightly larger than the diameter of an inscribed circle in capturing ring 854 in its stretched state.

Figure 18C:
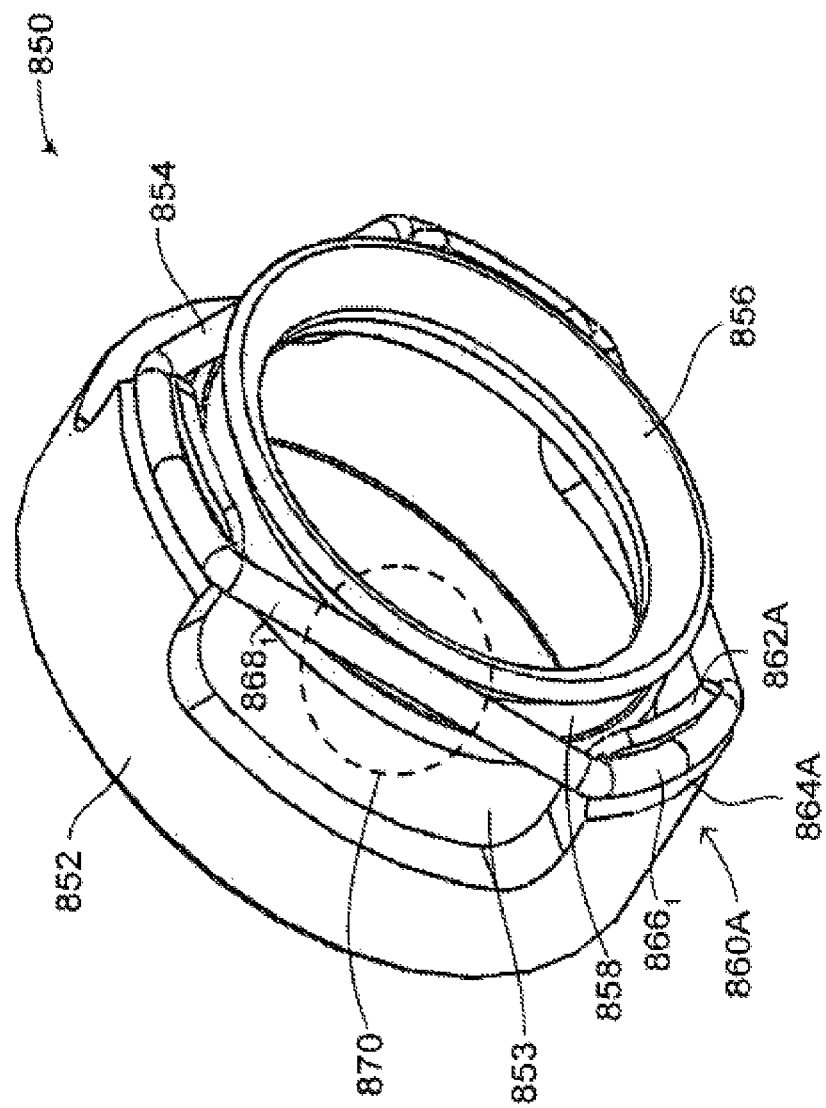
Figure 18D:
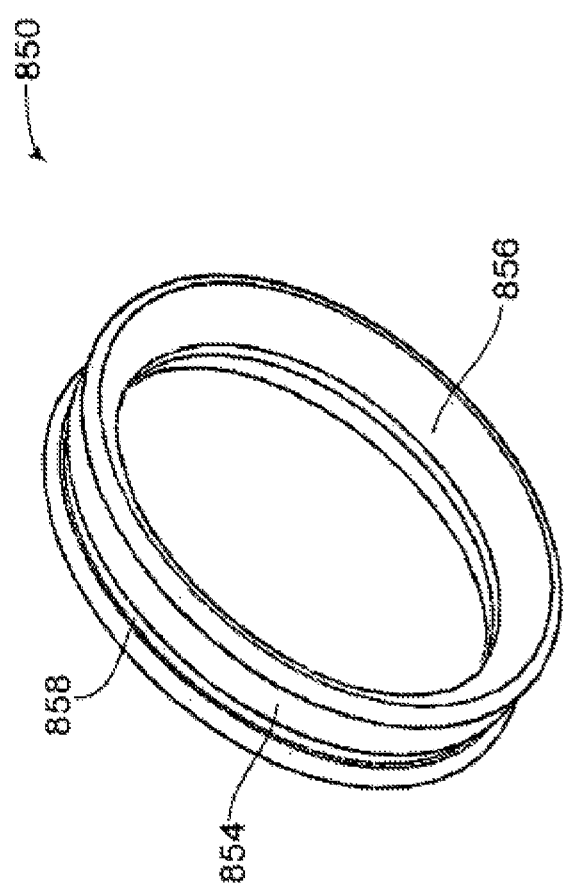

In FIG. 18C, inner ring 856 is placed within ring holder 852 and capturing ring 854 such that the edge sections of capturing ring 854, such as edge section $868_1$, are positioned within circumferential groove 858. Since the diameter of inner ring 856 is slightly larger than the diameter of an inscribed circle in capturing ring 854 in its stretched state, capturing ring 854 clasps inner ring 856. Inner ring 856 is held by capturing ring 854 at three positions along the edge sections of capturing ring 854 due to the presence of three flanges on ring holder 852. One such position is shown in FIG. 18C by a dotted circle 870 (the other two are not visible in FIG. 18C). The pressure exerted by the edge sections of capturing ring 854 on inner ring 856 is strong enough such that if capturing ring deployment system 850 as shown in FIG. 18C were placed around the shaft of a penis (not shown), displacement of inner ring 856 would cause capturing ring 854 and ring holder 852 to displace respectively. In FIG. 18C, ring holder 852, capturing ring 854 and inner ring 856 are substantially coupled together by inward radial compression forces (not shown) of capturing ring 854 on flanges 860A, 860B (not shown in FIG. 18C) and 860C (not shown in FIG. 18C) and on sections of inner ring 856, such as the section shown by dotted circle 870, thereby forming a single moveable unit. Capturing ring deployment system 850 as shown in FIG. 18C can be positioned over the penis at a desired position. At the desired position, ring holder 852 is held, for example by the hand or an element and the sections where inner ring 856 and capturing ring 854 touch (as denoted by dotted circle 870) are also held, for example by another hand or another element. Ring holder 852 is then pulled in a direction away from inner ring 856 and inner ring 856 and capturing ring 854 are optionally pulled in the opposite direction away from ring holder 852, thereby releasing capturing ring 854 from flanges 860A-860C. Capturing ring 854 is then positioned within circumferential groove 858, as shown in FIG. 18D.

Reference is now made to FIGS. 19A-19K, which are schematic illustrations showing the method of use of the capturing ring deployment system of FIGS. 18A-18D with a bloodless circumcision device, constructed and operative in accordance with a further embodiment of the disclosed technique. Identical elements in FIGS. 19A-19K are labeled using identical numbers. FIGS. 19A-19K show the various steps of using the bloodless circumcision device of the disclosed technique with the capturing ring deployment system of FIGS. 18A-18D, each step demonstrating how the capturing ring deployment system and the bloodless circumcision device are applied to the penis of an individual to circumcise the individual.

Figure 19K:
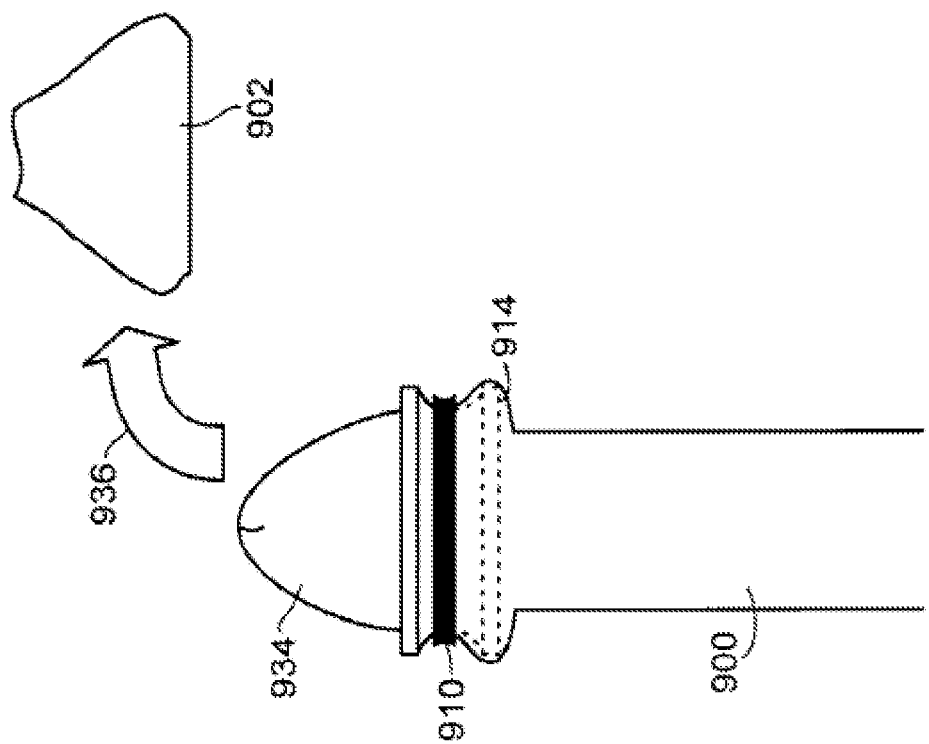

A first step is shown in FIG. 19A. FIG. 19A shows a penis (not labeled) which includes a shaft 900, a foreskin 902 and a foreskin opening 904. In this step, a line, such as a dotted line 906, is marked on foreskin 902 where the individual desires to have his penis circumcised. Dotted line 906 is substantially located on foreskin 902 and not on shaft 900. Dotted line 906 is marked with non-toxic marker for example. After dotted line 906 is marked, a size selector, such as shown below in FIG. 20, for determining the appropriate size of a bloodless circumcision device to be used on the individual is used to determine to correct size capturing ring and inner ring to be used on the individual. This step is not depicted in FIGS. 19A-19K. In an alternative to this step, a variable sized inner ring (not shown) may be used and set to a desired size after measurement of the penis or upon deployment of the inner ring, as shown below in FIG. 19D, over the penis. A second step is shown in FIG. 19B. In this step, the selected capturing ring, shown in FIG. 19B as a capturing ring 910, is stretched around a ring holder, shown in FIG. 19B as a ring holder 908. Ring holder 908 and capturing ring 910 substantially represent a capturing ring deployment system and are herein referred to as such in FIGS. 19A-19K. This is not depicted in FIG. 19B. Ring holder 908 and capturing ring 910 are then placed over foreskin 902 and shaft 900. Ring holder 908 and capturing ring 910 are placed far enough along shaft 900 that foreskin 902 can be fully folded back onto shaft 900 without touching the ring holder. A third step is shown in FIG. 19C. In this step, opening 904 of foreskin 902 is stretched open, shown by an arrow 912. Foreskin 902 may be stretched open using the hands or using various instruments such as clamps, clasps, tongs or known surgical tools. In an alternative to this step, foreskin 902 may be pulled back over shaft 900 (not shown), as was shown above in FIG. 2B.

A fourth step in shown in FIG. 19D. In this step, the selected inner ring, shown in FIG. 19D as an inner ring 914, which includes a circumferential groove 916, is inserted around the glans (not shown) of the penis via opening 904, which is still held stretched open, as depicted by an arrow 918. Alternatively, inner ring 914 may be directly placed over the glans of the penis if foreskin 902 is pulled back over shaft 900. In one embodiment of the disclosed technique, inner ring 914 may be inserted through opening 904 vertically such that an end section 915 of inner ring 914 touches the glans of the penis (not shown) or the corona of the glans of the penis (not shown). The inner ring is then rotated to a horizontal position, as depicted in FIGS. 19D and 19E, placing it over the glans of the penis, substantially around the corona of the glans of the penis. A fifth step is shown in FIG. 19E. In this step, inner ring 914 is maneuvered around the glans of the penis until the centerline of circumferential groove 916, depicted as a centerline 920 in FIG. 19E, is substantially lined up with dotted line 906. As shown, opening 904 is no longer held stretched open. Also, as shown in FIG. 19E, centerline 920 does not need to necessarily line up exactly with dotted line 906 in this step. For purposes of clarity, inner ring 914, circumferential groove 916 and centerline 920 are shown as dotted line. In an alternative to this step, if foreskin 902 was pulled back along shaft 900, in this step, foreskin 902 is pulled over inner ring 914, either using the hands or an instrument. Inner ring 914 would then be maneuvered to its desired position as described above. A sixth step is shown in FIG. 19F. In this step, the capturing ring deployment system, including ring holder 908 and capturing ring 910, is moved along shaft 900 in the direction of an arrow 922 such that capturing ring 910 firmly grasps circumferential groove 916 of inner ring 914, through foreskin 902, at a plurality of points or sections along the circumference of inner ring 914. This was shown in greater detail above in FIG. 18C. Ring holder 908, capturing ring 910 and inner ring 914 are now all coupled together as a single unit via inward radial compression forces (not shown) of capturing ring 910. As can be seen, the diameter of ring holder 908 and the stretched diameter of capturing ring 910 are larger than the diameters of shaft 900 and the area of the penis around foreskin 902. In addition, dotted line 906 is still not lined up exactly with centerline 920 (not visible in FIG. 19F).

A seventh step is shown in FIG. 19G. In this step, the capturing ring deployment system, depicted as a section 926, which now includes inner ring 914, capturing ring 910 and ring holder 908, can be moved as a single unit in the direction of arrows $924_1$ or $924_2$ (i.e., distally or proximally along shaft 900) to align centerline 920 (not visible in FIG. 19G) of circumferential groove 916 with dotted line 906 (not visible in FIG. 19G). Alternatively, foreskin 920 may be pulled in the direction of arrows $924_1$ or $924_2$ to align centerline 920 with dotted line 906. As shown, capturing ring 910 clasps circumferential groove 916 with sufficient force such that foreskin 902 can be pulled distally or proximally along shaft 900 without dislodging capturing ring 910 from ring holder 908. In addition, the capturing ring deployment system grips foreskin 902 tight enough such that foreskin 902 remains compressed between inner ring 914 and capturing ring 910 even while the capturing ring deployment system is moved along the penis, yet not so tight that movement of the capturing ring deployment system would dislodge capturing ring 910 from ring holder 908. An eighth step is shown in FIG. 19H. In this step, ring holder 908 is pulled in the direction shown by arrows 930 while capturing ring 910 and inner ring 914 are held in place. Optionally, capturing ring 910 and inner ring 914 may be slightly pulled in a direction opposite the direction of arrows 930. This motion dislodges capturing ring 910 from flanges 928 of ring holder 908, which are visible in FIG. 19H, thereby positioning capturing ring 910 within circumferential groove 916. Capturing ring 910 now applies a compression force against inner ring 914, thereby compressing foreskin 902 at dotted line 906 (not visible in FIG. 19H). A ninth step is shown in FIG. 19I. In this step, ring holder 908 is removed from shaft 900 in the direction of an arrow 932. Since ring holder 908 has a diameter larger than the widest point along the penis, ring holder 908 can be easily removed from the penis once capturing ring 910 has been placed on inner ring 914.

Figure 19J:
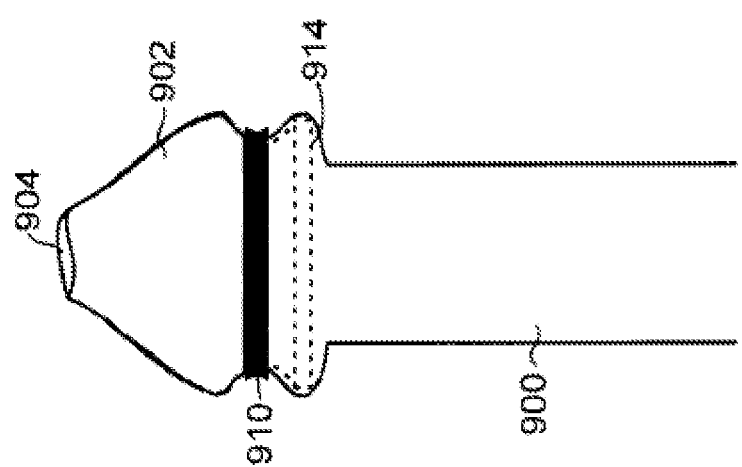

A tenth step is shown in FIG. 19J. In this step, after a few hours, foreskin 902 begins to discolor and dry up as necrosis of the foreskin sets in. After a few days, foreskin 902 is dead and dry. An eleventh step is shown in FIG. 19K. In this step, after a few days and death of the foreskin, foreskin 902 is excised from the penis, as shown by an arrow 936, thereby revealing a glans of the penis 934. Foreskin 902 may naturally fall off or may be excised using any of the foreskin cutters of the disclosed technique described above in FIG. 15A-15D, 16A-16D or 17A-17B, or by using other devices for removing the foreskin, such as a pair of scissors or a scalpel. It is noted that inner ring 914 and capturing ring 910 as shown in FIGS. 19A-19K can be embodied using any of the embodiments of inner rings and capturing rings disclosed according to the disclosed technique. Once foreskin 902 has been excised, inner ring 914 and capturing ring 910 can be removed, for example by using a pairs of scissors to cut capturing ring 910 at which point inner ring 914 can be released from the remaining foreskin (not labeled in FIG. 19K) and removed from the penis.

Reference is now made to FIG. 20, which is a schematic illustration of size selector for determining the appropriate size of a bloodless circumcision device to be used on an individual, generally referenced 950, constructed and operative in accordance with another embodiment of the disclosed technique. Size selector 950 includes a plurality of holes 952A, 952B, 952C, 952D, 952E, 952F and 952G. Each one of holes 952A-952G represents a different size inner ring of the bloodless circumcision device of the disclosed technique and may be labeled by letters, numerals, symbols and the like. The holes in size selector 950 are labeled using the Latin letters A-G, for example. In general, size selector 950 is used by placing the flaccid penis (not shown) of an individual through holes 952A-952G. In general, the smallest which the flaccid penis can be inserted through easily represents the size of the inner ring to be used on that individual. Size selector 950 is shaped as a circle although other shapes are possible. In addition, size selector 950 may include more holes or fewer holes than depicted in FIG. 20.

As described above in FIGS. 2A-2E and 19A-19K, an inner ring of the disclosed technique is placed around the corona of the glans of the penis, substantially around the sulcus formed between the corona of the glans of the penis and the area where the foreskin is attached to the shaft of the penis. One method for placing the inner ring around the corona of the glans of the penis involves pulling the foreskin back along the shaft of the penis, thereby exposing the glans. The inner ring is then placed and the foreskin is pulled over the inner ring. This procedure was shown above in FIGS. 2B and 2C. Another method for placing the inner ring around the corona of the glans of the penis involves stretching the opening of the foreskin and inserting the inner ring through the foreskin over the glans of the penis, and maneuvering the inner ring to its marked position, substantially around the corona of the glans of the penis. This was shown above in FIGS. 19C-19E. In certain individuals it may be difficult to pull the foreskin over the inner ring or to insert the inner ring via the opening of the foreskin when a rigid inner ring is used. With such individuals, a flexible inner ring may be used, which may simplify the placement of the inner ring around the corona of the glans of the penis as well as the pulling of the foreskin around the inner ring. In addition, a varying diameter inner ring may be used, wherein the diameter of the inner ring can be reduced while the inner ring is positioned around the corona of the glans of the penis. Once placed, the diameter of the inner ring can be increased to a desirable size. Flexible inner ring embodiments are shown below in FIGS. 21A-21G.

Figure 21B:
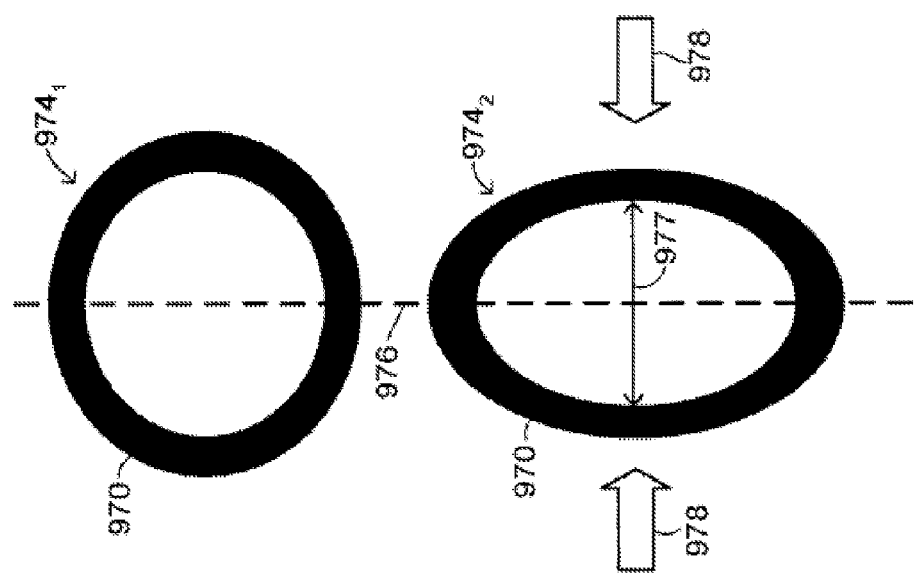
FIGS. 21A-21G are schematic illustrations of flexible inner ring shapes and configurations for use with a bloodless circumcision device, constructed and operative in accordance with a further embodiment of the disclosed technique.
Figure 21A:
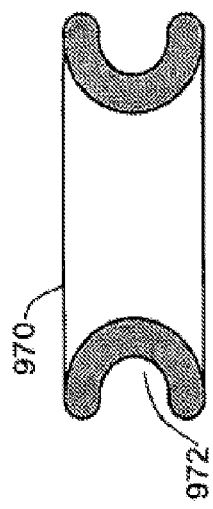

Reference is now made to FIGS. 21A-21G, which are schematic illustrations of flexible inner ring shapes and configurations for use with a bloodless circumcision device, constructed and operative in accordance with a further embodiment of the disclosed technique. The flexible inner ring shapes in FIGS. 21A-21G can also be referred to as semi-rigid inner ring shapes, as they can be somewhat deformed by applying an external force, yet cannot be deformed to the extent that capturing rings of the disclosed technique can be deformed. Reference is now made in particular to FIGS. 21A and 21B. FIG. 21A shows an inner ring 970, including a circumferential groove 972, in a cross sectional view. Inner ring 970 is flexible and can be deformed upon applying an external force, as shown in FIG. 21B. The external force may be applied manually and should be substantially high to prevent inner ring 970 from deforming unintentionally. Once the external force is removed, inner ring 970 will return to its original shape. FIG. 21B shows inner ring 970 from a top orthogonal view. FIG. 21B shows inner ring 970 in two states. In a relaxed state 974₁, when no external pressure is applied to inner ring 970, inner ring 970 assumes a circular shape. In a compressed state 974₂, when an external pressure is applied to the sides of inner ring 970, shown by arrows 978, inner ring 970 assumes an elongated, elliptical-like shape. When the external pressure shown by arrows 978 is removed, inner ring 970 assumes its relaxed state. As shown in reference to a centerline 976, in the compressed state, the diameter of inner ring 970 along its minor axis, shown by an arrow 977, is smaller than the diameter of inner ring 970 in its relaxed state. Inner ring 970 may be constructed such that in a relaxed state its diameter can be compressed up to a predetermined percentage of its length. For example, the diameter of inner ring 970 along its minor axis may be able to be shortened by 30-40% in a fully compressed state. Inner ring 970 can be manufactured from flexible materials such as silicone, EPDM rubber and nitrile rubber (as known as NBR). Inner ring 970 may also include a core flexible metal or a ring of material embedded within the surface of inner ring 970, as described below in FIGS. 21C-21G. Inner ring 970 may be placed in its compressed state by compressing the sides of inner ring 970 with the fingers or with an instrument, such as forceps or tweezers. In its compressed state, since inner ring 970 has a significantly smaller diameter along its minor axis, inner ring 970 may be more easily inserted through the opening of the foreskin (not shown). Once placed inside the foreskin and around the glans of the penis (not shown), the external pressure on inner ring 970 is removed and inner ring 970 then resumes its relaxed state. Inner ring 970 may then be maneuvered around the glans of the penis until it positioned at its desired location.

Inner ring 970 can also be embodied as a spring in either its axial direction or circumferential direction, similar to capturing rings 300 (FIG. 7A) and 330 (FIG. 7D). In such an embodiment, the diameter of the inner ring can be shortened by applying a concentric inward radial force, for example, using the fingers or by using an instrument for applying uniform pressure around an inner ring, as described below in reference to FIGS. 21C-21G. With the diameter shortened, the foreskin of the penis may be more easily pulled over the inner ring, at which point, the radial force is removed and the inner ring returns to its larger, expanded state diameter.

Figure 21C:
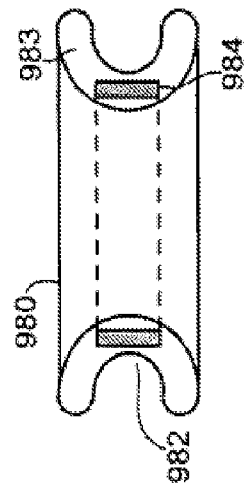
Figure 21D:
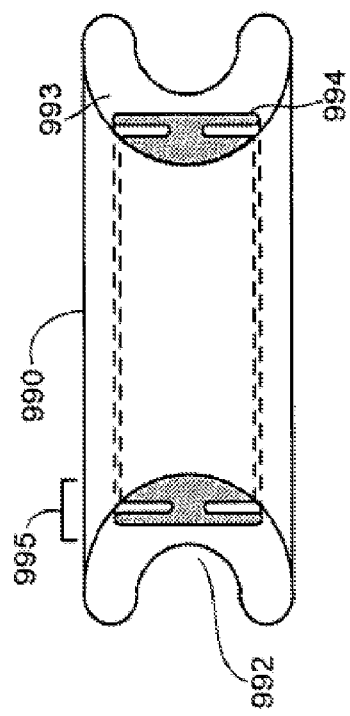

A flexible inner ring according to the disclosed technique can also be manufactured from a plurality of materials and elements. As each selected element, material or both may have different mechanical properties, physical properties and uses, specific elements and materials can be selected and combined to provide a flexible inner ring having specific characteristics. This is a matter of design choice and is known to the worker skilled in the art. Examples of composite material flexible inner rings are shown in FIGS. 21C-21G. Reference is now made to FIGS. 21C-21G which show four example embodiments of composite material flexible inner rings. FIGS. 21C-21F show the inner rings in cross sectional views whereas FIG. 21G shows the inner ring of FIG. 21F in a perspective view. Each of the inner rings shown in FIGS. 21C-21G is substantially circular in shape. In FIG. 21C, an inner ring 980, including a circumferential groove 982 is shown. Inner ring 980 is composed of two materials, a first material 983 and a second material 984. Second material 984 is completely contained within first material 983. In FIG. 21C, second material 984 is manufactured in the shape of a vertical ring, placed within first material 983. It is obvious to a worker skilled in the art that other types of shapes for second material 984 are possible and are a matter of design choice. In FIG. 21D, an inner ring 990, including a circumferential groove 992 is shown. Inner ring 990 is composed of two materials, a first material 993 and a second material 994. Second material 994 is coupled with first material 993, where the inner side of inner ring 990 is composed of second material 994 and the outer side of inner ring 990 is composed of first material 993. In FIG. 21D, second material 994 is manufactured in the shape of a ring having a modified finger joint (shown as a section 995 in FIG. 21D) coupling it with first material 993. It is obvious to a worked skilled in the art that other types of shapes and joints are possible for second material 994.

Figure 21E:
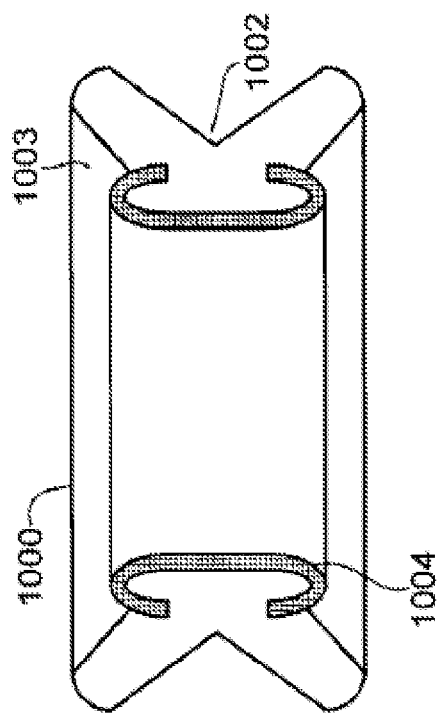
Figure 21G:
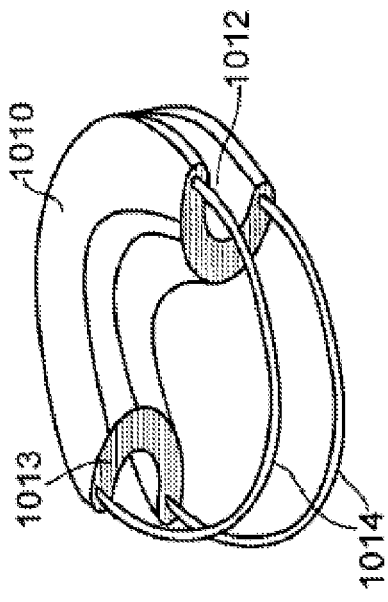
Figure 21F:
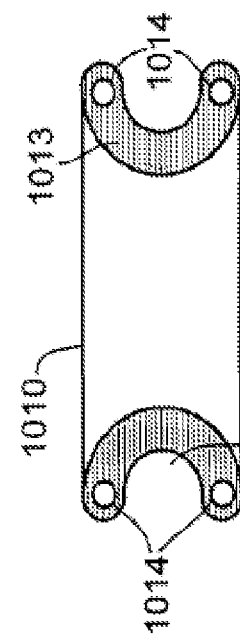

In FIG. 21E, an inner ring 1000, including a circumferential groove 1002 is shown. Inner ring 1000 is composed of two materials, a first material 1003 and a second material 1004. Second material 1004 is coupled with first material 1003, where the inner side of inner ring 1000 is composed of second material 1004 and the outer side of inner ring 1000 is composed of first material 1003. In FIG. 21E, second material 1004 is manufactured in the shape of a C-ring. First material 1003 is manufactured such that the C-shape of second material 1004 can be coupled with it. It is obvious to a worked skilled in the art that other types of shapes are possible for second material 1004 and first material 1003. In FIG. 21F, an inner ring 1010, including a circumferential groove 1012 is shown. Inner ring 1010 is composed of two materials, a first material 1013 and a second material 1014. Second material 1014 is completely contained within first material 1013. In FIG. 21F, second material 1014 is manufactured in the shape of two horizontal rings, placed within first material 1013. It is obvious to a worker skilled in the art that other types of shapes for second material 1014 are possible and are a matter of design choice. In FIG. 21G, the ring-like shape of second material 1014 is shown more clearly in a perspective view. It is obvious to a worker skilled in the art that second material 1014 could be embodied as a single ring, as a plurality of rings and as other shapes, all of which are a matter of design choice.

In the embodiments shown in FIGS. 21C-21G, the outer areas of the inner rings are made from a soft flexible material, shown above as the first material. The inner rings are given strength and semi-rigidity by embedding a stiffer material within the soft flexible material, shown above as the second material. Whereas the second material is stiffer than the first material, the second material is substantially still a flexible, spring-like material. The composition of the two materials enables the inner rings to be deformed upon the application of an external pressure. Once the external pressure is removed, the inner rings regain their original shape. An external pressure can be applied to opposing sides of the inner rings, such as shown above in FIG. 21B, thereby shortening the diameter of the inner rings along their respective minor axes. This may ease the inserting of the inner ring through the opening of the foreskin. An external pressure can also be applied uniformly, or concentrically around the sides of the inner rings, thereby retaining their circular shape but reducing their overall diameter. Uniform pressure may be applied by using an instrument having two hemispherical members, such as forceps or tweezers having hemispherical ends that meet to form a circle when the grips of the forceps or tweezers are brought together. In the case of the foreskin being pulled down, reducing the overall diameter of an inner ring may simplify pulling the foreskin over the inner ring. Once the foreskin has been pulled over the inner ring, the external pressure is removed and the inner ring returns to its longer, relaxed state diameter. Each of first materials 983, 993 and 1003 can be embodied as an elastomer, such as silicone or EPDM rubber, for example. Each of second materials 984, 994, 1004 and 1014 can be embodied as a spring-like flexible plastic, such as polyether ether ketone (also known as PEEK), polycarbonate or polypropylene, for example. Each of second materials 984, 994, 1004 and 1014 can also be embodied as a spring-like metal, such as grade 304 stainless steel, flexible steel, Nitinol or any other shape memory alloy, for example. In the case of inner ring 1010, second material 1014 can also be embodied as a spring-like flexible plastic, such as PEEK or polycarbonate. In general, the materials used for inner rings 970, 980, 990, 1000 and 1010 should be selected in appropriate percentages such that the pressure from a capturing ring (not shown) placed around such flexible inner rings does not cause the flexible inner rings to deform or to contract and shorten in diameter. For example, if the capturing ring exerts a compression pressure of 0.5-10 atmospheres, which may be above the required pressure for causing necrosis in skin tissue but less than the pressure at which an individual will feel pain, then the flexible inner rings shown in FIGS. 21-21G should be able to maintain their relaxed, or expanded states, up to pressures of approximately 3 atmospheres.

Figure 22B:
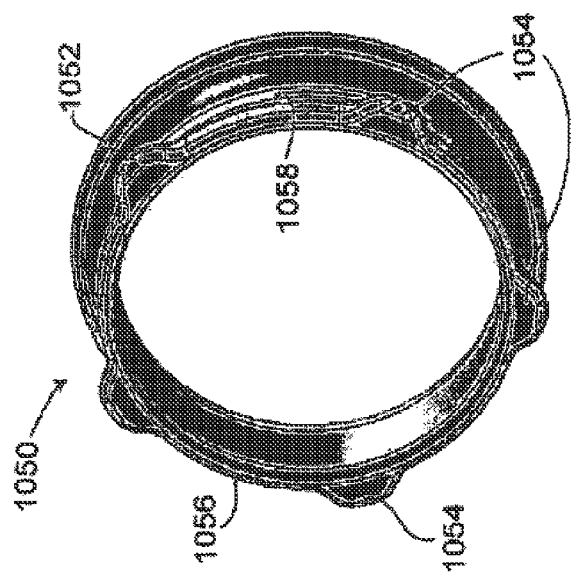
Figure 22D:
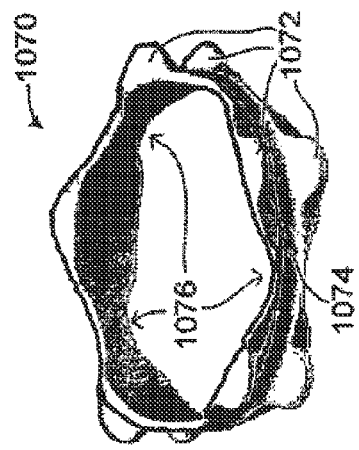
Figure 22A:
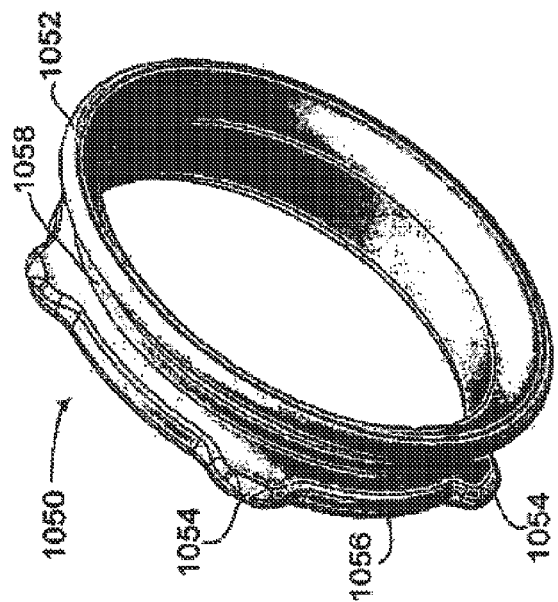

Reference is now made to FIGS. 22A-22G, which are schematic illustrations of other inner ring shapes and configurations for use with a bloodless circumcision device, constructed and operative in accordance with a further embodiment of the disclosed technique. FIGS. 22A and 22B show a first inner ring shape, generally referenced 1050, and FIGS. 22C-22G show a second inner ring shape, generally referenced 1070. Reference is now made to FIGS. 22A and 22B which show two perspective illustrations of first inner ring shape 1050. First inner ring shape 1050 includes a lip 1052, a plurality of protrusions 1054, a plurality of troughs 1056 and a circumferential groove 1058. Lip 1052 substantially forms the circumference of one end of first inner ring shape 1050 whereas plurality of protrusions 1054 and plurality of troughs 1056 substantially form the circumference of the other end of first inner ring shape 1050. Circumferential groove 1058 is located between lip 1052 and plurality of protrusions 1054 and plurality of troughs 1056. Each one of plurality of troughs 1056 is located between two subsequent ones of plurality of protrusions 1054. Plurality of protrusions 1054 and plurality of troughs 1056 are spaced around the circumference of first inner ring shape 1050.

First inner ring shape 1050 is placed on a penis (not shown) such that lip 1052 is proximal to the base of the penis and plurality of protrusions 1054 and plurality of troughs 1056 are distal to the base of the penis. When first inner ring shape 1050 is used with the bloodless circumcision device of the disclosed technique (not shown), first inner ring shape 1050 is placed around the glans (not shown) or corona (not shown) of the penis. A foreskin (not shown) is then pulled over first inner ring shape 1050 and then a capturing ring (not shown) is positioned over the foreskin over the area of circumferential groove 1058. As mentioned above, first inner ring shape 1050 is positioned on the penis such that after a few days, the portion of the foreskin over lip 1052 is substantially live tissue whereas the portion of the foreskin over plurality of protrusions 1054 and plurality of troughs 1056 is necrotic. Due to the configuration of plurality of protrusions 1054 and plurality of troughs 1056, an instrument used to cut the necrotic foreskin, such as a scalpel, a pair of scissors, the foreskin cutters or removers described above in FIGS. 15A-17B, or any other suitable instrument, can cut the necrotic foreskin substantially adjacent to circumferential groove 1058 and the capturing ring. Cutting the necrotic foreskin substantially close to the capturing ring eases the removal of the inner ring from the penis and reduces pain an individual may feel when the inner ring is removed. Dead skin tissue is hard and not stretchable like live skin tissue, therefore when the inner ring is removed from the penis (after the foreskin is removed), any dead skin tissue still coupled to the penis may cause sensations of pain as the inner ring is removed, since the live skin tissue adjacent to the dead skin tissue may have to stretch beyond its normal amount as the inner ring is removed. Plurality of troughs 1056 substantially enables a foreskin remover to cut the foreskin substantially close to the capturing ring, thereby minimizing the amount of dead foreskin left on the penis and easing the removal of the inner ring. In addition, the configuration of plurality of protrusions 1054 and plurality of troughs 1056 also reduces the likelihood of the foreskin adhering to the surface of the inner ring as it dries, thereby also easing the removal of the inner ring.

Figure 22C:
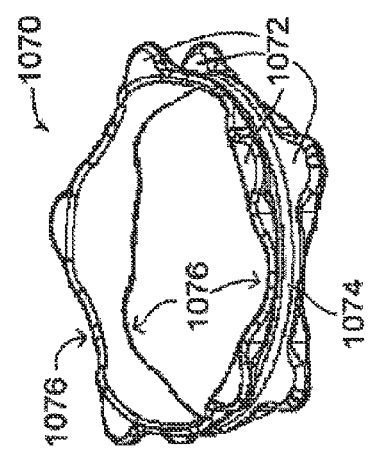

Reference is now made to FIGS. 22C-22G which show various illustrations of second inner ring shape 1070. FIGS. 22C and 22D show perspective views of second inner ring shape 1070. FIG. 22C shows a schematic illustration of second inner ring shape 1070 and FIG. 22D shows a more real-life illustration of second inner ring shape 1070. FIG. 22E shows a side orthogonal view of second inner ring shape 1070, FIG. 22F shows a top orthogonal view of second inner ring shape 1070 and FIG. 22G shows a cross sectional view of second inner ring shape 1070. As shown in FIGS. 22C and 22D, second inner ring shape 1070 includes a plurality of protrusions 1072, a circumferential groove 1074 and a plurality of troughs 1076. Unlike FIGS. 22A and 22B, plurality of protrusions 1072 is located on both ends of second inner ring shape 1070. Circumferential groove 1074 is substantially located and formed between plurality of protrusions 1072 and plurality of troughs 1076. Each one of plurality of troughs 1076 is substantially located between two ones of plurality of protrusions 1072. As shown more clearly, in FIG. 22E, plurality of troughs 1076 substantially abut circumferential groove 1074. Similar to first inner ring shape 1050, second inner ring shape 1070 enables necrotic foreskin to be cut substantially adjacent to a capturing ring (not shown) placed in circumferential groove 1074. In addition, the configuration of plurality of protrusions 1072 and plurality of troughs 1076 also reduces the likelihood of the foreskin adhering to the surface of the inner ring as it dries, thereby also easing the removal of the inner ring. Since plurality of protrusions 1076 are located on both ends of second inner ring shape 1070, second inner ring shape 1070 can be placed either way over a penis (not shown) between the glans or the corona (both not shown) and the foreskin (not shown). As shown in FIG. 22F, in one embodiment, plurality of protrusions 1072 can be evenly spaced around the circumference of second inner ring shape 1070. FIG. 22G shows a cross section view of second inner ring shape 1070 along a line 1078 in FIG. 22F. As can be seen in FIGS. 22C, 22D and 22G, plurality of troughs 1076 depress in an axial direction, shown by a plurality of arrows 1080 (not shown in FIGS. 22C and 22D).

It is noted that the description of the embodiments of the disclosed technique as well as the accompanying figures serve to better understand the disclosed technique without limiting its scope. It is obvious to a person skilled in the art that adjustments, modifications and amendments to the accompanying figures and the described embodiments of the disclosed technique are possible and are within the scope of the disclosed technique. It will be appreciated by persons skilled in the art that the disclosed technique is not limited to what has been particularly shown and described hereinabove. Rather the scope of the disclosed technique is defined only by the claims, which follow.

What is claimed is:

1. A method for circumcising a foreskin of a penis, comprising:
   a) positioning a rigid or semi rigid closed ring element comprising an inner surface comprising an inner diameter; and an outer surface comprising an outer diameter and at least one circumferential groove, around a portion of a glans of the penis;
   b) positioning a deployment element holding an elastic o-ring, around an outer surface of the foreskin, the elastic o-ring being configured to substantially fit around the at least one circumferential groove of the rigid or semi rigid closed ring element, positioning the elastic o-ring over a portion of the foreskin that lies circumferentially over the at least one circumferential groove of the rigid or semi rigid closed ring element, thereby applying a compressive force onto the foreskin, the compressive force being sufficient to effect ischemic necrosis of the foreskin; and
   c) allowing the foreskin to fall off.

2. The method of claim 1, wherein the compressive force is substantially between a pressure range of 0.1-20 atmospheres.

3. The method of claim 1, comprising retracting the foreskin sufficiently to reveal at least a portion of the glans of the penis before positioning the rigid or semi-rigid closed ring element around the portion of the glans of the penis.

4. The method of claim 1, comprising pulling the foreskin over the rigid or semi-rigid closed ring element after the positioning of the rigid or semi-rigid closed ring element around the portion of the glans of the penis.

5. The method of claim 1, comprising stretching an opening of the foreskin sufficiently to insert the rigid or semi-rigid closed ring element through the opening before positioning the rigid or semi-rigid closed ring element around the portion of the glans of said penis.

6. The method of claim 5, comprising vertically positioning the rigid or semi-rigid closed ring element through the opening.

* * * * *